(12) United States Patent
Chen et al.

(10) Patent No.: US 11,375,980 B2
(45) Date of Patent: Jul. 5, 2022

(54) ULTRASOUND APPARATUSES AND METHODS FOR FABRICATING ULTRASOUND DEVICES

(71) Applicant: BFLY Operations, Inc., Guilford, CT (US)

(72) Inventors: Kailiang Chen, Branford, CT (US); Nevada J. Sanchez, Guilford, CT (US); Susan A. Alie, Stoneham, MA (US); Tyler S. Ralston, Clinton, CT (US); Jonathan M. Rothberg, Miami Beach, FL (US); Keith G. Fife, Palo Alto, CA (US); Joseph Lutsky, Los Altos, CA (US)

(73) Assignee: BFLY Operations, Inc., Guilford, CT (US)

( * ) Notice: Subject to any disclaimer, the term of this patent is extended or adjusted under 35 U.S.C. 154(b) by 0 days.

(21) Appl. No.: 16/404,672

(22) Filed: May 6, 2019

(65) Prior Publication Data
US 2019/0261955 A1    Aug. 29, 2019

Related U.S. Application Data

(63) Continuation of application No. 16/192,603, filed on Nov. 15, 2018, now abandoned.
(Continued)

(51) Int. Cl.
*H04B 1/06* (2006.01)
*A61B 8/08* (2006.01)
(Continued)

(52) U.S. Cl.
CPC .......... *A61B 8/5207* (2013.01); *A61B 8/4483* (2013.01); *A61B 8/54* (2013.01); *H04B 11/00* (2013.01)

(58) Field of Classification Search
None
See application file for complete search history.

(56) References Cited

U.S. PATENT DOCUMENTS

| 4,894,114 A | 1/1990 | Nathanson et al. |
| 4,904,831 A | 2/1990 | Nathanson et al. |

(Continued)

FOREIGN PATENT DOCUMENTS

| KR | 101629423 B1 * | 6/2016 | ............. A61B 8/488 |
| KR | 101647797 B1 * | 8/2016 | ............. A61B 8/483 |

(Continued)

OTHER PUBLICATIONS

Koelling, Todd. "Xilinx FPGAs in Portable Ultrasound Systems." White Paper 7 (2010). (Year: 2010).*
(Continued)

*Primary Examiner* — Isam A Alsomiri
*Assistant Examiner* — Jonathan D Armstrong
(74) *Attorney, Agent, or Firm* — Wolf, Greenfield & Sacks, P.C.

(57) ABSTRACT

Aspects of the technology described herein relate to an ultrasound device including a first die that includes an ultrasonic transducer, a first application-specific integrated circuit (ASIC) that is bonded to the first die and includes a pulser, and a second ASIC in communication with the second ASIC that includes integrated digital receive circuitry. In some embodiments, the first ASIC may be bonded to the second ASIC and the second ASIC may include analog processing circuitry and an analog-to-digital converter. In such embodiments, the second ASIC may include a through-silicon via (TSV) facilitating communication between the first ASIC and the second ASIC. In some embodiments, SERDES circuitry facilitates communication between the first ASIC and the second ASIC and the first ASIC includes
(Continued)

analog processing circuitry and an analog-to-digital converter. In some embodiments, the technology node of the first ASIC is different from the technology node of the second ASIC.

14 Claims, 43 Drawing Sheets

Related U.S. Application Data

(60) Provisional application No. 62/687,189, filed on Jun. 19, 2018, provisional application No. 62/586,716, filed on Nov. 15, 2017.

(51) Int. Cl.
    *H04B 11/00*         (2006.01)
    *A61B 8/00*          (2006.01)

(56) References Cited

U.S. PATENT DOCUMENTS

| | | | |
|---|---|---|---|
| 5,722,412 A | 3/1998 | Pflugrath et al. | |
| 5,808,967 A | 9/1998 | Yu et al. | |
| 5,817,024 A | 10/1998 | Ogle et al. | |
| 6,797,891 B1 * | 9/2004 | Blair | H05K 1/147 174/110 R |
| 6,867,668 B1 * | 3/2005 | Dagostino | H01L 23/66 257/E23.065 |
| 7,145,411 B1 * | 12/2006 | Blair | H05K 1/0219 333/5 |
| 8,157,738 B2 | 4/2012 | Wegener et al. | |
| 8,237,228 B2 * | 8/2012 | Or-Bach | H01L 27/105 257/369 |
| 8,273,610 B2 * | 9/2012 | Or-Bach | H01L 27/10802 438/142 |
| 8,294,159 B2 * | 10/2012 | Or-Bach | H01L 27/092 257/74 |
| 8,317,706 B2 | 11/2012 | Wegener | |
| 8,362,482 B2 * | 1/2013 | Or-Bach | H01L 27/0688 257/48 |
| 8,362,800 B2 * | 1/2013 | Or-Bach | H01L 25/0652 326/12 |
| 8,373,439 B2 * | 2/2013 | Or-Bach | H03K 19/1778 326/38 |
| 8,378,715 B2 * | 2/2013 | Or-Bach | H01L 25/18 326/101 |
| 9,351,706 B2 * | 5/2016 | Rothberg | G01S 7/52084 |
| 10,082,565 B2 * | 9/2018 | Chen | G01S 7/52022 |
| 10,175,347 B2 * | 1/2019 | Chen | G01S 7/5273 |
| 10,231,713 B2 * | 3/2019 | Chen | A61B 8/56 |
| 10,327,733 B2 * | 6/2019 | Lee | A61B 8/085 |
| 10,340,866 B2 * | 7/2019 | Singh | H03F 3/45179 |
| 10,340,867 B2 * | 7/2019 | Singh | H03F 3/45179 |
| 2001/0051766 A1 | 12/2001 | Gazdzinski | |
| 2002/0198455 A1 | 12/2002 | Ossman et al. | |
| 2003/0011285 A1 | 1/2003 | Ossman | |
| 2003/0013969 A1 | 1/2003 | Eriskon et al. | |
| 2003/0028341 A1 * | 2/2003 | Fallon | G01S 7/52034 702/117 |
| 2003/0097071 A1 * | 5/2003 | Halmann | A61B 8/14 600/459 |
| 2003/0139664 A1 * | 7/2003 | Hunt | A61B 8/00 600/407 |
| 2003/0163047 A1 * | 8/2003 | Little | G01S 7/5203 600/457 |
| 2004/0000841 A1 | 1/2004 | Phelps et al. | |
| 2004/0002435 A1 | 1/2004 | Petersen et al. | |
| 2004/0002652 A1 | 1/2004 | Phelps et al. | |
| 2004/0002656 A1 | 1/2004 | Sheljaskow et al. | |
| 2004/0158154 A1 * | 8/2004 | Hanafy | A61B 8/4483 600/446 |
| 2005/0037800 A1 | 2/2005 | Shih | |
| 2005/0228279 A1 | 10/2005 | Ustuner et al. | |
| 2006/0074320 A1 * | 4/2006 | Yoo | A61B 8/08 600/472 |
| 2007/0014190 A1 * | 1/2007 | Fehl | B06B 1/0215 367/138 |
| 2007/0016023 A1 * | 1/2007 | Phelps | G01S 7/52023 600/437 |
| 2007/0040626 A1 * | 2/2007 | Blair | H01P 3/006 333/1 |
| 2009/0082673 A1 * | 3/2009 | Lu | A61B 8/4281 600/459 |
| 2009/0093719 A1 * | 4/2009 | Pelissier | A61B 8/00 600/447 |
| 2010/0133704 A1 | 6/2010 | Marimuthu et al. | |
| 2010/0174195 A1 | 7/2010 | Haider et al. | |
| 2010/0328189 A1 | 12/2010 | Laknin et al. | |
| 2011/0055447 A1 | 3/2011 | Costa et al. | |
| 2011/0121922 A1 * | 5/2011 | Blair | H05K 1/0219 333/238 |
| 2013/0303919 A1 | 11/2013 | Corl | |
| 2014/0056104 A1 | 2/2014 | Buechler et al. | |
| 2014/0121524 A1 | 5/2014 | Chiang et al. | |
| 2014/0288428 A1 * | 9/2014 | Rothberg | A61B 8/145 600/447 |
| 2015/0080724 A1 | 3/2015 | Rothberg et al. | |
| 2015/0087991 A1 * | 3/2015 | Chen | G01S 7/52033 600/459 |
| 2016/0011305 A1 | 1/2016 | Koptenko | |
| 2016/0133600 A1 | 5/2016 | Shen et al. | |
| 2016/0157818 A1 | 6/2016 | Cho et al. | |
| 2016/0199034 A1 | 7/2016 | Labyed et al. | |
| 2017/0156697 A1 | 6/2017 | Cho et al. | |
| 2018/0054575 A1 | 2/2018 | Pawlowicz et al. | |
| 2018/0242956 A1 * | 8/2018 | Somerville | G06F 1/3203 |
| 2019/0142387 A1 * | 5/2019 | Chen | H04B 11/00 367/135 |
| 2019/0212424 A1 | 7/2019 | Savord et al. | |
| 2019/0261954 A1 | 8/2019 | Chen et al. | |

FOREIGN PATENT DOCUMENTS

| | | | | |
|---|---|---|---|---|
| TW | I555386 B | * | 1/2016 | ............. A61B 8/488 |
| WO | WO 2010/141370 A2 | | 12/2010 | |
| WO | WO 2011/008408 A2 | | 1/2011 | |
| WO | WO-2014096789 A2 | * | 6/2014 | ........... B06B 1/0215 |
| WO | WO 2018-041635 A1 | | 3/2018 | |

OTHER PUBLICATIONS

Tan, Mingliang, et al. "A front-end ASIC with high-voltage transmit switching and receive digitization for forward-looking intravascular ultrasound." 2017 IEEE Custom Integrated Circuits Conference (CICC). IEEE, 2017. (Year: 2017).*

Tang, Hao-Yen. Interface Electronics for Ultrasonic Transducers. University of California, Berkeley, 2016. (Year: 2016).*

International Search Report and Written Opinion dated Jan. 24, 2019 in connection with International Application No. PCT/US2018/061238.

U.S. Appl. No. 16/192,603, filed Nov. 15, 2018, Chen et al.

U.S. Appl. No. 16/404,665, filed May 6, 2019, Chen et al.

Huang, Xiwei, et al. "Transimpedance Amplifier for Integrated 3D Ultrasound Biomicroscope Applications." World Academy of Science Engineering and technology 69 (2012). (Year: 2012).

Yang, Hyung Suk. Large-scale silicon system technologies: through-silicon vias, mechanically flexible interconnects, and positive self-alignment structures. Diss. Georgia Institute of Technology, 2014. (Year: 2014).

International Preliminary Report on Patentability dated May 28, 2020 in connection with International Application No. PCT/US2018/061238.

Extended European Search Report dated Jul. 6, 2021 in connection with European Application No. 18879151.1.

Attarzadeh et al., Stacking Integration Methodologies in 3D IC for 3D Ultrasound Image Processing Application: A Stochastic Flash

(56) References Cited

OTHER PUBLICATIONS

ADC Design Case Study. 2015 IEEE International Symposium on Circuits and Systems (ISCAS). IEEE. May 24, 2015; pp. 1266-1269.

* cited by examiner

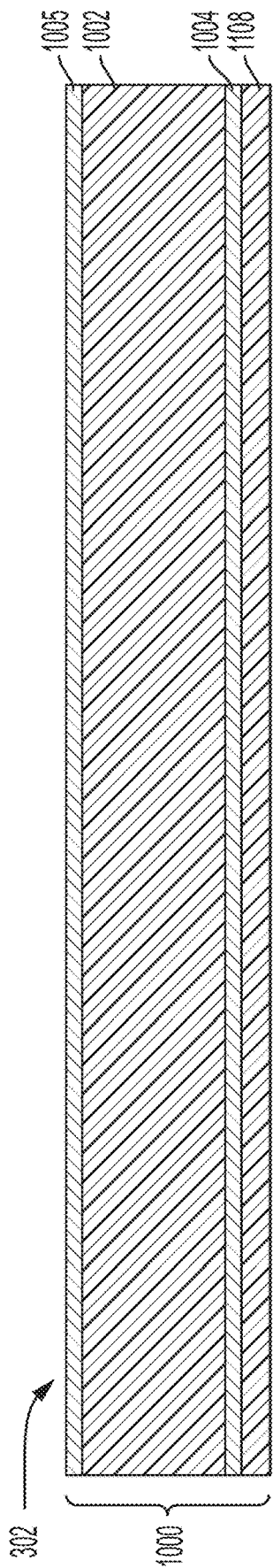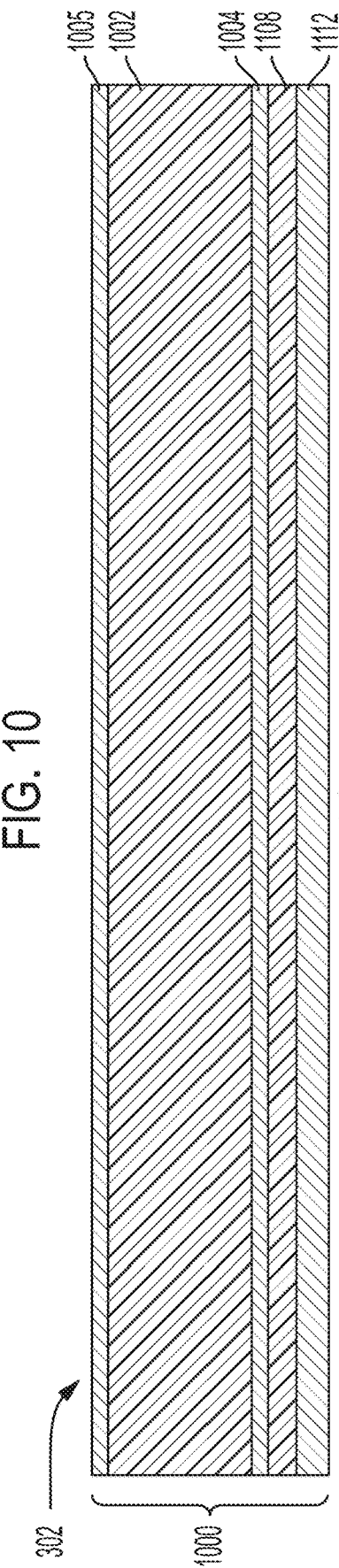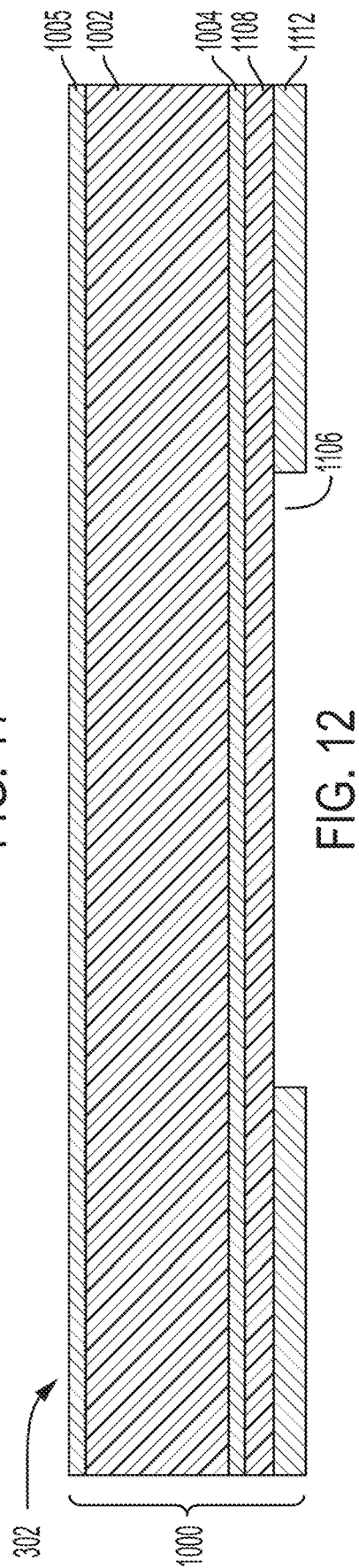

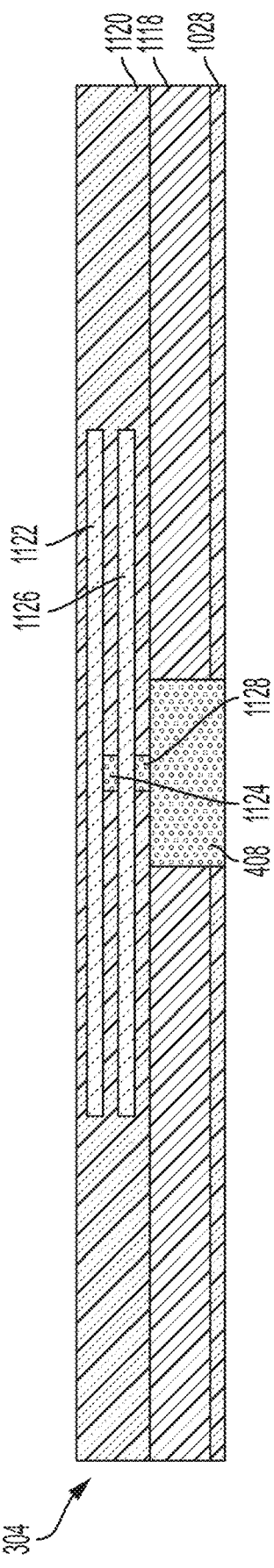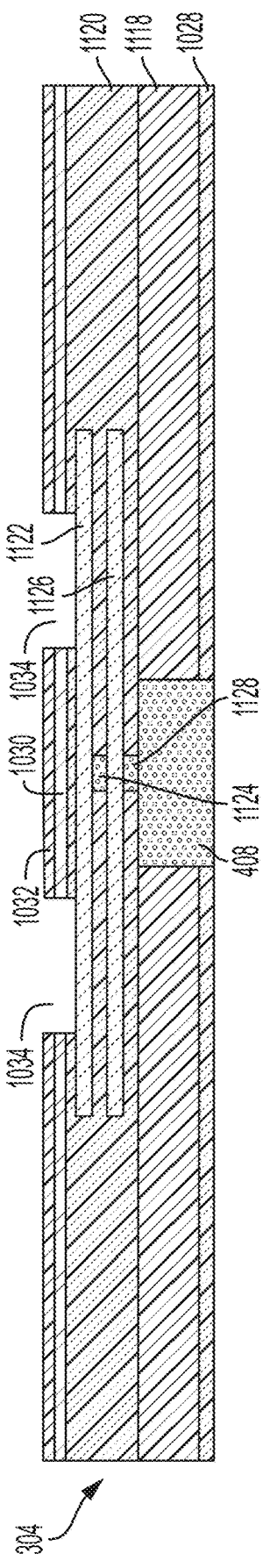
FIG. 20
FIG. 21
FIG. 22

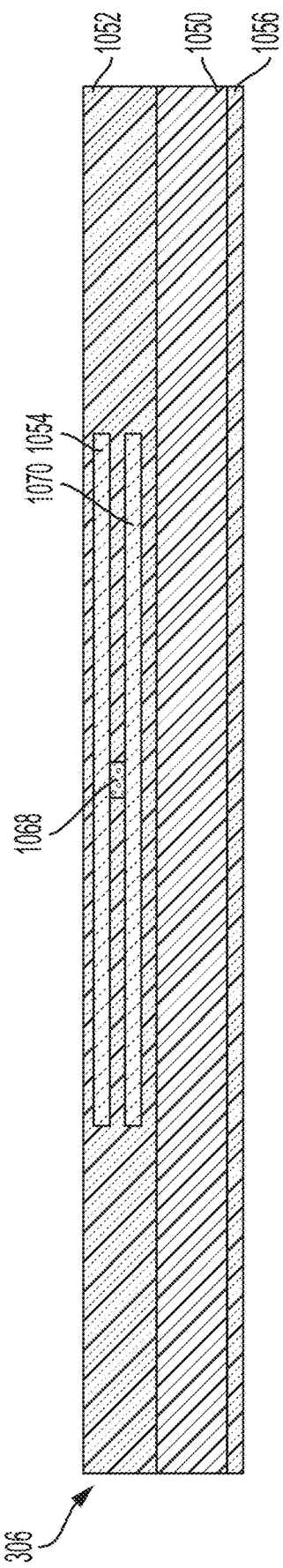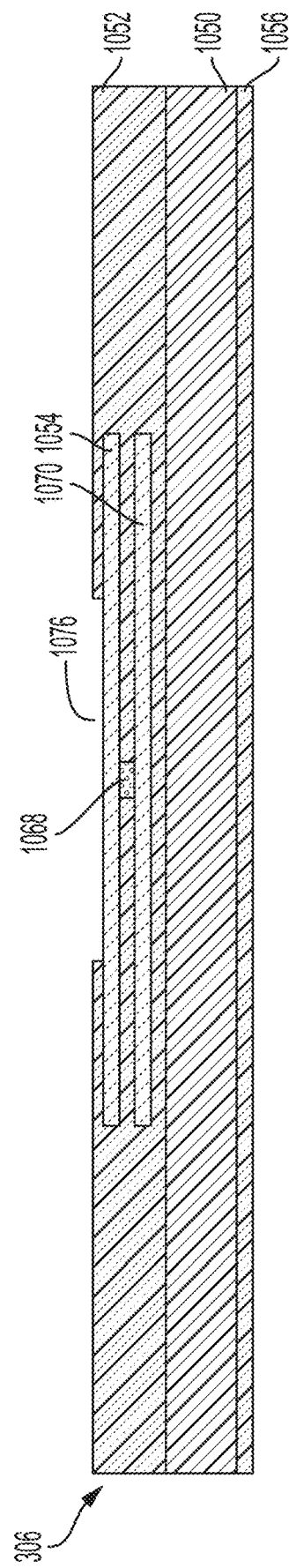
FIG. 36
FIG. 37

ULTRASOUND APPARATUSES AND METHODS FOR FABRICATING ULTRASOUND DEVICES

CROSS-REFERENCE TO RELATED APPLICATIONS

This application is a Continuation of U.S. application Ser. No. 16/192,603, filed Nov. 15, 2018, and entitled "ULTRASOUND APPARATUSES AND METHODS FOR FABRICATING ULTRASOUND DEVICES", which is hereby incorporated herein by reference in its entirety.

U.S. application Ser. No. 16/192,603 claims the benefit under 35 U.S.C. § 119(e) of U.S. Provisional Patent Application Ser. No. 62/586,716, filed Nov. 15, 2017, and entitled "METHODS AND APPARATUS FOR IMPLEMENTING INTEGRATED TRANSMIT AND RECEIVE CIRCUITRY IN AN ULTRASOUND DEVICE," which is hereby incorporated herein by reference in its entirety.

U.S. application Ser. No. 16/192,603 claims the benefit under 35 U.S.C. § 119(e) of U.S. Provisional Patent Application Ser. No. 62/687,189, filed Jun. 19, 2018 and entitled "APPARATUSES INCLUDING A CAPACITIVE MICROMACHINED ULTRASONIC TRANSDUCER DIRECTLY COUPLED TO AN ANALOG-TO-DIGITAL CONVERTER," which is hereby incorporated herein by reference in its entirety.

FIELD

Generally, the aspects of the technology described herein relate to ultrasound devices. Some aspects relate to implementing integrated transmit circuitry and integrated receive circuitry in ultrasound devices.

BACKGROUND

Ultrasound probes may be used to perform diagnostic imaging and/or treatment, using sound waves with frequencies that are higher than those audible to humans. Ultrasound imaging may be used to see internal soft tissue body structures. When pulses of ultrasound are transmitted into tissue, sound waves of different amplitudes may be reflected back towards the probe at different tissue interfaces. These reflected sound waves may then be recorded and displayed as an image to the operator. The strength (amplitude) of the sound signal and the time it takes for the wave to travel through the body may provide information used to produce the ultrasound image. Many different types of images can be formed using ultrasound devices. For example, images can be generated that show two-dimensional cross-sections of tissue, blood flow, motion of tissue over time, the location of blood, the presence of specific molecules, the stiffness of tissue, or the anatomy of a three-dimensional region.

SUMMARY

According to one aspect of the technology, an ultrasound device is provided, comprising: a first die that comprises an ultrasonic transducer; a first application-specific integrated circuit (ASIC) that is bonded to the first die and comprises a pulser; and a second ASIC in communication with the first ASIC that comprises integrated digital receive circuitry. Alternative configurations for implementing ultrasonic transducers, transmit circuitry, and receive circuitry are also described.

BRIEF DESCRIPTION OF THE DRAWINGS

Various aspects and embodiments will be described with reference to the following exemplary and non-limiting figures. It should be appreciated that the figures are not necessarily drawn to scale. Items appearing in multiple figures are indicated by the same or a similar reference number in all the figures in which they appear.

FIGS. 10-32 illustrate example cross-sections of the ultrasound device during a fabrication sequence for forming the ultrasound device in accordance with certain embodiments described herein;

FIGS. 33-42 illustrate example cross-sections of an ultrasound device during an alternative fabrication sequence to that of FIGS. 20-32 in accordance with certain embodiments described herein;

DETAILED DESCRIPTION

Figure 1:
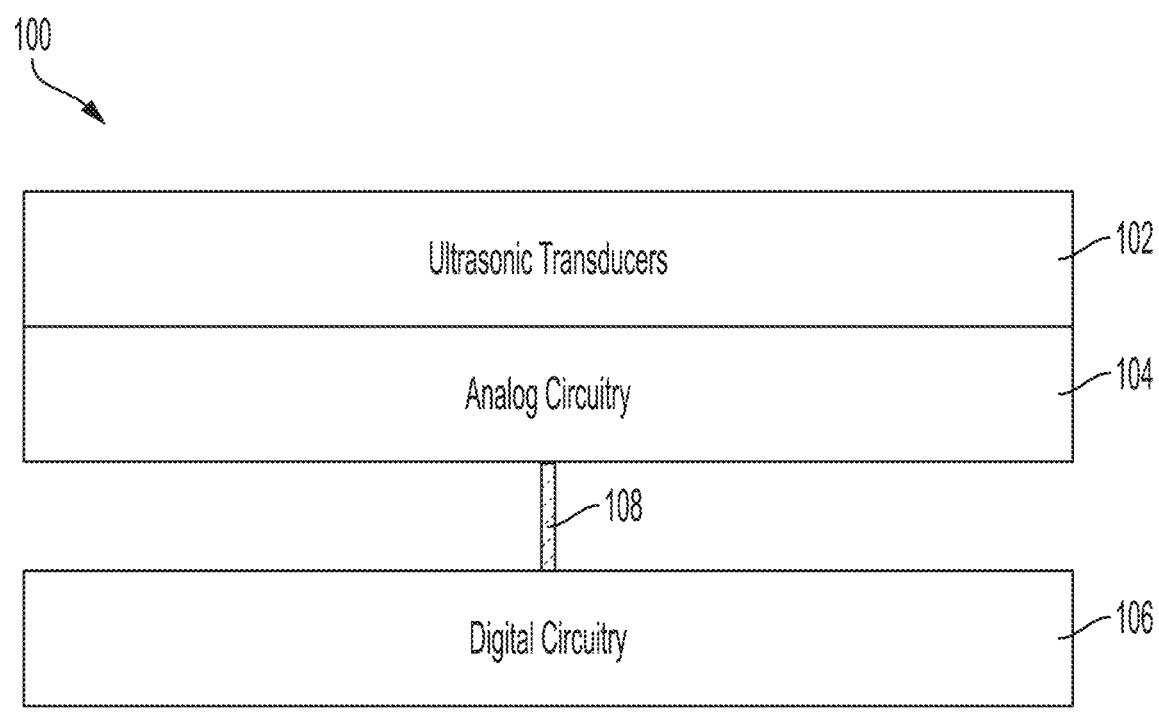
FIG. 1 illustrates a block diagram of an ultrasound device in accordance with certain embodiments described herein.

Conventional ultrasound systems are large, complex, and expensive systems that are typically only purchased by large medical facilities with significant financial resources. Recently, less costly and less complex ultrasound imaging devices have been introduced. Such imaging devices may include ultrasonic transducers monolithically integrated onto a single semiconductor die to form a monolithic ultrasound device. Aspects of such ultrasound-on-a chip devices are described in U.S. patent application Ser. No. 15/415,434 titled "UNIVERSAL ULTRASOUND DEVICE AND RELATED APPARATUS AND METHODS," filed on Jan. 25, 2017 and published as U.S. Pat. Publication No. 2017/0360397 A1 (and assigned to the assignee of the instant application), which is incorporated by reference herein in its entirety.

Some implementations of monolithic ultrasound devices may include integrated transmit circuitry and integrated receive circuitry implemented in the same device (e.g., die). The integrated transmit circuitry and integrated receive circuitry may be, for example, complementary metal-oxide-semiconductor (CMOS) circuitry. The integrated transmit circuitry may be configured to drive ultrasonic transducers to emit pulsed ultrasonic signals into a subject, such as a patient. The integrated transmit circuitry may include integrated analog circuitry such as pulsers. The pulsed ultrasonic signals may be back-scattered from structures in the body, such as blood cells or muscular tissue, to produce echoes that return to the ultrasonic transducers. These echoes may then be converted into electrical signals by the transducer elements. The integrated receive circuitry may be configured to convert the electrical signals representing the received echoes into ultrasound data that can, for example, be formed into an ultrasound image. The integrated receive circuitry may include integrated analog circuitry, such as analog processing circuitry and analog-to-digital converters (ADCs), and integrated digital circuitry, such as image formation circuitry.

The inventors have recognized that, in certain embodiments, it may be helpful to implement analog portions of the integrated transmit circuitry (e.g., pulsers) and analog portions of the integrated receive circuitry (e.g., amplifiers and ADCs) in one device (e.g., an application-specific integrated circuit (ASIC)) that is bonded to a device including ultrasonic transducers, and to implement digital portions of the integrated receive circuitry (e.g., image formation circuitry) in another device (e.g., an ASIC). This may allow the device having the integrated analog circuitry to be implemented in a different technology node than the device having the integrated digital circuitry. In some embodiments, any digital transmit circuitry may be split between the devices, or implemented entirely on one or the other of the devices. As will be described below, the integrated analog circuitry may benefit from implementation in a less advanced (larger) technology node than the integrated digital circuitry, and the integrated digital circuitry may benefit from implementation in a more advanced (smaller) technology node than the integrated analog circuitry.

To drive the ultrasonic transducers, the inventors have recognized that pulsers may benefit from operating at high voltages that are approximately equal to or greater than 10 V, such as 10 V, 20 V, 30 V, 40 V, 50 V, 60 V, 70 V, 80 V, 90 V, 100 V, 200 V, or >200 V, or any value between 10 V and 300 V. Increasingly higher voltage levels of electronic signals outputted to ultrasonic transducers by the integrated transmit circuitry may correspond to higher pressure levels of acoustic signals outputted by the ultrasonic transducers. High pressure levels may be helpful for emitting acoustic signals into a patient, as pressure levels of acoustic signals are attenuated as they travel deeper into a patient. High pressure levels may also be necessary for certain types of ultrasound imaging such as tissue harmonic imaging. Circuit devices capable of operating at acceptably high voltage levels may only be available in sufficiently large technology nodes such as 65 nm, 80 nm, 90 nm, 110 nm, 130 nm, 150 nm, 180 nm, 220 nm, 240 nm, 250 nm, 280 nm, 350 nm, 500 nm, >500 nm, etc.

Furthermore, when the amplifiers and ADCs are in the same device as the pulsers, the amplifiers and ADCs may receive weak signals from the ultrasonic transducers through the bonds between the two devices, amplify them, and digitize them. Tight coupling (e.g., low-resistance paths) between the device having the integrated analog circuitry and the device having the integrated digital circuitry may therefore not be necessary because the digitized signals outputted by analog-to-digital converters in the integrated analog circuitry to the device having the integrated digital circuitry may be resilient to attenuation and noise. In some embodiments, a high-speed communication link such as a serial-deserializer (SERDES) link may facilitate communication between the device having the integrated analog circuitry and the device having the integrated digital circuitry.

It may be helpful for the integrated digital circuitry, which may perform digital processing operations, to operate at low voltages that are approximately equal to or lower than, for example, 1.8 V, such as 1.8 V, 1.5 V, 1 V, 0.95 V, 0.9 V, 0.85 V, 0.8 V, 0.75 V, 0.7 V, 0.65 V, 0.6 V, 0.55 V, 0.5 V, and 0.45 V. The integrated digital circuitry may be densely integrated in order to increase its parallel computing power and may consume a significant portion (e.g., half) of the ultrasound device's power. Scaling the operating voltage of the integrated receive circuitry down by a factor N (where N>1) can reduce the power consumption by a factor $N^x$ (where $x \geq 1$), such as $N^2$. Circuit devices capable of operating at acceptably low voltage levels may, in some embodiments, only be available in technology nodes such as 90 nm, 80 nm, 65 nm, 55 nm, 45 nm, 40 nm, 32 nm, 28 nm, 22 nm, 20 nm, 16 nm, 14 nm, 10 nm, 7 nm, 5 nm, 3 nm, etc. Furthermore, the inventors have recognized that it may be beneficial for the integrated digital circuitry to include smaller devices, for example sizes provided by technology nodes such as 90 nm, 80 nm, 65 nm, 55 nm, 45 nm, 40 nm, 32 nm, 28 nm, 22 nm, 20 nm, 16 nm, 14 nm, 10 nm, 7 nm, 5 nm, 3 nm, etc.), to increase the number of devices that can be included in a die of a given size, and thereby increase the processing (e.g., data conversion and image formation) capability of the integrated digital circuitry.

The inventors have also recognized that, in certain embodiments, it may be helpful to implement the integrated transmit circuitry (e.g., pulsers) in one device that is bonded to a device including ultrasonic transducers, and to implement integrated receive circuitry (e.g., amplifiers, ADCs, and image formation circuitry) in another device. This may allow the device having the integrated transmit circuitry to be implemented in a different technology node than the device having the integrated receive circuitry. The integrated transmit circuitry may benefit from implementation in a more advanced (smaller) technology node than the integrated receive circuitry, and the integrated receive circuitry may benefit from implementation in a less advanced (larger) technology node than the integrated transmit circuitry.

For considerations described above, the integrated transmit circuitry (e.g., pulsers) may benefit from operating at high voltages that may only be available in technology nodes such as 65 nm, 80 nm, 90 nm, 110 nm, 130 nm, 150 nm, 180 nm, 220 nm, 240 nm, 250 nm, 280 nm, 350 nm, 500 nm, >500 nm, etc. For the power and density considerations described above, the integrated receive circuitry (e.g., amplifiers, ADCs, and image formation circuitry) may benefit from implementation in technology nodes such as 90 nm, 80 nm, 65 nm, 55 nm, 45 nm, 40 nm, 32 nm, 28 nm, 22 nm, 20 nm, 16 nm, 14 nm, 10 nm, 7 nm, 5 nm, 3 nm, etc. that provide small circuit devices capable of operating at acceptably low voltage levels. A difference between this embodiment and the embodiment described above (in which integrated analog circuitry such as amplifiers, ADCs, and pulsers are in one device with a less advanced (larger) technology node and integrated digital circuitry is in another device with a more advanced (smaller) technology node) may be that the analog receive circuitry (e.g., amplifiers and ADCs) may be implemented in a more advanced technology node in this embodiment. Because amplifiers and ADCs can consume significant power, implementing these circuits in a more advanced technology node may further reduce the power consumed by the ultrasound device.

Accordingly, in this embodiment, the ultrasound device may include a stack of three devices (e.g., wafers or dies): a first device including ultrasonic transducers, followed below by a second device including integrated transmit circuitry, followed below by a third device including integrated receive circuitry, each device bonded to the adjacent device(s).

The inventors have further recognized that in the stack described above, it may be necessary to transmit a relatively weak analog electrical signal (e.g., on the order of millivolts or microvolts) representing a received ultrasound echo from the first device where it is received, through the second device below the first device, and to the third device for processing (e.g., amplification and digitization) by the integrated receive circuitry. The inventors have recognized that through-silicon vias (TSVs) implemented in the second device may enable the weak electrical signals to pass through the second device with acceptably low attenuation. The inventors have also recognized that it may be helpful to thin the second device in order to reduce the height of TSVs, for example to reduce the capacitance of the TSVs.

In certain embodiments, a hybrid of the above embodiments may include a three-die stack in which SERDES communication links facilitate high-speed communication from the second device to the third device through TSVs.

As referred to herein in the specification and claims a device including a specific type of circuitry should be understood to mean that the device includes only that specific type of circuitry or that the device includes that specific type of circuitry and another type/other types of circuitry. For example, if an ultrasound device includes a second device and a third device, where the second device includes "integrated transmit circuitry" or "the integrated transmit circuitry" and the third device includes "integrated receive circuitry" or "the integrated receive circuitry," this may mean that the second device includes all the integrated transmit circuitry in the ultrasound device, the second device includes a portion of the integrated transmit circuitry in the ultrasound device, the third device includes all the integrated receive circuitry in the ultrasound device, and/or the third device includes a portion of the integrated receive circuitry in the ultrasound device. Furthermore, the second device may include only integrated transmit circuitry or other types of circuitry. For example, the second device may include both integrated transmit circuitry and integrated receive circuitry. Furthermore, the third device may include only integrated receive circuitry or other types of circuitry. For example, the third device may include both integrated receive circuitry and integrated transmit circuitry.

It should be appreciated that the embodiments described herein may be implemented in any of numerous ways. Examples of specific implementations are provided below for illustrative purposes only. It should be appreciated that these embodiments and the features/capabilities provided may be used individually, all together, or in any combination of two or more, as aspects of the technology described herein are not limited in this respect.

FIG. 1 illustrates a block diagram of an ultrasound device 100 in accordance with certain embodiments described herein. The ultrasound device includes a first device 102, a second device 104, a third device 106, and a communication link 108. The first device 102 and the second device 104 may be, for example, dies. The second device 104 may be an application-specific integrated circuit (ASIC)). Each device may include multiple layers of materials (e.g., silicon, oxides, metals, etc.). The first device 102 and the second device 104 are bonded together. A bottom surface of the first device 102 is bonded to a top surface of the second device 104. The bonding between the first device 102 and the second device 104 may include, for example, thermal compression (also referred to herein as "thermocompression"), eutectic bonding, silicide bonding (which is a bond formed by bringing silicon of one substrate into contact with metal on a second substrate under sufficient pressure and temperature to form a metal silicide, creating a mechanical and electrical bond), or solder bonding. The first device 102 and the second device 104 may have been bonded together as wafers including multiple dies that were subsequently diced. The third device 106 may be, for example, a die (e.g., an application-specific integrated circuit (ASIC)) or another type of electronic device (e.g., a microprocessor or field-programmable gate array (FPGA)).

The ultrasound device 100 may be configured to drive ultrasonic transducers to emit pulsed ultrasonic signals into a subject, such as a patient. The pulsed ultrasonic signals may be back-scattered from structures in the body, such as blood cells or muscular tissue, to produce echoes that return to the ultrasonic transducers. These echoes may then be converted into electrical signals by the transducer elements. The electrical signals representing the received echoes are then converted into ultrasound data.

The first device 102 includes the ultrasonic transducers. Example ultrasonic transducers include capacitive micromachined ultrasonic transducers (CMUTs), CMOS ultrasonic transducers (CUTs), and piezoelectric micromachined ultrasonic transducers (PMUTs). For example, CMUTs and CUTs may include cavities formed in a substrate with a membrane/membranes overlying the cavity. The ultrasonic transducers may be arranged in an array (e.g., one-dimensional or two-dimensional). The second device 104 includes integrated analog circuitry, which may include integrated analog transmit circuitry and integrated analog receive circuitry. The integrated analog transmit circuitry may include one or more pulsers configured to receive waveforms from one or more waveform generators and output driving signals corresponding to the waveforms to the ultrasonic transducers. The integrated analog receive circuitry may include one or more analog amplifiers, one or more analog filters, analog beamforming circuitry, analog dechirp circuitry, analog quadrature demodulation (AQDM) circuitry, analog time delay circuitry, analog phase shifter circuitry, analog summing circuitry, analog time gain compensation circuitry, analog averaging circuitry, and/or one or more analog-to-digital converters. The third device 106 includes integrated digital receive circuitry, which may include, for example, one or more digital filters, digital beamforming circuitry, digital quadrature demodulation (DQDM) circuitry, averaging circuitry, digital dechirp circuitry, digital time delay circuitry, digital phase shifter circuitry, digital summing circuitry, digital multiplying circuitry, requantization circuitry, waveform removal circuitry, image formation circuitry, backend processing circuitry and/or one or more output buffers.

The second device 104 may be implemented in a different technology node than the third device 106 is, and the technology node of the third device 106 may be a more advanced technology node with smaller feature sizes than the technology node in which the second device 104 is implemented. For example, the technology node of the second device 104 may be a technology node that provides circuit devices (e.g., transistors) capable of operating at voltages in the range of approximately 80-200 V, such as 80 V, 90 V, 100 V, 200 V, or >200 V. In some embodiments, the technology node of the second device 104 may be a technology node that provides circuit devices (e.g., transistors) capable of operating at other voltages, such as voltages in the range of approximately 5-30 V or voltages in the range of approximately 30-80V. By operating at such voltages, circuitry in the second device 104 may be able to drive the ultrasonic transducers in the first device 102 to emit acoustic waves having acceptably high pressures. The technology node of the second device 104 may be, for example, 65 nm, 80 nm, 90 nm, 110 nm, 130 nm, 150 nm, 180 nm, 220 nm, 240 nm, 250 nm, 280 nm, 350 nm, 500 nm, >500 nm, or any other suitable technology node.

The technology node of the third device 106, for example, may be one that provides circuit devices (e.g., transistors) capable of operation at a voltage in the range of approximately 0.45-0.9V, such as 0.9V, 0.85V, 0.8V, 0.75V, 0.7V, 0.65V, 0.6V, 0.6V, 0.55V, 0.5V, and 0.45V. In some embodiments, the technology node of the third device 106 may be one that provides circuit device capable of operation at a voltage in the range of approximately 1-1.8 V, or approximately 2.5-3.3 V. By operating at such voltages, power consumption of circuitry in the third device 106 may be reduced to an acceptable level. Additionally, the feature size of devices provided by the technology node may enable an acceptably high degree of integration density of circuitry in the third device 106. The technology node of the third device 106 may be, for example, 90 nm, 80 nm, 65 nm, 55 nm, 45 nm, 40 nm, 32 nm, 28 nm, 22 nm, 20 nm, 16 nm, 14 nm, 10 nm, 7 nm, 5 nm, 3 nm, etc.

The communication link 108 may facilitate communication between the second device 104 and the third device 106. For example, the second device 104 may offload data to the third device 106 over the communication link 108. To offload data at a high data rate, the communication link 108 may include one or more serial-deserializer (SERDES) links. A SERDES link may include SERDES transmit circuitry in the second device 104, SERDES receive circuitry in the third device 106, and an electrical link trace between the SERDES transmit circuitry and the SERDES receive circuitry. In some embodiments, the ultrasound device 100 may include a PCB to which the first device 102, the second device 104, and the third device 106 are coupled. For example, the bonded stack of the first device 102 and second device 104 may be coupled to the PCB at one location, the third device 106 may be coupled to the PCB at another location, and traces implementing portions of the communication link 108 may extend between the two locations. In particular, when a SERDES link is used, the communication link 108 may include a trace on the PCB electrically connecting the SERDES transmit circuitry in the second device 104 to the SERDES receive circuitry in the third device 106. In some embodiments, the communication link 108 (e.g., a SERDES link) may be capable of transmitting data at a rate of approximately 2-5 gigabits/second. In some embodiments, there may be more than one communication link 108 operating in parallel. In some embodiments, there may be approximately equal to or between 1-100 parallel SERDES communication links 108. In some embodiments, there may be approximately equal to or between 1-10,000 parallel SERDES communication links 108. The data offload rate of all the parallel communication links may make the ultrasound device 100 acoustically limited, meaning that it may not be necessary to insert undesired time between collection of frames of ultrasound data to offload data from the ultrasound device 100. The data offload rate may facilitate high pulse repetition intervals (e.g., greater than or equal to approximately 10 kHz).

Figure 2:
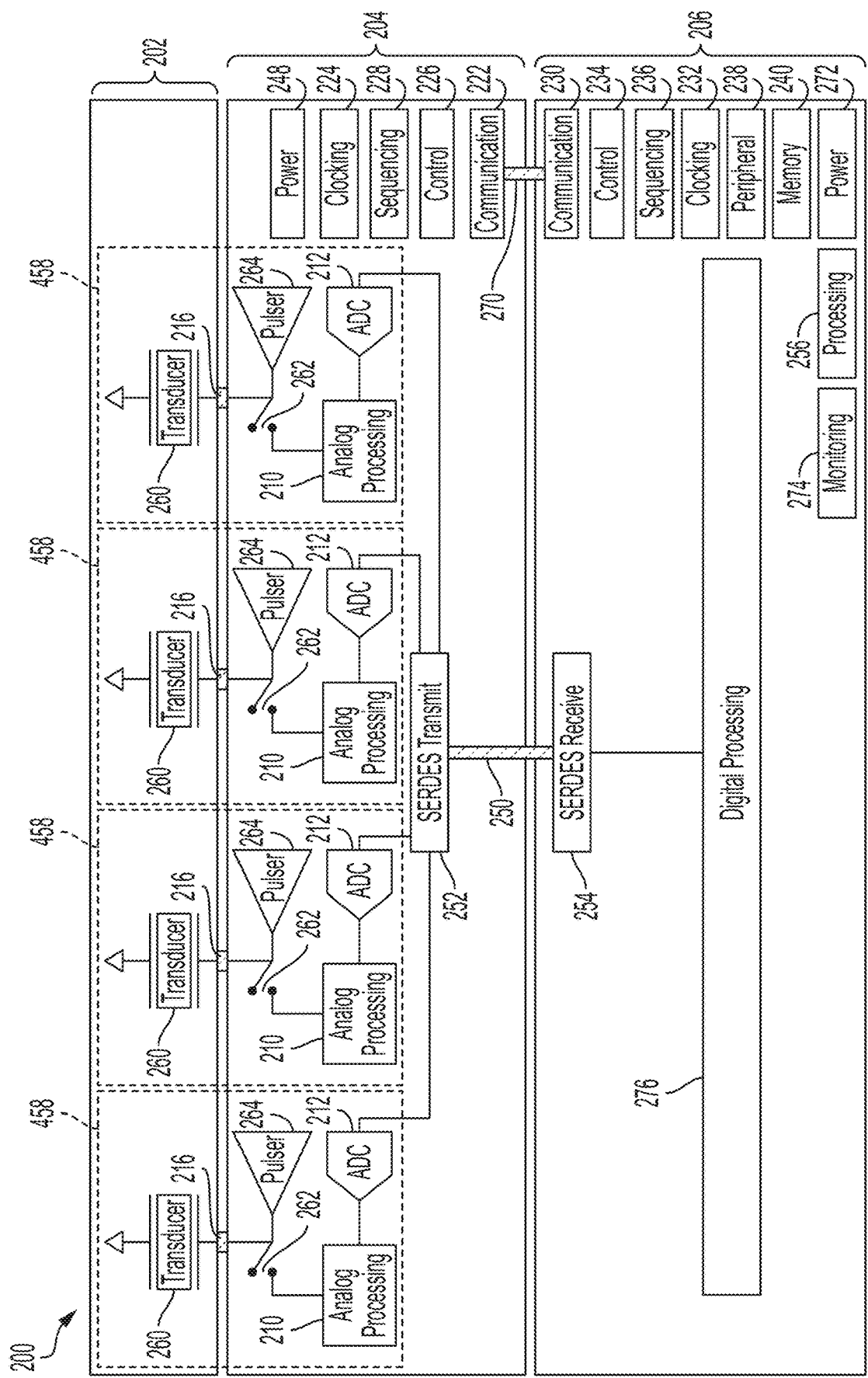
FIG. 2 illustrates a block diagram of another ultrasound device in accordance with certain embodiments described herein.

FIG. 2 illustrates an example block diagram of an ultrasound device 200, in accordance with certain embodiments described herein. The ultrasound device 200 includes a first device 202, a second device 204, and a third device 206. The ultrasound device 200, the first device 202, the second device 204, and the third device 206 may be examples of the ultrasound device 100, the first device 102, the second device 104, and the third device 106, respectively, illustrated in more detail. The ultrasound device 200 includes a plurality of elements 458 (which may also be considered pixels). While only four elements 458 are shown in FIG. 2, it should be appreciated that many more elements 458 may be included, such as hundreds, thousands, or tens of thousands of elements. Each of the elements 458 includes an ultrasonic transducer 260, a pulser 264, a receive switch 262, an analog processing circuitry 210 block, and an analog-to-digital converter (ADC) 212. The first device 202 includes the ultrasonic transducers 260. The second device 204 includes the pulsers 264, the receive switches 262, the analog processing circuitry 210, the ADCs 212, and SERDES transmit circuitry 252. The third device 206 includes SERDES receive circuitry 254 and digital processing circuitry 276. Bonding points 216 electrically connect the ultrasonic transducers 260 in the first device 202 to the pulsers 264 and the receive switches 262 in the second device 204. A communication link 250 electrically connects the SERDES transmit circuitry 252 in the second device 204 to the SERDES receive circuitry 254 in the third device 206.

A pulser 264 may be configured to output a driving signal to an ultrasonic transducer 260 through a bonding point 216. The pulser 264 may receive a waveform from a waveform generator (not shown) and be configured to output a driving signal corresponding to the received waveform. When the pulser 264 is driving the ultrasonic transducer 260 (the "transmit phase"), the receive switch 262 may be open such that the driving signal is not applied to receive circuitry (e.g., the analog processing circuitry 210).

The ultrasonic transducer 260 may be configured to emit pulsed ultrasonic signals into a subject, such as a patient, in response to the driving signal received from the pulser 264. The pulsed ultrasonic signals may be back-scattered from structures in the body, such as blood cells or muscular tissue, to produce echoes that return to the ultrasonic transducer 260. The ultrasonic transducer 260 may be configured to convert these echoes into electrical signals. When the ultrasonic transducer 260 is receiving the echoes (the "receive phase"), the receive switch 262 may be closed such that the ultrasonic transducer 260 may transmit the electrical signals representing the received echoes through the bonding point 216 and the receive switch 262 to the analog processing circuitry 210.

The analog processing circuitry 210 may include, for example, one or more analog amplifiers, one or more analog filters, analog beamforming circuitry, analog dechirp circuitry, analog quadrature demodulation (AQDM) circuitry, analog time delay circuitry, analog phase shifter circuitry, analog summing circuitry, analog time gain compensation circuitry, and/or analog averaging circuitry. The analog output of the analog processing circuitry 210 is outputted to the ADC 212 for conversion to a digital signal. The digital output of the ADC 212 is outputted to the SERDES transmit circuitry 252.

The SERDES transmit circuitry 252 may be configured to convert parallel digital output of the ADC 212 to a serial digital stream and to output the serial digital stream at a high-speed (e.g., 2-5 gigabits/second) over the communication link 250. As described above, the bonded stack of the first device 202 and second device 204 may be coupled to the PCB at one location and the third device 206 may be coupled to the PCB at another location. The communication link 250 may be, for example, a trace on a PCB that electrically connects the SERDES transmit circuitry 252 in the second device 204 to the SERDES receive circuitry 254 in the third device 206. The SERDES receive circuitry 254 may be configured to convert the serial digital stream received from the communication link 250 to a parallel digital output and to output this parallel digital output to the digital processing circuitry 276. The SERDES transmit circuitry 252, the SERDES receive circuitry 254, and the communication link 250 may be an example of the communication link 108.

In the ultrasound device 200, one block of SERDES transmit circuitry 252 receives data from multiple ADC's 212 and is electrically coupled, through the communication link 250, to one block of SERDES receive circuitry 254 that is coupled to the digital processing circuitry 276. There may be multiple instances of SERDES transmit circuitry 252, communication link 250, and SERDES receive circuitry 254, each receiving data from multiple ADC's 212. In some embodiments, there may be one instance of SERDES transmit circuitry 252, communication link 250, and SERDES receive circuitry 254 per ADC 212 and/or per ultrasonic transducer 260, or more generally, per element 458.

In some embodiments, the SERDES receive circuitry 254 may include a mesochronous receiver. In some embodiments, the SERDES receive circuitry 254 may include a digital phase-locked loop (PLL), a digital clock and data recovery circuit, and an equalizer. In some embodiments, the PLL of the SERDES receive circuitry 254 may use fast on/off techniques that allow the PLL to power down and conserve power when the ultrasound device is not generating data, and power up to full operating within an acceptably fast period of time when the ultrasound device begins to generate data again. For further description of fast on/off techniques, see Wei, Da, et al., "A 10-Gb/s/ch, 0.6-pJ/bit/mm Power Scalable Rapid-ON/OFF Transceiver for On-Chip Energy Proportional Interconnects," IEEE Journal of Solid-State Circuits 53.3 (2018): 873-883. In some embodiments, implementing the third device in an advanced technology node (e.g., 90 nm, 80 nm, 65 nm, 55 nm, 45 nm, 40 nm, 32 nm, 28 nm, 22 nm, 20 nm, 16 nm, 14 nm, 10 nm, 7 nm, 5 nm, 3 nm, etc.) may facilitate the SERDES receive circuitry 254 operating at a high data rate (e.g., 2-5 gigabits/second).

The digital processing circuitry 276 may include, for example, one or more digital filters, digital beamforming circuitry, digital quadrature demodulation (DQDM) circuitry, averaging circuitry, digital dechirp circuitry, digital time delay circuitry, digital phase shifter circuitry, digital summing circuitry, digital multiplying circuitry, requantization circuitry, waveform removal circuitry, image formation circuitry, backend processing circuitry and/or one or more output buffers. The image formation circuitry in the digital processing circuitry 276 may be configured to perform apodization, back projection and/or fast hierarchy back projection, interpolation range migration (e.g., Stolt interpolation) or other Fourier resampling techniques, dynamic focusing techniques, delay and sum techniques, tomographic reconstruction techniques, doppler calculation, frequency and spatial compounding, and/or low and high-pass filtering, etc.

The second device 204 additionally includes power circuitry 248, communication circuitry 222, clocking circuitry 224, control circuitry 226, and sequencing circuitry 228. The communication circuitry 222 in the second device 204 may be configured to provide communication between the second device 204 and the third device 206 over the communication link 270 (or more than one communication links 270). The communication link 270 may be, for example, one or more traces on a PCB that electrically connect the second device 204 to the third device 206. The communication circuitry 222 may facilitate communication of signals from any circuitry on the second device 204 to the third device 206 and/or communication of signals from any circuitry on the third device 206 to the second device 204 (aside from communication facilitated by the SERDES transmit circuitry 252, the communication links 250, and the SERDES receive circuitry 254).

The clocking circuitry 224 in the second device 204 may be configured to generate some or all of the clocks used in the second device 204 and/or the third device 206. In some embodiments, the clocking circuitry 224 may receive a high-speed clock (e.g., a 1.5625 GHz or a 2.5 GHz clock) from an external source that the clocking circuitry 224 may feed to various circuit components of the ultrasound device 200. In some embodiments, the clocking circuitry 224 may divide and/or multiply the received high-speed clock to produce clocks of different frequencies (e.g., 20 MHz, 40 MHz, 100 MHz, or 200 MHz) that the clocking circuitry 224 may feed to various components of the ultrasound device 200. In some embodiments, the clocking circuitry 224 may separately receive two or more clocks of different frequencies, such as the frequencies described above.

The control circuitry 226 in the second device 204 may be configured to control various circuit components in the second device 204. For example, the control circuitry 226 may control and/or parameterize the pulsers 264, the receive switches 262, the analog processing circuitry 210, the ADCs 212, the SERDES transmit circuitry 252, the power circuitry 248, the communication circuitry 222, the clocking circuitry 224, the sequencing circuitry 228, digital waveform generators, delay meshes, and/or time-gain compensation circuitry (the latter three of which are not shown in FIG. 2). The control circuitry 226 may also be configured to control any circuitry on the third device 206.

The sequencing circuitry 228 in the second device 204 may be configured to coordinate various circuit components on the second device 204 that may or may not be digitally parameterized. In some embodiments, the sequencing circuitry 228 may control the timing and ordering of parameter changes in the second device 204 and/or the third device 206, control triggering of transmit and receive events, and control data flow (e.g., from the second device 204 to the third device 206). In some embodiments, the sequencing circuitry 228 may control execution of an imaging sequence which may be specific to the selected imaging mode, preset, and user settings. In some embodiments, the sequencing circuitry 228 in the second device 204 may be configured as a master sequencer that triggers events on sequencing circuitry 236 in the third device 206 that is configured as a slave sequencer and has been digitally parameterized. In some embodiments, the sequencing circuitry 236 in the third device 206 is configured as a master sequencer that triggers events on the sequencing circuitry 228 in the second device 204 that is configured as a slave sequencer and has been digitally parameterized. In some embodiments, the sequencing circuitry 228 in the second device 204 is configured to control parameterized circuit components on both the second device 204 and the third device 206. In some embodiments, the sequencing circuitry 228 in the second device 204 and the sequencing circuitry 236 in the third device 206 may operate in synchronization by using a clock derived from the same source (e.g., provided by the clocking circuitry).

The power circuitry 248 in the second device 204 may include low dropout regulators, switching power supplies, and/or DC-DC converters to supply the first device 202, the second device 204, and/or the third device 206. In some embodiments, the power circuitry 248 may include multi-level pulsers and/or charge recycling circuitry. For further description of multi-level pulsers and charge recycling circuitry, see U.S. Pat. No. 9,492,144 titled "MULTI-LEVEL PULSER AND RELATED APPARATUS AND METHODS," granted on Nov. 15, 2016, and U.S. patent application Ser. No. 15/087,914 titled "MULTILEVEL BIPOLAR PULSER," issued as U.S. Pat. No. 10,082,565, each of which is assigned to the assignee of the instant application which is incorporated by reference herein in its entirety.

The third device 206 additionally includes communication circuitry 230, clocking circuitry 232, control circuitry 234, sequencing circuitry 236, peripheral management circuitry 238, memory 240, power circuitry 272, processing circuitry 256, and monitoring circuitry 274. The communication circuitry 230 in the third device 206 may be configured to provide communication between the third device 206 and the second device 204 over the communication link 270 (or more than one communication links 270). The communication circuitry 230 may facilitate communication of signals from any circuitry on the third device 206 to the second device 204 and/or communication of signals from any circuitry on the second device 204 to the third device 206.

The clocking circuitry 232 in the third device 206 may be configured to generate some or all of the clocks used in the third device 206 and/or the second device 204. In some embodiments, the clocking circuitry 232 may receive a high-speed clock (e.g., a 1.5625 GHz or a 2.5 GHz clock) that the clocking circuitry 232 may feed to various circuit components of the ultrasound device 200. In some embodiments, the clocking circuitry 232 may divide and/or multiply the received high-speed clock to produce clocks of different frequencies (e.g., 20 MHz, 40 MHz, 100 MHz, or 200 MHz) that the clocking circuitry 232 may feed to various components. In some embodiments, the clocking circuitry 232 may separately receive two or more clocks of different frequencies, such as the frequencies described above.

The control circuitry 234 in the third device 206 may be configured to control various circuit components in the third device 206. For example, the control circuitry 234 may control and/or parameterize the SERDES receive circuitry 254, the digital processing circuitry 276, the communication circuitry 230, the clocking circuitry 232, the sequencing circuitry 236, the peripheral management circuitry 238, the memory 240, the power circuitry 272, and the processing circuitry 256. The control circuitry 234 may also be configured to control any circuitry on the second device 204.

The sequencing circuitry 236 in the third device 206 may be configured to coordinate various circuit components on the third device 206 that may or may not be digitally parameterized. In some embodiments, the sequencing circuitry 236 in the third device 206 is configured as a master sequencer that triggers events on the sequencing circuitry 228 in the second device 204 that has been digitally parameterized. In some embodiments, the sequencing circuitry 228 in the second device 204 is configured as a master sequencer that triggers events on the sequencing circuitry 236 in the second device 204 that is configured as a slave sequencer and has been digitally parameterized. In some embodiments, the sequencing circuitry 236 in the third device 206 is configured to control parameterized circuit components on both the second device 204 and the third device 206. In some embodiments, the sequencing circuitry 236 in the third device 206 and the sequencing circuitry 228 in the second device 204 may operate in synchronization by using a clock derived from the same source (e.g., provided by the clocking circuitry).

The peripheral management circuitry 238 may be configured to generate a high-speed serial output data stream. For example, the peripheral management circuitry 238 may be a Universal Serial Bus (USB) 2.0, 3.0, or 3.1 module. The peripheral management circuitry 238 may additionally or alternatively be configured to allow an external microprocessor to control various circuit components of the ultrasound device 200 over a USB connection. As another example, the peripheral management circuitry 238 may include a WiFi module or a module for controlling another type of peripheral. In some embodiments, this high-speed serial output data stream may be outputted to an external device.

The memory 240 may be configured to buffer and/or store digitized image data (e.g., image data produced by imaging formation circuitry and/or other circuitry in the digital processing circuitry 276). For example, the memory 240 may be configured to enable the ultrasound device 200 to retrieve image data in the absence of a wireless connection to a remote server storing the image data. Furthermore, when a wireless connection to a remote server is available, the memory 240 may also be configured to provide support for wireless connectivity conditions such as lossy channels, intermittent connectivity, and lower data rates, for example. In addition to storing digitized image data, the memory 240 may also be configured to store timing and control parameters for synchronizing and coordinating operation of elements in the ultrasound device 200.

The power circuitry 272 may include power supply amplifiers for supplying power to the third device 206.

The processing circuitry 256, which may be in the form of one or more embedded processors, may be configured to perform processing functions. In some embodiments, the processing circuitry 256 may be configured to perform sequencing functions, either for the second device 204 or for the third device 206. For example, the processing circuitry 256 may control the timing and ordering of parameter changes in the second device 204 and/or the third device 206, control triggering of transmit and receive events, and/or control data flow (e.g., from the second device 204 to the third device 206). In some embodiments, the processing circuitry 256 may control execution of an imaging sequence which may be specific to the selected imaging mode, preset, and user settings. In some embodiments, the processing circuitry 256 may perform external system control, such as controlling the peripheral management circuitry 238, the processing circuitry 256, controlling power sequencing (e.g., for the power circuitry 248 and/or the power circuitry 272), and interfacing with the monitoring circuitry 274. In some embodiments, the processing circuitry 256 may perform internal system control, such as configuring data flow within the chip (e.g., from the second device 204 to the third device 206), calculating or controlling the calculation of processing and image formation parameters (e.g., for image formation circuitry), controlling on chip clocking (e.g., for the clocking circuitry 224 and/or the clocking circuitry 232), and/or controlling power (e.g., for the power circuitry 248 and/or the power circuitry 272). The processing circuitry 256 may be configured to perform functions described above as being performed by other components of the ultrasound device 200, and in some embodiments certain components described herein may be absent if their functions are performed by the processing circuitry 256.

The monitoring circuitry 274 may include, but is not limited to, temperature monitoring circuitry (e.g., thermistors), power measurement circuitry (e.g., voltage and current sensors), nine-axis motion circuitry (e.g., gyroscopes, accelerometers, compasses), battery monitoring circuitry (e.g., coulomb counters), and/or circuitry checking for status or exception conditions of other on-board circuits (e.g., power controllers, protection circuitry, etc.).

It should be understood that there may be many more instances of each component shown in FIG. 2. For example, there may be hundreds, thousands, or tens of thousands of ultrasonic transducers 260, pulsers 264, receive switches 262, analog processing circuitry 210 blocks, SERDES transmit circuitry 252 blocks, SERDES receive circuitry 254 blocks, and/or digital processing circuitry 276 blocks. Additionally, it should be understood that certain components shown in FIG. 2 may receive signals from more components than shown or transmit signals to more components than shown (e.g., in a multiplexed fashion, or after averaging). For example, a given pulser 264 may output signals to one or more ultrasonic transducers 260, a given receive switch 262 may receive signals from one or more ultrasonic transducers 260, a given block of analog processing circuitry 210 may receive signals from one or more receive switches 262, a given ADC 212 may receive signals from one or more blocks of analog processing circuitry 210, a given block of SERDES transmit circuitry 252 may receive signals from one or more ADCs 212. In some embodiments, a given ultrasound element may have an ultrasonic transducer 260 and a dedicated pulser 264, receive switch 262, analog processing circuitry 210 block, ADC 212, and/or SERDES transmit circuitry 252 block. It should also be understood that certain embodiments of an ultrasound device may have more or fewer components than shown in FIG. 2.

For further description of the circuit components of the ultrasound device 200, see U.S. Pat. No. 9,521,991 titled "MONOLITHIC ULTRASONIC IMAGING DEVICES, SYSTEMS, AND METHODS," granted on Dec. 20, 2016 (and assigned to the assignee of the instant application), which is incorporated by reference herein in its entirety.

Figure 3:
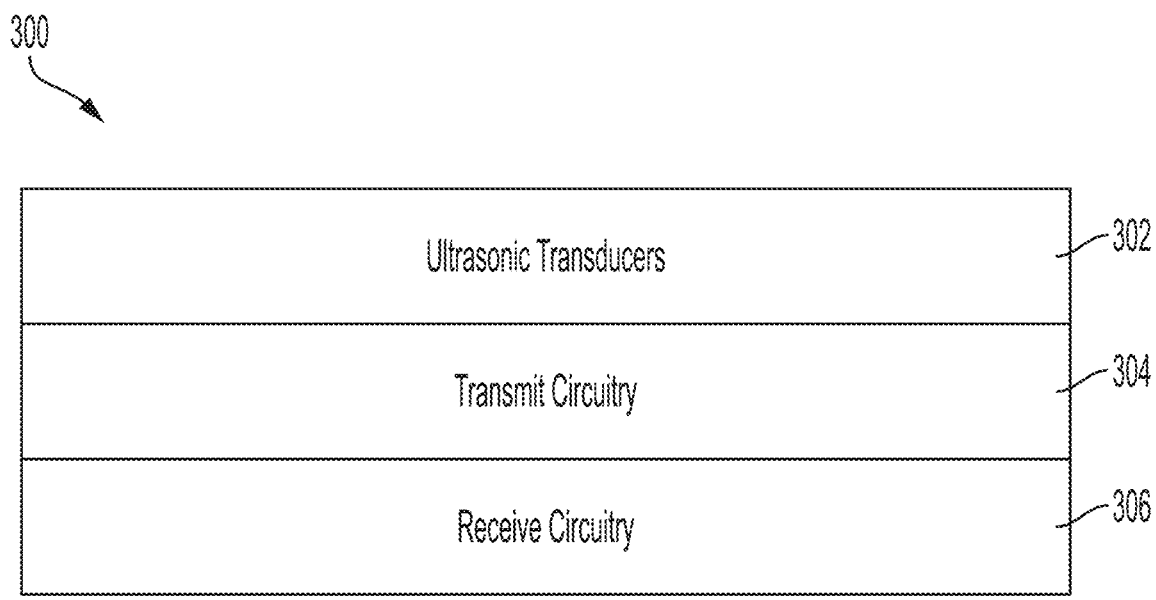
FIG. 3 illustrates a block diagram of another ultrasound device in accordance with certain embodiments described herein.

FIG. 3 illustrates a block diagram of an ultrasound device 300 in accordance with certain embodiments described herein. The ultrasound device includes a first device 302, a second device 304, and a third device 306. The first device 302, the second device 304, and the third device 306 may be, for example, dies (e.g., application-specific integrated circuits (ASICs)) or wafers that are diced, and each device may include multiple layers of materials (e.g., silicon, oxides, metals, etc.). The bottom surface of the first device 302 is bonded to the top surface of the second device 304. The bottom surface of the second device 304 is bonded to the top surface of the third device 306. The bonding between the first device 302 and the second device 304 and the bonding between the second device 304 and the third device 306 may include, for example, thermal compression (also referred to herein as "thermocompression"), eutectic bonding, silicide bonding (which is a bond formed by bringing silicon of one substrate into contact with metal on a second substrate under sufficient pressure and temperature to form a metal silicide, creating a mechanical and electrical bond), or solder bonding.

The ultrasound device 300 is configured to drive ultrasonic transducers to emit pulsed ultrasonic signals into a subject, such as a patient. The pulsed ultrasonic signals may be back-scattered from structures in the body, such as blood cells or muscular tissue, to produce echoes that return to the ultrasonic transducers. These echoes may then be converted into electrical signals by the transducer elements. The electrical signals representing the received echoes are then converted into ultrasound data.

The first device 302 includes the ultrasonic transducers. Example ultrasonic transducers include capacitive micromachined ultrasonic transducers (CMUTs), CMOS ultrasonic transducers (CUTs), and piezoelectric micromachined ultrasonic transducers (PMUTs). For example, CMUTs and CUTs may include cavities formed in a substrate with a membrane/membranes overlying the cavity. The ultrasonic transducers may be arranged in an array (e.g., one-dimensional or two-dimensional). The second device 304 includes integrated transmit circuitry, which may include one or more pulsers configured to receive waveforms from one or more waveform generators and output driving signals corresponding to the waveforms to the ultrasonic transducers. The third device includes integrated receive circuitry, which may include one or more analog amplifiers, one or more analog filters, analog beamforming circuitry, analog dechirp circuitry, analog quadrature demodulation (AQDM) circuitry, analog time delay circuitry, analog phase shifter circuitry, analog summing circuitry, analog time gain compensation circuitry, analog averaging circuitry, analog-to-digital converters, digital filters, digital beamforming circuitry, digital quadrature demodulation (DQDM) circuitry, averaging circuitry, digital dechirp circuitry, digital time delay circuitry, digital phase shifter circuitry, digital summing circuitry, digital multiplying circuitry, requantization circuitry, waveform removal circuitry, image formation circuitry, backend processing circuitry, and/or one or more output buffers.

The second device 304 may be implemented in a different technology node than the third device 306 is, and the technology node of the third device 306 may be a more advanced (smaller) technology node with smaller feature sizes than the technology node in which the second device 304 is implemented. For example, the technology node of the second device 304 may be a technology node that provides circuit devices (e.g., transistors) capable of operating at voltages in the range of approximately 80-200 V, such as 80 V, 90 V, 100 V, 200 V, or >200 V. In some embodiments, the technology node of the second device 304 may be a technology node that provides circuit devices (e.g., transistors) capable of operating at other voltages, such as voltages in the range of approximately 5-30 V or voltages in the range of approximately 30-80V. By operating at such voltages, circuitry in the second device 304 may be able to drive the ultrasonic transducers in the first device 302 to emit acoustic waves having acceptably high pressures. The technology node of the second device 304 may be, for example, 65 nm, 80 nm, 90 nm, 110 nm, 130 nm, 150 nm, 180 nm, 220 nm, 240 nm, 250 nm, 280 nm, 350 nm, 500 nm, >500 nm, or any other suitable technology node.

The technology node of the third device 306, for example, may be one that provides circuit device (e.g., transistors) capable of operation at a voltage in the range of approximately 0.45-0.9V, such as 0.9V, 0.85V, 0.8V, 0.75V, 0.7V, 0.65V, 0.6V, 0.6V, 0.55V, 0.5V, and 0.45V. In some embodiments, the technology node of the third device 306 may be one that provides circuit device capable of operation at a voltage in the range of approximately 1-1.8 V, or approximately 2.5-3.3 V. By operating at such voltages, power consumption of circuitry in the third device 306 may be reduced to an acceptable level. Compared with the ultrasound device 100, including integrated analog receive circuitry in the third device 306 rather than the second device 304 may further reduce power consumption. Additionally, the feature size of devices provided by the technology node may enable an acceptably high degree of integration density of circuitry in the third device 306. The technology node of the third device 306 may be, for example, 90 nm, 80 nm, 65 nm, 55 nm, 45 nm, 40 nm, 32 nm, 28 nm, 22 nm, 20 nm, 16 nm, 14 nm, 10 nm, 7 nm, 5 nm, 3 nm, etc.

Figure 4:
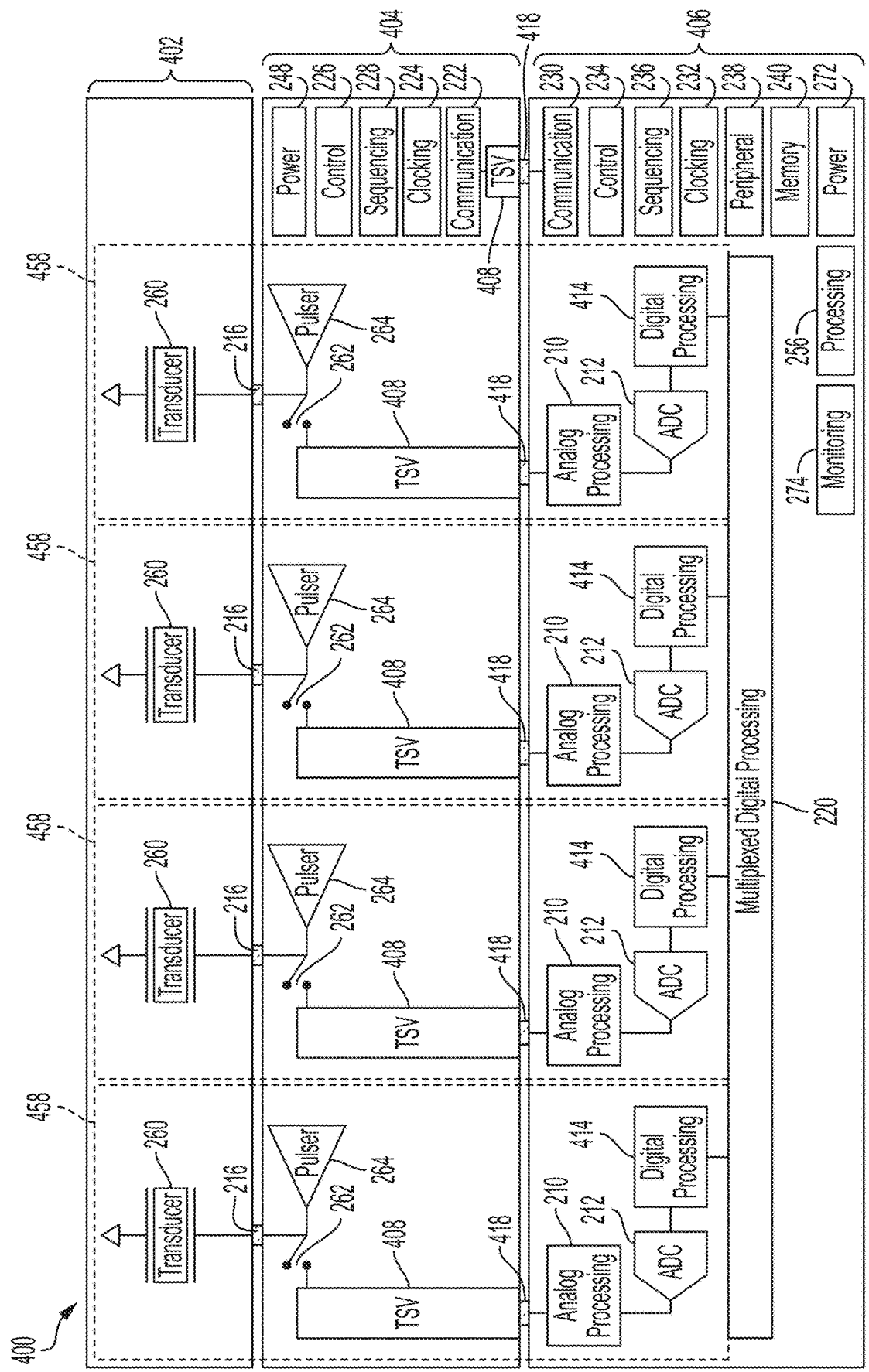
FIG. 4 illustrates a block diagram of another ultrasound device in accordance with certain embodiments described herein.

FIG. 4 illustrates an example block diagram of an ultrasound device 400 in accordance with certain embodiments described herein. The ultrasound device 400 includes a first device 402, a second device 404, and a third device 406. The ultrasound device 400, the first device 402, the second device 404, and the third device 406 may be examples of the ultrasound device 300, the first device 302, the second device 304, and the third device 306, respectively, illustrated in more detail. The ultrasound device 400 includes a plurality of elements 458 (which may also be considered pixels). While only four elements 458 are shown in FIG. 4, it should be appreciated that many more elements 458 may be included, such as hundreds, thousands, or tens of thousands of elements. Each of the elements 458 includes an ultrasonic transducer 260, a pulser 264, a receive switch 262, a through-silicon via (TSV) 408, an analog processing circuitry 210 block, an analog-to-digital converter (ADC) 212, and a digital processing circuitry 414 block. The first device 402 includes the ultrasonic transducers 260. The second device 404 includes the pulsers 264, the receive switches 262, and the TSVs 408. The third device 406 includes the analog processing circuitry 210, the ADCs 212, the digital processing circuitry 414, and multiplexed digital processing circuitry 220. Bonding points 216 electrically connect the ultrasonic transducers 260 in the first device 402 to the pulsers 264 and the receive switches 262 in the second device 404. Bonding points 418 electrically connect the TSVs 408 in the second device 404 to the analog processing circuitry 210 in the third device 406.

Further description of the ultrasonic transducers 260, the pulsers 264, and the receive switches 262 may be found with reference to FIG. 2. In contrast to the ultrasonic device 200, when the ultrasonic transducer 260 is receiving the echoes (the "receive phase"), the ultrasonic transducer 260 may transmit the electrical signals representing the received echoes to the analog processing circuitry 210 through the bonding point 216, the receive switch 262, the TSV 408, and the bonding point 418.

The TSV 408 is a via that passes through the second device 404 and facilitates transmission of the electrical signals representing the received echoes from the ultrasonic transducer 260 in the first device 402, through the second device 404, and to the analog processing circuitry 210 in the third device 406 along a low-resistance path. Because the electrical signals representing the received echoes may be relatively weak (e.g., on the order of millivolts or microvolts), it may be especially desirable to transmit the electrical signals along a low-resistance path to avoid attenuation. The TSV 408 may be helpful in transmitting these relatively weak signals through the second device 404 with acceptably low attenuation. Additionally, the TSV 408 may be helpful in transmitting these signals with low parasitic capacitance which may increase signal-to-noise ratio and bandwidth.

Further description of the analog processing circuitry 210 and the ADC 212 may be found with reference to FIG. 2. The digital output of the ADC 212 is sent to the digital processing circuitry 414. The digital processing circuitry 414 may include, for example, one or more digital filters, digital beamforming circuitry, digital quadrature demodulation (DQDM) circuitry, averaging circuitry, digital dechirp circuitry, digital time delay circuitry, digital phase shifter circuitry, digital summing circuitry, digital multiplying circuitry, and/or an output buffer. The digital output of each digital processing circuitry 414 from each element 458 is sent to the multiplexed digital processing circuitry 220, which processes the digital output from each element 458 in a multiplexed fashion. The multiplexed digital processing circuitry 220 may include a combination of, for example, requantization circuitry, waveform removal circuitry, image formation circuitry, and backend processing circuitry. The image formation circuitry in the digital processing circuitry 414 may be configured to perform apodization, back projection and/or fast hierarchy back projection, interpolation range migration (e.g., Stolt interpolation) or other Fourier resampling techniques, dynamic focusing techniques, and/or delay and sum techniques, tomographic reconstruction techniques, etc.

The second device 404 additionally includes power circuitry 248, communication circuitry 222, clocking circuitry 224, control circuitry 226, and/or sequencing circuitry 228. The third device 406 additionally includes communication circuitry 230, clocking circuitry 232, control circuitry 234, sequencing circuitry 236, peripheral management circuitry 238, memory 240, power circuitry 272, processing circuitry 256, and monitoring circuitry 274. The communication circuitry 222 may communicate with the communication circuitry 230 through a TSV 408 and a bonding point 418. Further description of these components may be found with reference to FIG. 2.

As can be seen in FIG. 4, for a given element 458, a single ultrasonic transducer 260 in the first device 402 is electrically connected to a single TSV 408 in the second device 404, and the single TSV 408 is electrically connected to a single pulser 264 in the second device 404 and to a single receive circuitry block (i.e., a single analog processing circuitry 210, ADC 212, and digital processing circuitry 414) in the third device 406. This in-situ, element-matched electrical connection between the first device 402, the second device 404, and the third device 406 facilitates tight integration between the three devices in order to pass the weak analog electrical signals from the first device 402, through the second device 404, and to the third device 406 without unacceptable attenuation. In some embodiments, multiple TSVs 408 and bonding points 418 may be multiplexed to a single receive circuitry block (i.e., a single analog processing circuitry 210, ADC 212, and digital processing circuitry 414). The signals transmitted through the TSVs 408 may each be connected to the receive circuitry block, one after another.

It should be appreciated from FIG. 4 that in some embodiments, there may be one TSV 408 per ultrasonic transducer. Additionally, it should be appreciated from FIG. 4 that in some embodiments, there may be one TSV 408 per pulser 264. In some embodiments, there may be one TSV 408 per instance of transmit circuitry. For example, one TSV 408 may be multiplexed to multiple pulsers 264.

It should be understood that there may be many more instances of each component shown in FIG. 4. For example, there may be hundreds, thousands, or tens of thousands of ultrasonic transducers 260, pulsers 264, receive switches 262, analog processing circuitry 210 blocks, digital processing circuitry 414 blocks, and multiplexed digital processing 220 blocks. Additionally, it should be understood that certain components shown in FIG. 4 may receive signals from more components than shown or transmit signals to more components than shown (e.g., in a multiplexed fashion, or after averaging). For example, a given pulser 264 may output signals to one or more ultrasonic transducers 260, a given receive switch 262 may receive signals from one or more ultrasonic transducers 260, a given TSV 408 may receive signals from one or more receive switches 262, a given block of analog processing circuitry 210 may receive signals from one or more TSVs 408, a given ADC 212 may receive signals from one or more blocks of analog processing circuitry 210, and a given block of digital processing circuitry 414 may receive signals from one or more ADCs 212. It should also be understood that certain embodiments of an ultrasound device may have more or fewer components than shown in FIG. 4.

Figure 5:
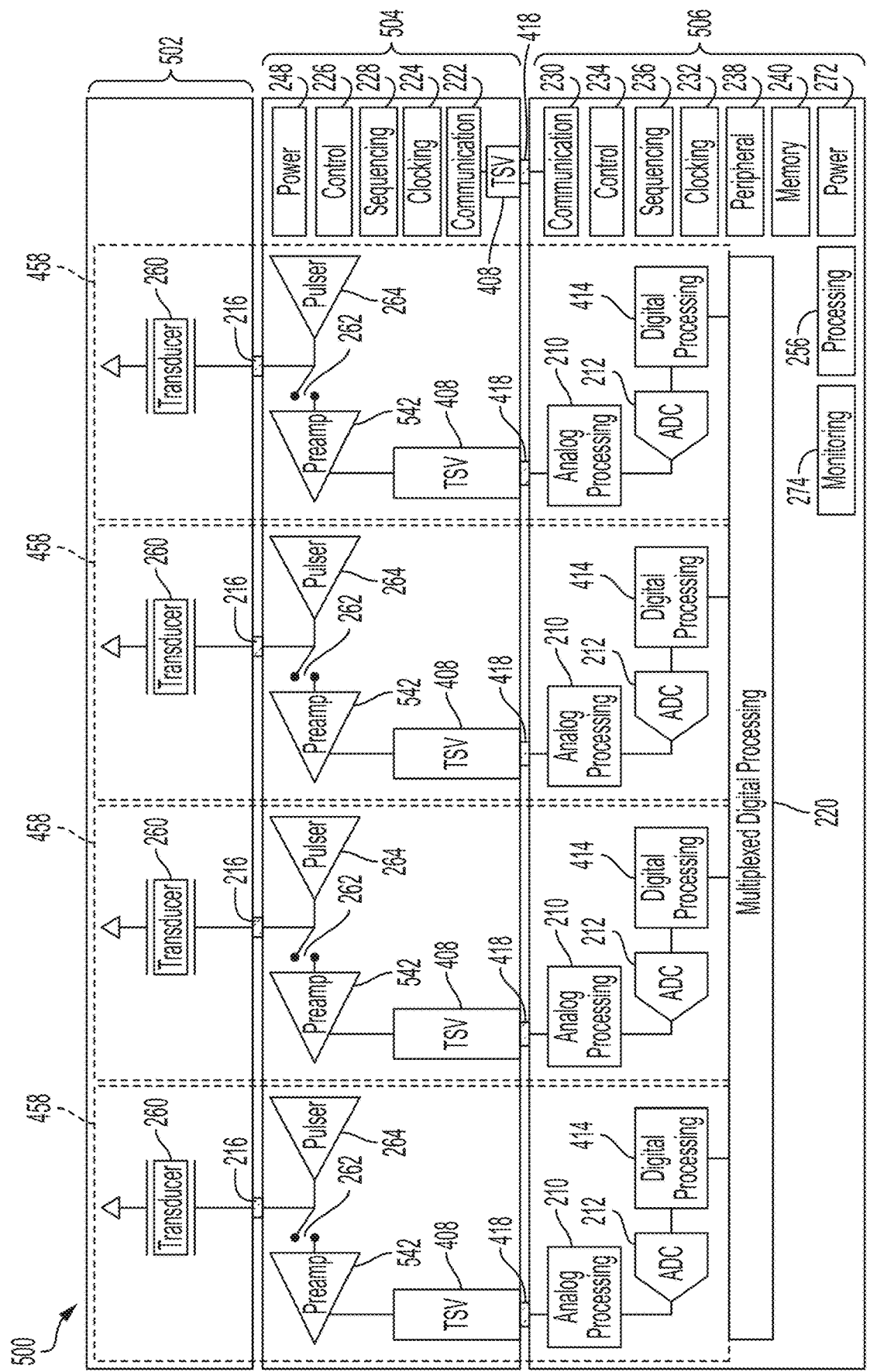
FIG. 5 illustrates a block diagram of another ultrasound device in accordance with certain embodiments described herein.

FIG. 5 illustrates an example block diagram of an ultrasound device 500 in accordance with certain embodiments described herein. The ultrasound device 500 includes a first device 502, a second device 504, and a third device 506. The ultrasound device 500, the first device 502, the second device 504, and the third device 506 may be examples of the ultrasound device 300, the first device 302, the second device 304, and the third device 306, respectively, illustrated in more detail. The ultrasound device 500 differs from the ultrasound device 400 in that the ultrasound device 500 includes a preamplifier 542 between the receive switch 262 and the TSV 408.

Figure 6:
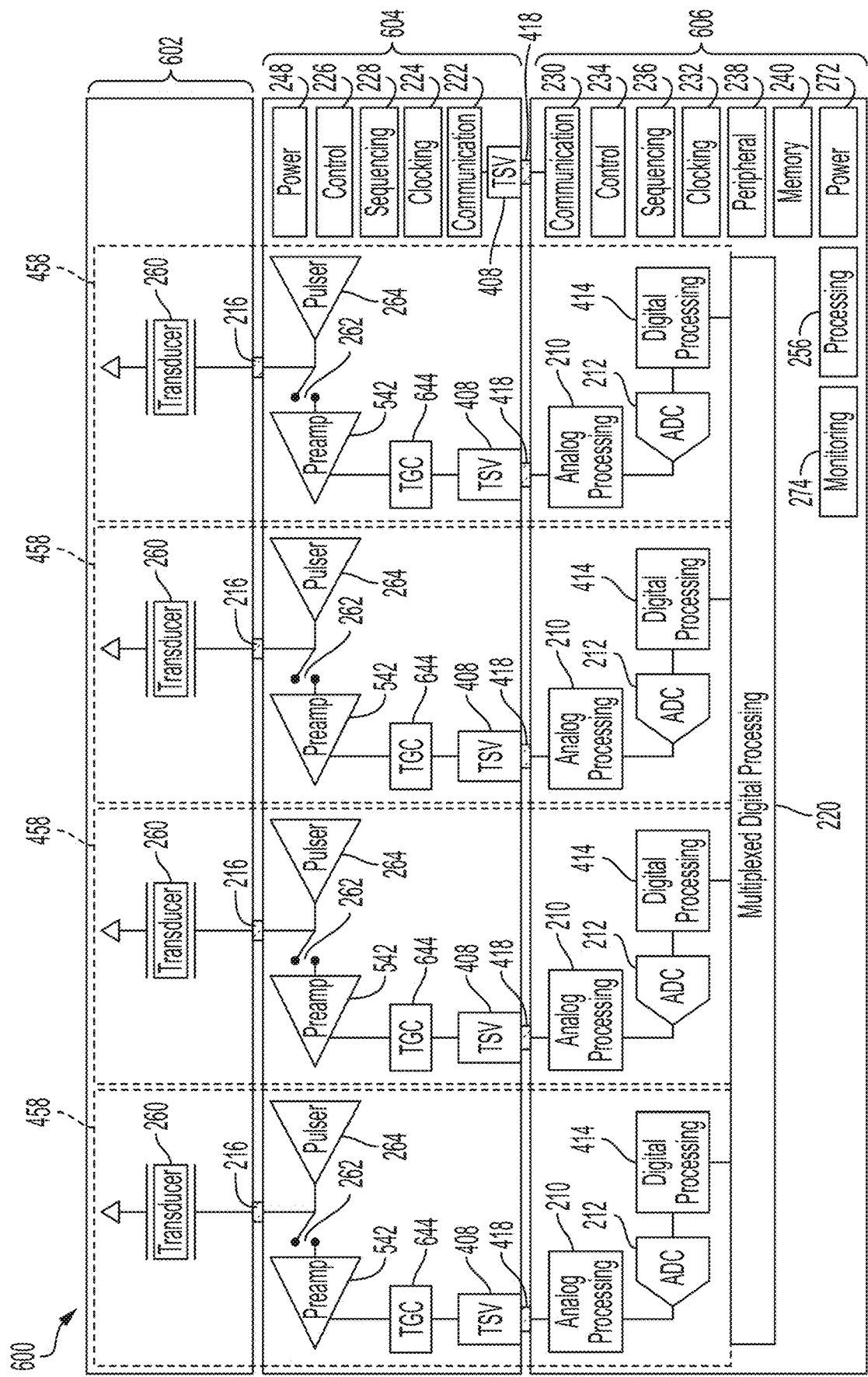
FIG. 6 illustrates a block diagram of another ultrasound device in accordance with certain embodiments described herein.

FIG. 6 illustrates an example block diagram of an ultrasound device 600 in accordance with certain embodiments described herein. The ultrasound device 600 includes a first device 602, a second device 604, and a third device 606. The ultrasound device 600, the first device 602, the second device 604, and the third device 606 may be examples of the ultrasound device 300, the first device 302, the second device 304, and the third device 306, respectively, illustrated in more detail. The ultrasound device 600 differs from the ultrasound device 500 in that ultrasound device 600 includes time-gain compensation (TGC) circuitry 644 between the preamplifier 542 and the TSV 408.

Figure 7:
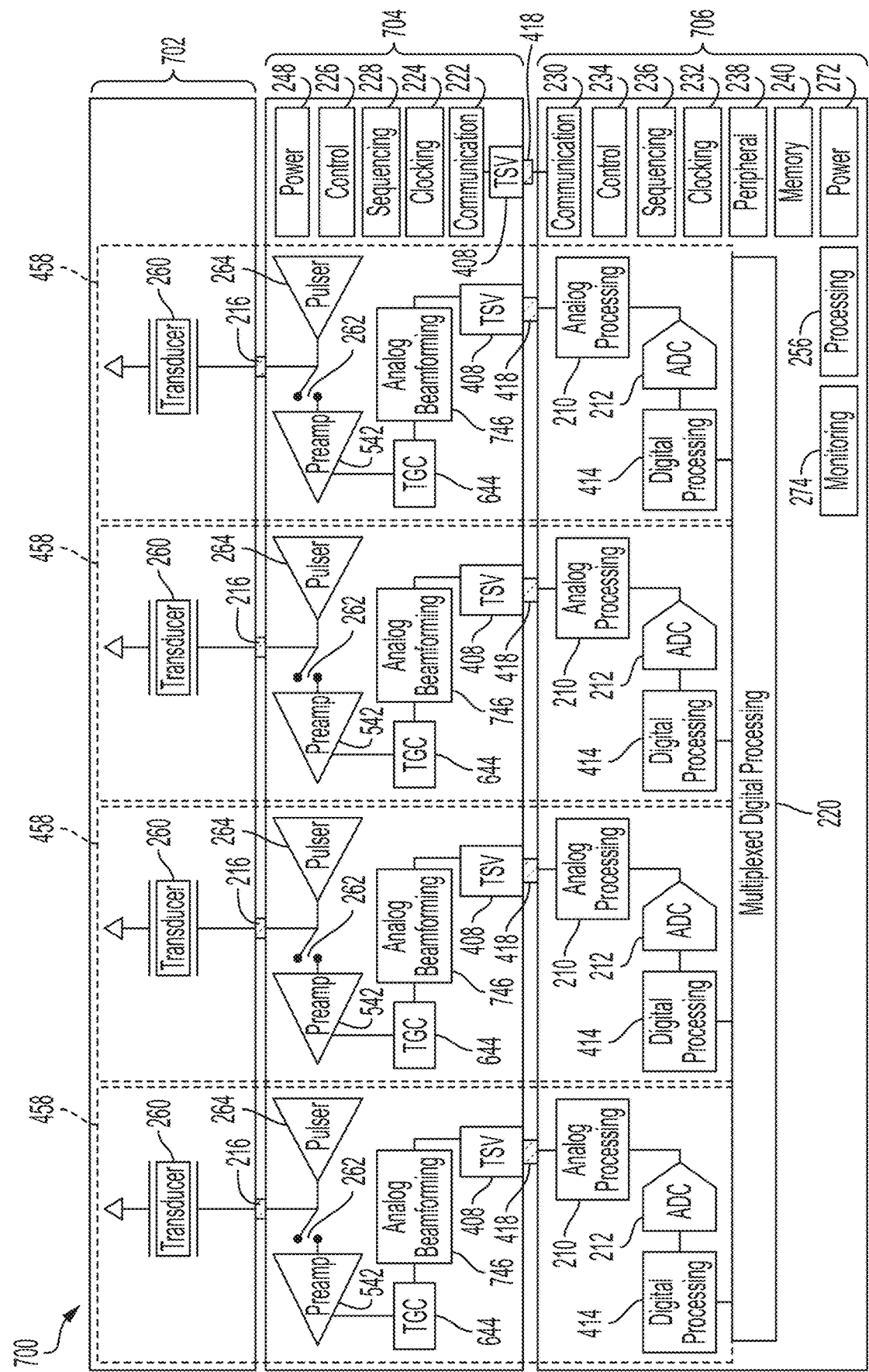
FIG. 7 illustrates a block diagram of another ultrasound device in accordance with certain embodiments described herein.

FIG. 7 illustrates an example block diagram of an ultrasound device 700 in accordance with certain embodiments described herein. The ultrasound device 700 includes a first device 702, a second device 704, and a third device 706. The ultrasound device 700, the first device 702, the second device 704, and the third device 706 may be examples of the ultrasound device 300, the first device 302, the second device 304, and the third device 306, respectively, illustrated in more detail. The ultrasound device 700 differs from the ultrasound device 600 in that the ultrasound device 700 includes analog beamforming circuitry 746 between the TGC circuitry 644 and the TSV 408.

Figure 8:
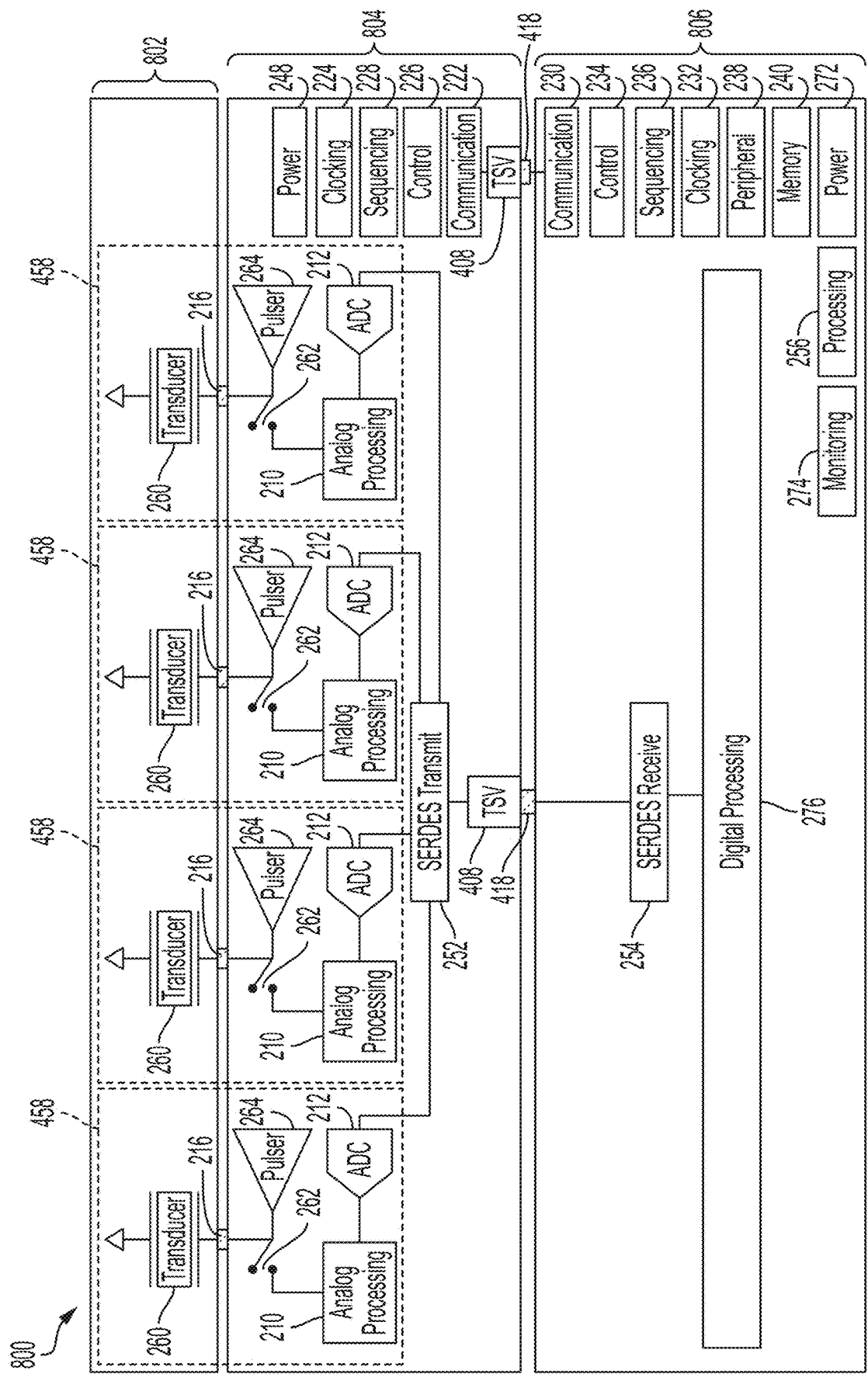
FIG. 8 illustrates a block diagram of another ultrasound device in accordance with certain embodiments described herein.

FIG. 8 illustrates an example block diagram of an ultrasound device 800 in accordance with certain embodiments described herein. The ultrasound device 800 includes a first device 802, a second device 804, and a third device 806. The ultrasound device 800 can be considered a hybrid of the ultrasound device 200 and the ultrasound device 400. Like the ultrasound device 200, in the ultrasound device 800, the second device 804 includes the pulsers 264, the receive switches 262, the analog processing circuitry 210, the ADCs 212, and the SERDES transmit circuitry 252, and the third device 806 includes SERDES receive circuitry 254 and digital processing circuitry 220. Like the ultrasound device 400, the third device 806 is bonded to the second device 804 at the bonding points 418 and the TSVs 408 facilitate transmission of electrical signals from the second device 804 to the third device 806. In particular, the TSV 408 facilitates transmission of electrical signals from the SERDES transmit circuitry 252 to the SERDES receive circuitry 254. The ultrasound device 800 can thus be considered a three-device stacked version of the ultrasound device 200, where communication between the second device 804 and the third device 806 occurs over the TSV's 408, and the communication occurs at high-speed due to the SERDES transmit circuitry 252 and the SERDES receive circuitry 254.

In the ultrasound device 800, one block of SERDES transmit circuitry 252 receives data from multiple ADC's 212 and is electrically coupled, through a TSV 408 and a bonding point to 418, to one block of SERDES receive circuitry 254 that is coupled to the digital processing circuitry 276. There may be multiple instances of SERDES transmit circuitry 252, TSV 408, bonding point 418, and SERDES receive circuitry 254, each receiving data from multiple ADC's 212. In some embodiments, there may be one instance of SERDES transmit circuitry 252, TSV 408, bonding point 418, and SERDES receive circuitry 254 per ADC 212 and/or per ultrasonic transducer 260, or more generally, per element 458.

It should be appreciated that in some embodiments, any of the ultrasound devices 200, 400, 500, 600, 700, and 800 may incorporate combinations of features shown with reference to other ultrasound devices. For example, the ultrasound device 400 may include the time-gain compensation circuitry 644 between the receive switch 262 and the TSV 408 but not the preamplifier 542. As another example, the ultrasound device 400 may include the time-gain compensation circuitry 644 and the analog beamforming circuitry 746 between the receive switch 262 and the TSV 408 but not the preamplifier 542. As another example, the ultrasound device 400 may include the preamplifier 542 and the analog beamforming circuitry 746 between the receive switch 262 and the TSV 408 but not the time-gain compensation circuitry 542. As another example, the ultrasound device 800 may include any of the preamplifier 542, the time-gain compensation circuitry 644, and/or the analog beamforming circuitry 746. It should also be understood that certain embodiments may have more or fewer components than shown in the figures.

Figure 9:
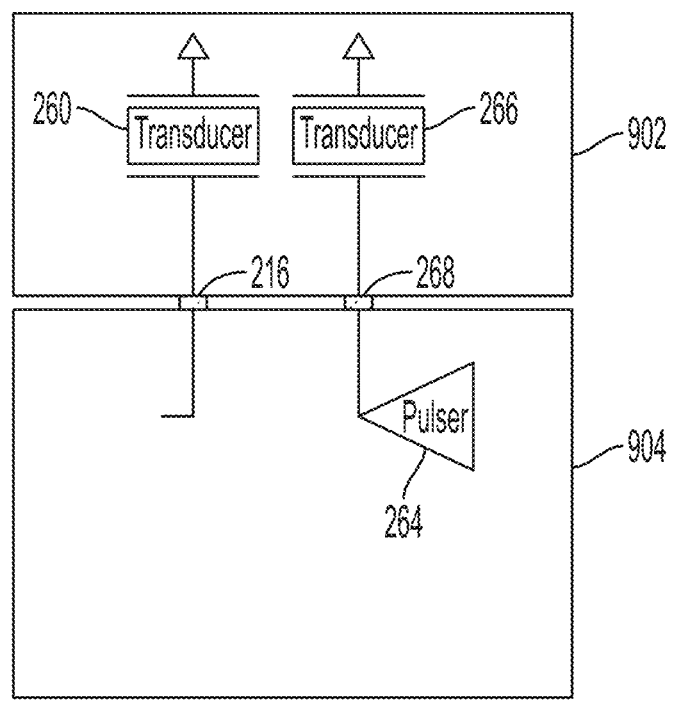
FIG. 9 illustrates a paradigm for an ultrasound device, in accordance with certain embodiments described herein.

FIG. 9 illustrates a paradigm for an ultrasound device, in accordance with certain embodiments described herein. FIG. 9 show portions of a first device 902 and a second device 904, or portions thereof. The first device 902 includes an ultrasonic transducer 266 and an ultrasonic transducer 260. The second device 904 includes a pulser 264, a bonding point 268, and a bonding point 216. In FIG. 9, the pulser 264 is configured to output a driving signal to the ultrasonic transducer 266 through the bonding point 268 during the transmit phase. The bonding point 268 electrically connects the ultrasonic transducer 266 in the first device 902 to the pulser 264 in the second device 304. The ultrasonic transducer 266 may be configured to emit pulsed ultrasonic signals into a patient and the ultrasonic transducer 260 may be configured to convert the received echoes into electrical signals during the receive phase and transmit the electrical signals representing the received echoes to the second device 904 through the bonding point 216. In FIG. 9, the bonding point 216 electrically connects the ultrasonic transducer 260 in the first device 902 to the second device 904. Because the ultrasonic transducer 266 performs transmit operations and the ultrasonic transducer 260 performs receive operations, the receive switch 262 is not needed. Any of the embodiments of the ultrasound devices 200, 400, 500, 600, 700, or 800 may incorporate the paradigm of FIG. 9 that includes two ultrasonic transducers 260 and 266, two bonding points 216 and 268, and no receive switch 262. The circuitry in the second device 904 to which the bonding point 216 is connected may depend on the ultrasound device (e.g., the TSV 408 in the ultrasound device 400; the preamplifier 542 in the ultrasound devices 500, 600, and 700; or the analog processing circuitry 210 in the ultrasound devices 200 and 800).

FIGS. 10-32 illustrate example cross-sections of the ultrasound device 300 during a fabrication sequence for forming the ultrasound device 300 in accordance with certain embodiments described herein. It will be appreciated that the fabrication sequence shown is not limiting, and some embodiments may include additional steps and/or omit certain shown steps. As shown in FIG. 10, the first device 302 begins as a silicon-on-insulator (SOI) wafer 1000 that includes a handle layer 1002 (e.g., a silicon handle layer), a buried oxide (BOX) layer 1004, and a silicon device layer 1108. An oxide layer 1005 is provided on the backside of the handle layer 1002, but may be optional in some embodiments.

The silicon device layer 1108 may be formed of single crystal silicon and may be doped in some embodiments. In some embodiments, the silicon device layer 1108 may be highly doped P-type, although N-type doping may alternatively be used. When doping is used, the doping may be uniform or may be patterned (e.g., by implanting in patterned regions). The silicon device layer 1108 may already be doped when the SOI wafer 1000 is procured, or may be doped by ion implantation, as the manner of doping is not limiting. In some embodiments, the silicon device layer 1108 may be formed of polysilicon or amorphous silicon. In either case the silicon device layer 1108 may be doped or undoped.

As shown in FIG. 11, an oxide layer 1112 is formed on the SOI wafer 1000. The oxide layer 1112 is used to at least partially define the cavity/cavities of the ultrasonic transducers, and thus may have any suitable thickness to provide for a desired cavity depth. The oxide layer 1112 may be a thermal silicon oxide, but it should be appreciated that oxides other than thermal oxide may alternatively be used.

As shown in FIG. 12, the oxide layer 1112 is patterned to form a cavity 1106, using any suitable technique (e.g., using a suitable etch). In this non-limiting embodiment, the cavity 1106 extends to the surface of the silicon device layer 1108, although in alternative embodiments the cavity 1106 may not extend to the surface of the silicon device layer 1108. In some embodiments, the oxide layer 1112 may be etched to the surface of the silicon device layer 1108 and then an additional layer of oxide (e.g., thermal silicon oxide) may be formed such that the cavity 1106 is defined by a layer of oxide. In some embodiments, the cavity 1106 may extend into the silicon device layer 1108. Also, in some embodiments structures such as isolation posts can be formed within the cavity 1106.

Any suitable number and configuration of cavities 1106 may be formed, as the aspects of the application are not limited in this respect. Thus, while only one cavity 1106 is illustrated in the non-limiting cross-sectional view of FIG. 12, it should be appreciated that many more may be formed in some embodiments. For example, an array of cavities 1106 may include hundreds of cavities, thousands of cavities, tens of thousands of cavities, or more to form an ultrasonic transducer array of a desired size.

The cavity 1106 may take one of various shapes (viewed from a top side) to provide a desired membrane shape when the ultrasonic transducers are ultimately formed. For example, the cavity 1106 may have a circular contour or a multi-sided contour (e.g., a rectangular contour, a hexagonal contour, an octagonal contour).

Figure 13:
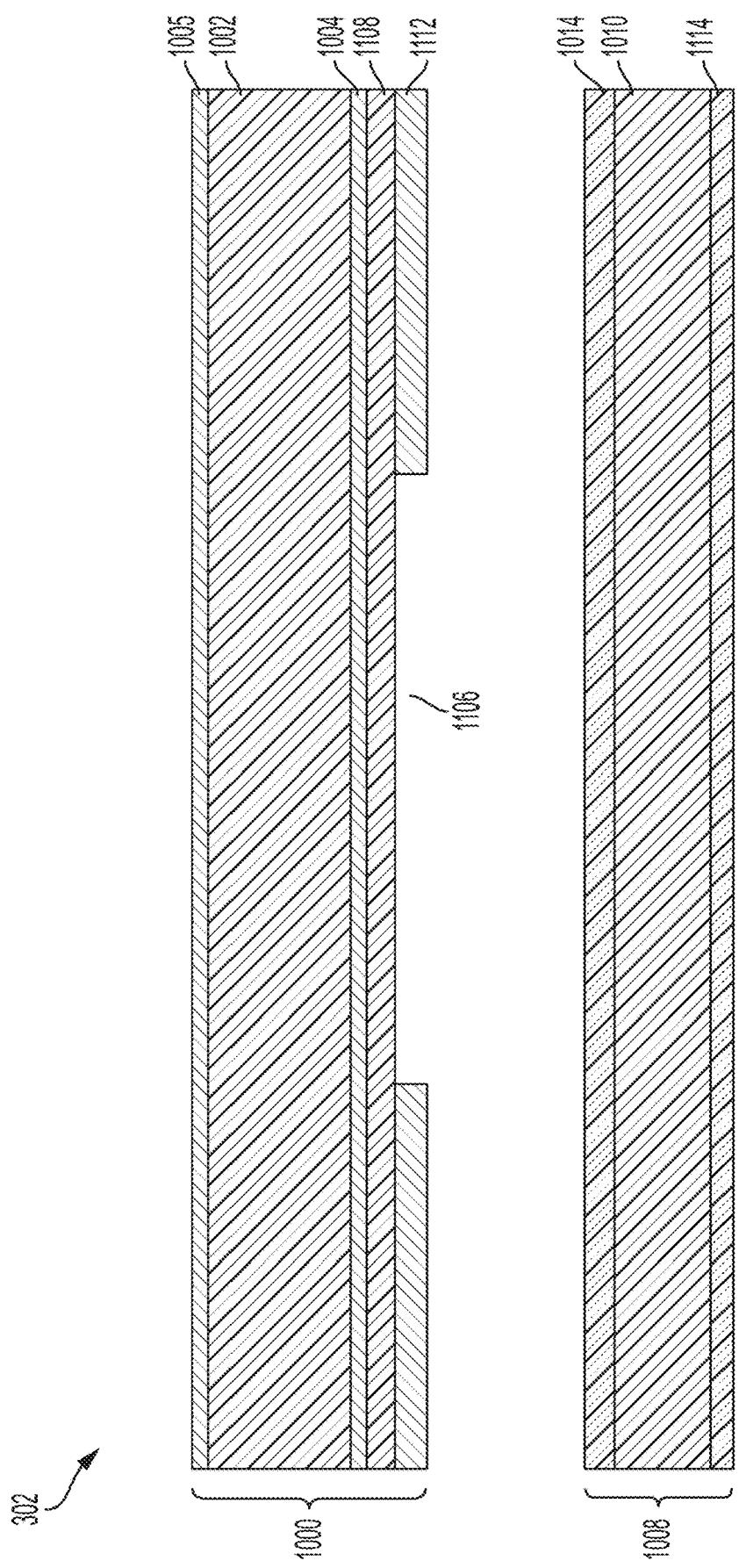

FIG. 13 illustrates the SOI wafer 1000 and a silicon wafer 1008. The silicon wafer 1008 includes a silicon layer 1010, an oxide layer 1114, and an oxide layer 1014.

Figure 14:
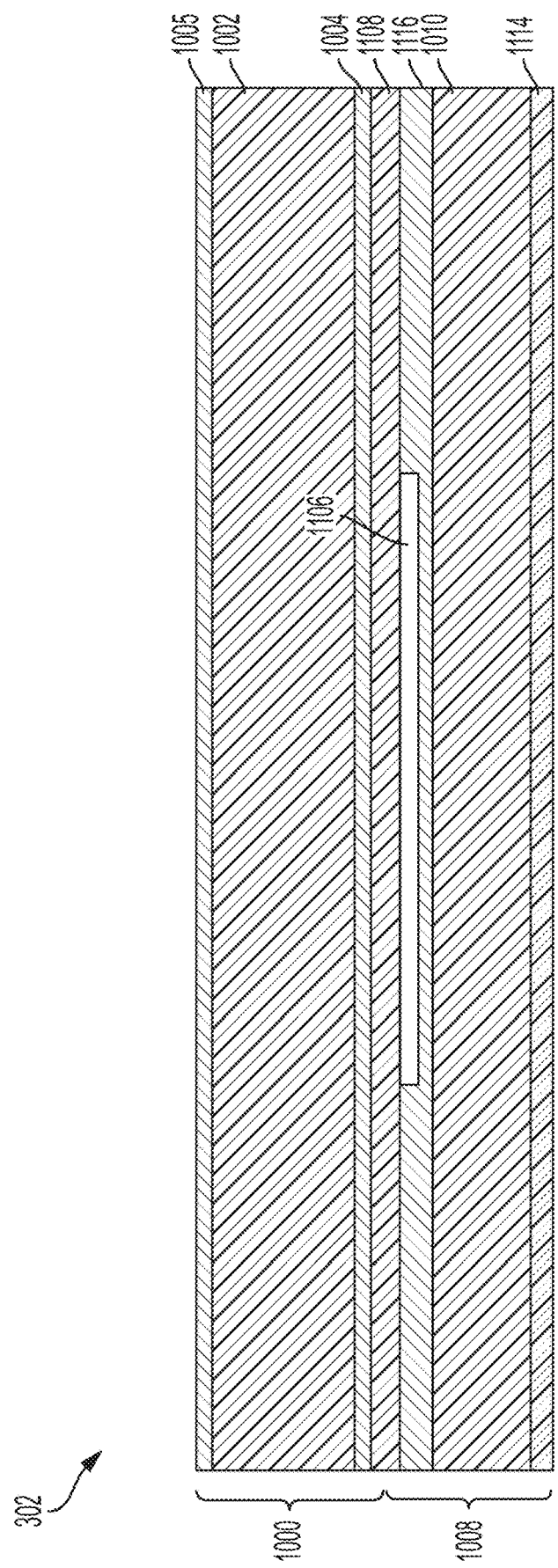

As shown in FIG. 14, the SOI wafer 1000 is bonded to the silicon wafer 1008. The bonding may be performed at a low temperature (e.g., a fusion bond below 450° C.), but may be followed by an anneal at a high temperature (e.g., at greater than 500° C.) to ensure sufficient bond strength. In the embodiment shown, the bond between the SOI wafer 1000 and the silicon wafer 1008 is an $SiO_2$—$SiO_2$ bond between the oxide layer 1112 and the oxide layer 1014. The combination of the oxide layer 1112 and the oxide layer 1014 is shown as oxide layer 1116.

Figure 15:
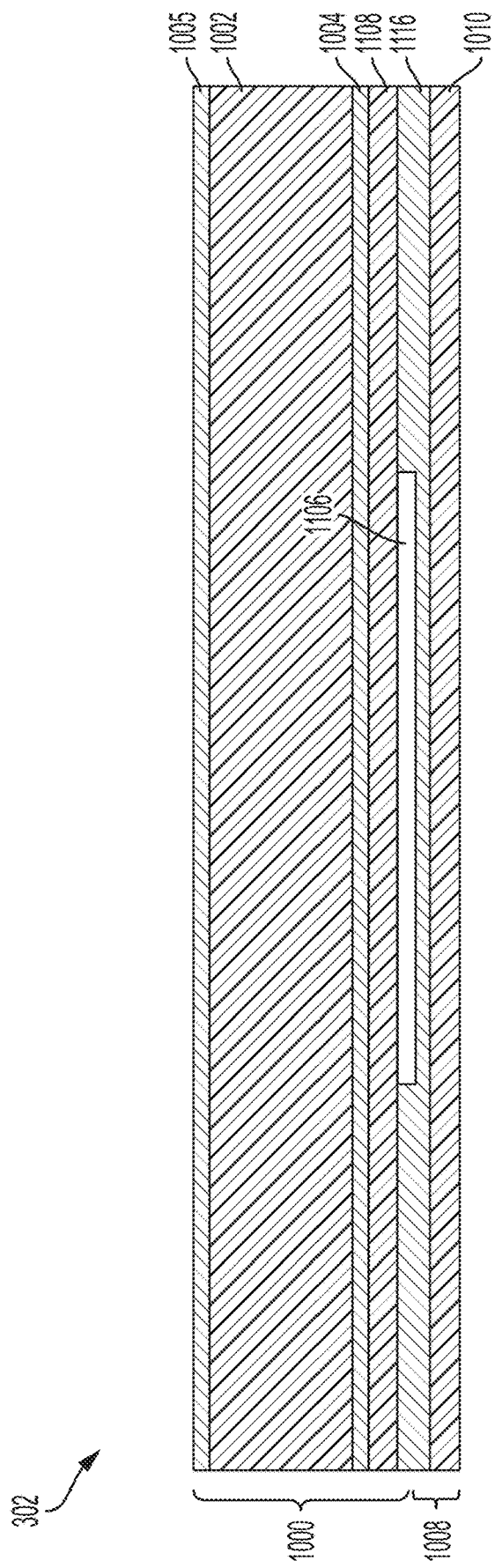

As shown in FIG. 15, the oxide layer 1114 is removed and the silicon layer 1010 is thinned, in any suitable manner. For example, grinding, etching, or any other suitable technique or combination of techniques may be used. As a result, the layers remaining from the silicon wafer 1008 include the silicon layer 1010 and the oxide layer 1014. These layers may be thin (e.g., 40 microns, 30 microns, 20 microns, 10 microns, 5 microns, 2.5 microns, 2 microns, 1 micron, or less, including any range or value within the range less than 40 microns). However, because they are bonded to the SOI wafer 1000 with its corresponding handle layer 1002, sufficient structural integrity may be retained for this processing step and for further processing steps.

Figure 16:
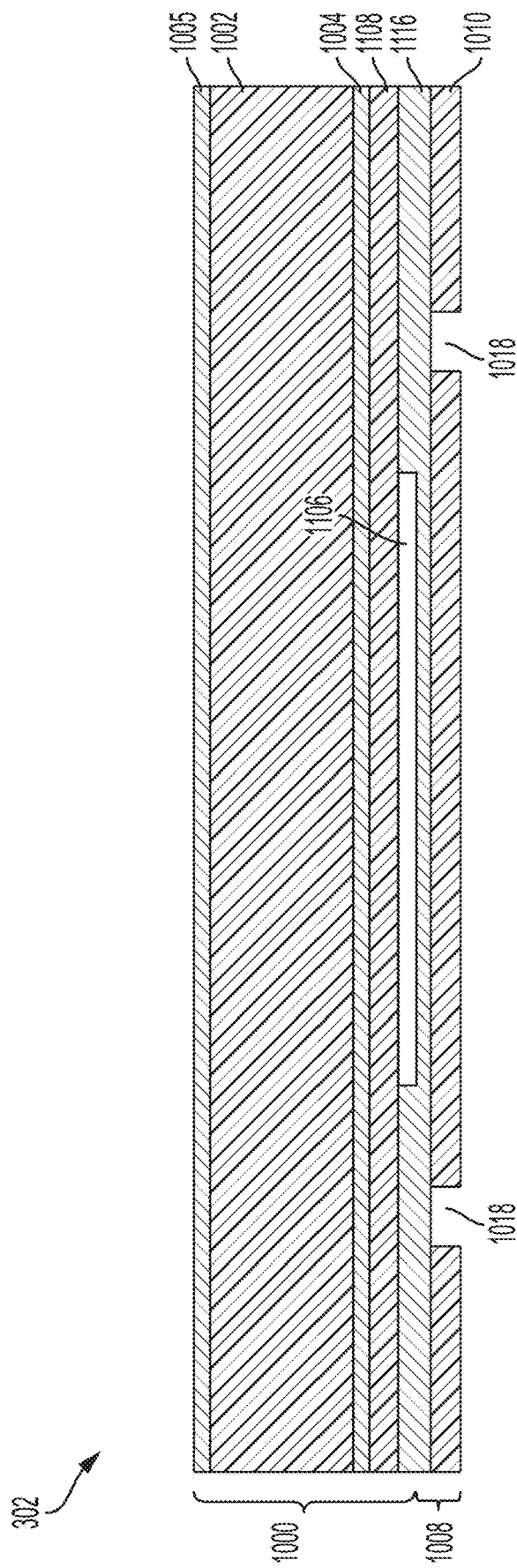

In some embodiments, it may be desirable to electrically isolate one or more ultrasonic transducers of the first device 302. Thus, as shown in FIG. 16, isolation trenches 1018 are formed in the silicon layer 1010. In the illustrated embodiment, the isolation trenches 1018 extend from a backside of the silicon layer 1010 to the oxide layer 1116, and are narrower (in the direction of left to right in the figure) than the portion(s) of the overlying oxide layer 1116 to which each isolation trench 1018 makes contact to prevent inadvertently punching through the oxide layer 1116 into the cavity 1106. Thus, the isolation trenches 1018 do not impact the structural integrity of the cavity 1106. However, alternative configurations are possible.

Figure 17:
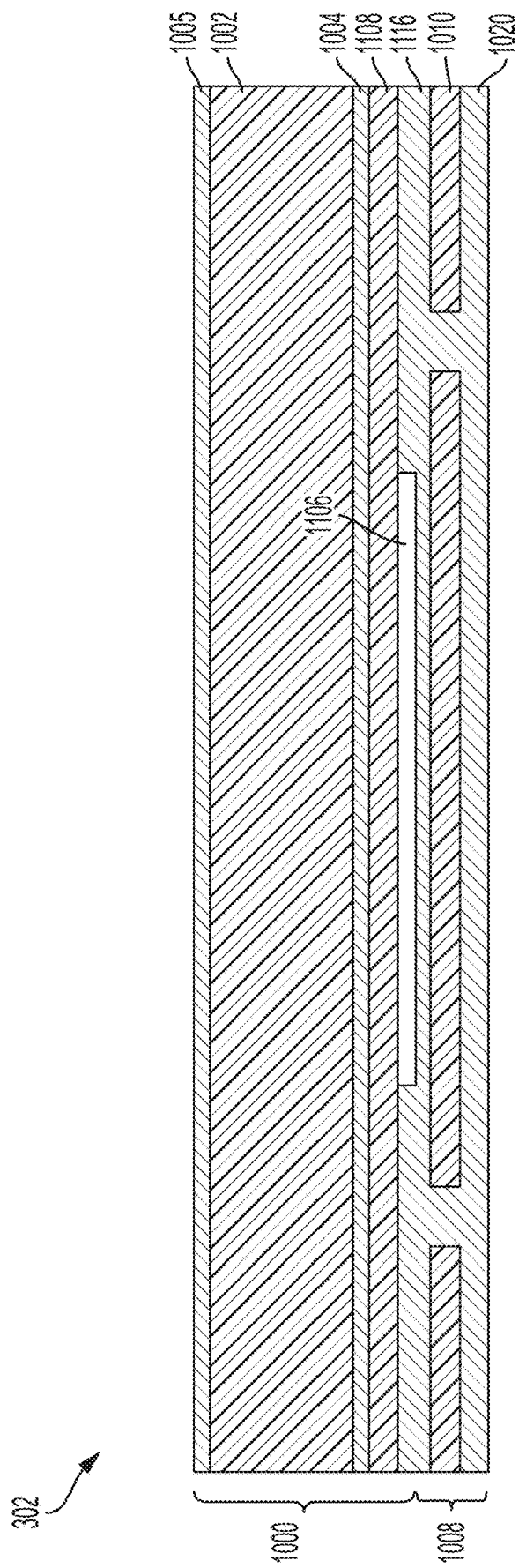

FIG. 17 illustrates that the isolation trenches 1018 are filled with an insulating material 1020 (e.g., thermal silicon oxide in combination with undoped polysilicon) using any suitable technique (e.g., a suitable deposition). It should be noted that in the embodiment illustrated, the insulating material 1020 completely fills the isolation trenches 1018 and does not simply line the isolation trenches 1018, which may further contribute to the structural integrity of the device at this stage, rendering it more suitable for further processing.

Figure 18:
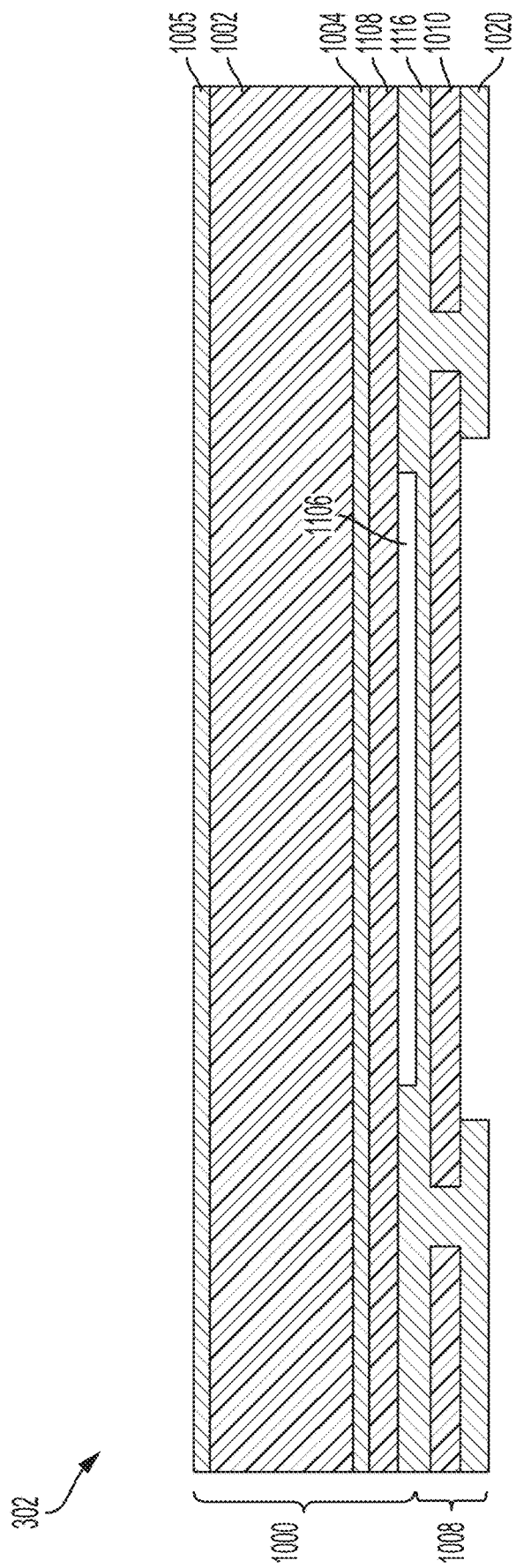

As shown in FIG. 18, the insulating material 1020 is patterned (using any suitable etch technique) in preparation for forming bonding locations for later bonding of the first device 302 with the second device 304.

Figure 19:
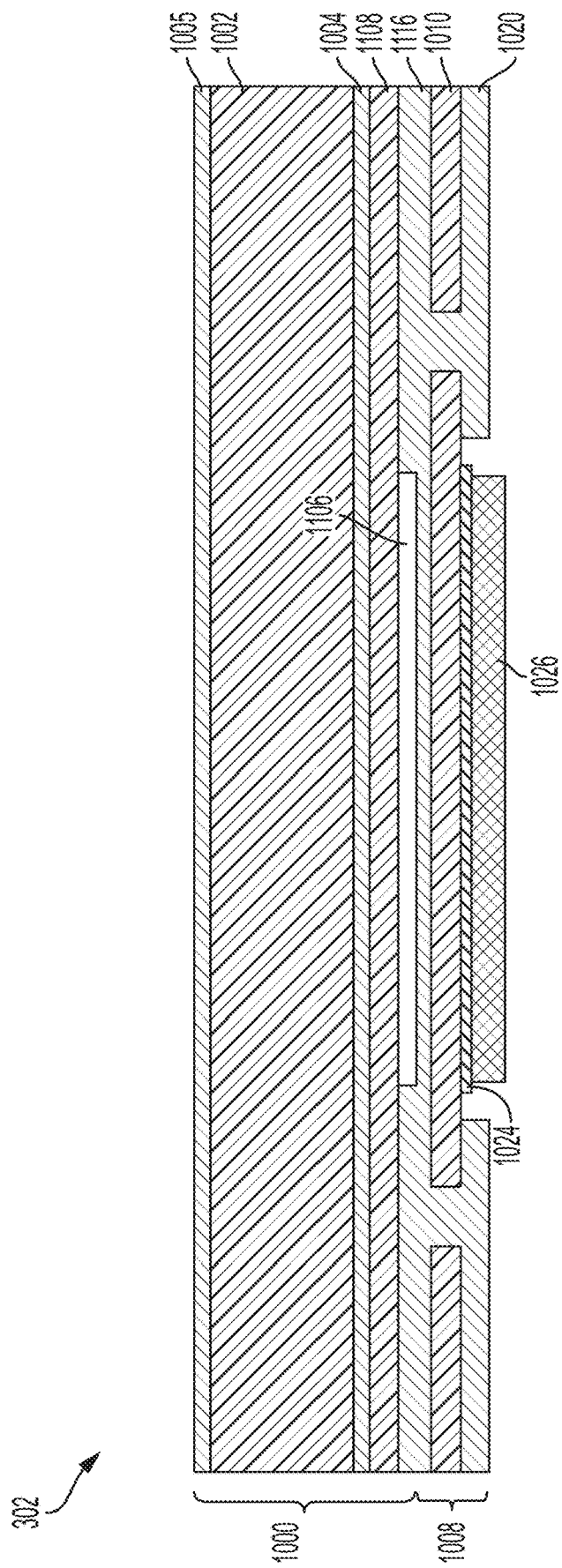

A bonding structure 1026 is then formed on the first device 302 in preparation for bonding the first device 302 with the second device 304, as shown in FIG. 19. The type of material included in the bonding structure 1026 may depend on the type of bond to be formed. For example, the bonding structure 1026 may include a metal suitable for thermocompression bonding, eutectic bonding, or silicide bonding. In some embodiments, the bonding structure 1026 may include a conductive material so that electrical signals may be communicated between the first device 302 and the second device 304. For example, in some embodiments the bonding structure 1026 may include gold and may be formed by electroplating. In some embodiments, materials and techniques used for wafer level packaging may be applied in the context of bonding the first device 302 with the second device 304. Thus, for example, stacks of metals selected to provide desirable adhesion, interdiffusion barrier functionality, and high bonding quality may be used, and the bonding structure 1026 may include such stacks of metals. In FIG. 19, the bonding structure 1026 is shown adhered to an adhesion structure 1024 on the silicon layer 1010.

As shown in FIG. 20, the second device 304 includes a base layer (e.g., a bulk silicon wafer) 1118, an insulating layer 1120, metallization 1122, a via 1124, metallization 1126, a via 1128, and a TSV 408. The via 1124 electrically connects the metallization 1122 to the metallization 1126. The via 1128 electrically connects the metallization 1126 to the TSV 408. An insulating layer 1028 is formed on the backside of the base layer 1118. The metallization 1122 may be formed of aluminum, copper, or any other suitable metallization material, and may represent at least part of an integrated circuit formed in the second device 304. For example, the metallization 1122 and the metallization 1126 may serve as routing layers, may be patterned to form one or more electrodes, or may be used for other functions. In practice, the second device 304 may include more than two metallization layers and/or post-processed redistribution layers, but for simplicity only two metallizations are illustrated. The TSV 408 may be formed of a metal, such as copper, doped polysilicon, or tungsten. The second device 304 may be fabricated at a commercial foundry.

As shown in FIG. 21, layers 1030 and 1032 are formed on the second device 304. The layer 1030 may be, for example, a nitride layer and may be formed by plasma enhanced chemical vapor deposition (PECVD). The layer 1032 may be an oxide layer, for example formed by PECVD of oxide.

In FIG. 22, openings 1034 are formed from the layer 1032 to the metallization 1122. Such openings are made in preparation for forming bonding points.

Figure 23:
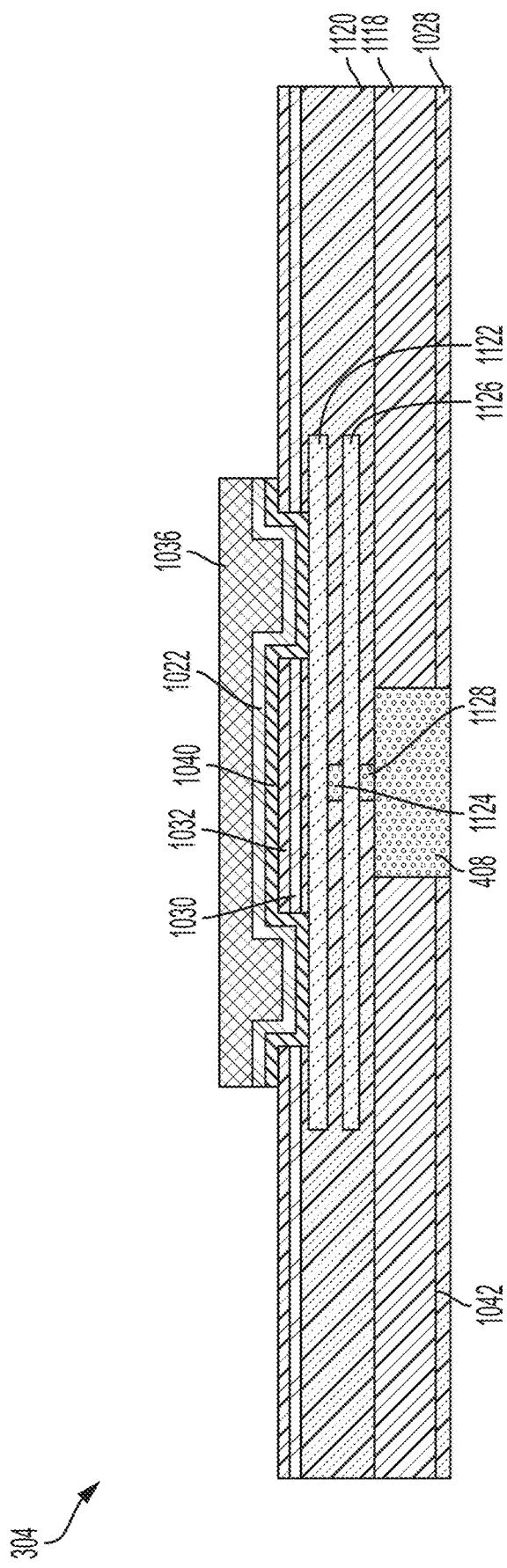

In FIG. 23, a bonding structure 1036 is formed on the second device 304 (by suitable deposition and patterning) at a location for bonding the first device 302 with the second device 304. The bonding structure 1036 is shown adhered to adhesion structures 1040 and 1022. The bonding structure 1036 may include any suitable material for bonding with the bonding structure 1026 on the first device 302. As previously described, in some embodiments a low temperature eutectic bond may be formed, and in such embodiments the bonding structure 1026 and the bonding structure 1036 may form a eutectic pair. For example, the bonding structure 1026 and the bonding structure 1036 may form an indium-tin (In—Sn) eutectic pair, a gold-tin (Au—Sn) eutectic pair, and aluminum-germanium (Al—Ge) eutectic pair, or a tin-silver-copper (Sn—Ag—Cu) combination. In the case of Sn—Ag—Cu, two of the materials may be formed on the first device 302 as the bonding structure 1026 with the remaining material formed as the bonding structure 1036. The bonding structure 1036 (and other bonding structures described herein with similar forms) may not be shown to scale, for example, downward protrusions shown in the bonding structure 1036 may be substantially smaller in height than the height of the rest of the bonding structure 1036.

Figure 24:
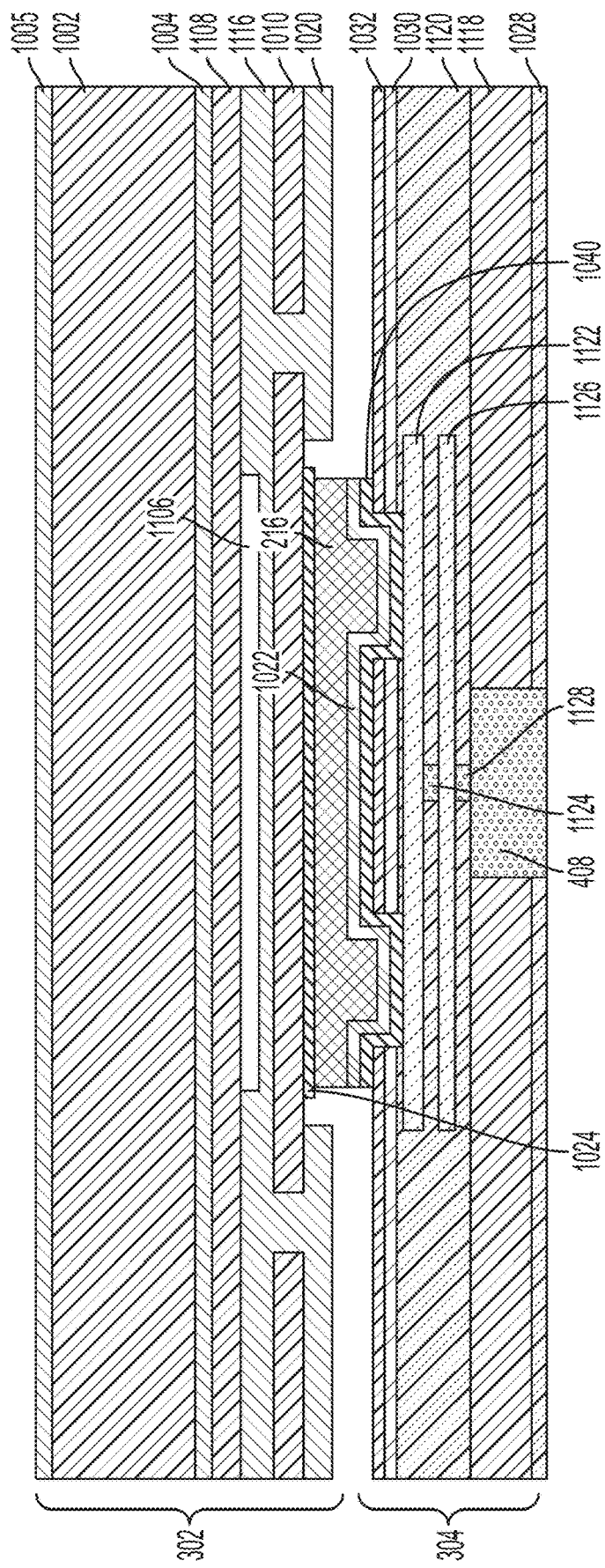

As shown in FIG. 24, the first device 302 and the second device 304 are then bonded together. As previously described, such bonding may, in some embodiments, involve only the use of low temperature (e.g., below 450° C.) which may prevent damage to the metallization 1122, the metallization 1126, and other components on the second device 304.

In the non-limiting example illustrated, the bond is a eutectic bond, such that the bonding structure 1026 and the bonding structure 1036 in combination form the bonding point 216. The bonding point 216 forms an electrical contact between the first device 302 and the second device 304. As a further non-limiting example, a thermocompression bond may be formed using Au as the bonding material. For instance, the bonding structure 1026 may include a seed layer (formed by sputtering or otherwise) of Ti/TiW/Au with plated Au formed thereon, and the bonding structure 1036 may include a seed layer (formed by sputtering or otherwise) of TiW/Au with plated Ni/Au formed thereon. The layers of titanium may serve as adhesion layers. The TiW layers may serve as adhesion layers and diffusion barriers. The nickel may serve as a diffusion barrier. The Au may form the bond. Other bonding materials may alternatively be used.

Figure 25:
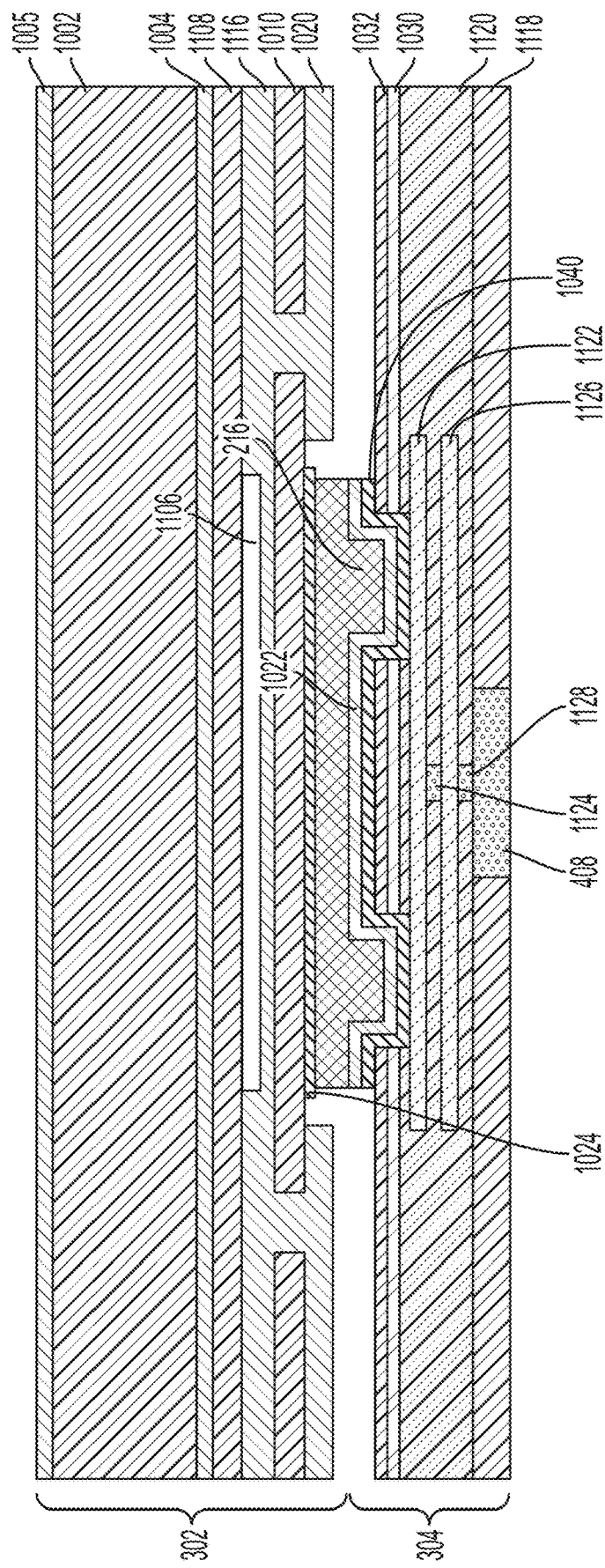

As shown in FIG. 25, the insulating layer 1028 is removed, and the TSV 408 and base layer 1118 are reduced in height. For example, grinding and/or etching may be used. The TSV 408 may be reduced in height to, for example, between approximately 4 microns and approximately 750 microns in height. Reducing the height of the TSV 408 may be helpful in reducing the capacitance of the TSV 408, which can in turn reduce degradation of the bandwidth and noise performance of the TSV 408. Furthermore, if a heat sink is ultimately placed on the backside of the ultrasound device 300, reducing the height of the TSV 408 can reduce the distance of the second device 304 and the first device 302 to the heat sink, which can reduce heating of the ultrasound device 300. Sufficient structural integrity may be provided for this processing step by the handle layer 1002, which has not yet been removed.

In some embodiments, the second device 304 includes a bonding structure that is electrically connected to the TSV 408. For example, the second device 304 may be fabricated by a commercial foundry, and the bonding structure may be fabricated by the foundry in order to provide external electrical connection to the TSV 408 and circuitry and/or routing layers (e.g., the metallization 1122) to which the TSV 408 is electrically connected. In such embodiments, the process may include removing the existing bonding structure in electrical contact with the TSV 408. The bonding structure may include, for example, a material that can be ground in a grinding process, and that may be a different material than the TSV 408. After the second device 304 is thinned, a bonding structure can be reformed to provide external electrical connection to the TSV 408.

Figure 26:
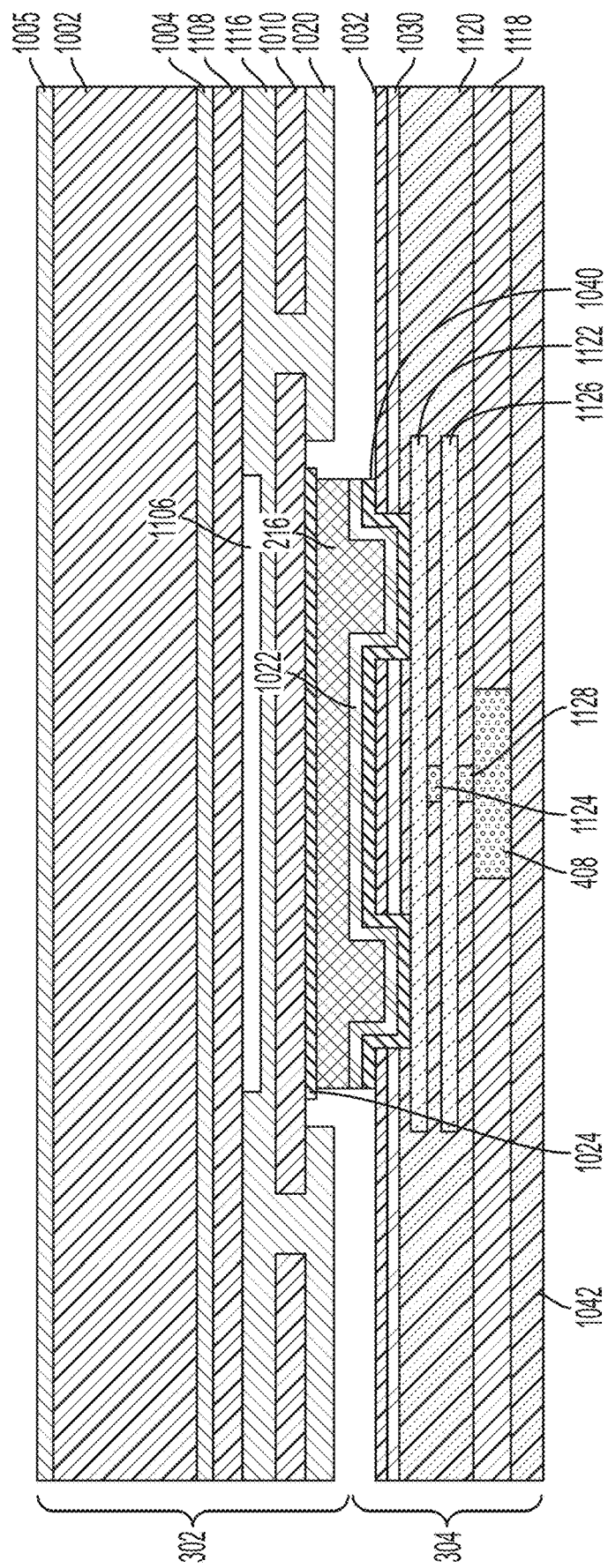

FIG. 26 illustrates that an insulating material 1042 (e.g., silicon oxide) is deposited on the second device 304 using any suitable technique (e.g., a suitable deposition).

Figure 27:
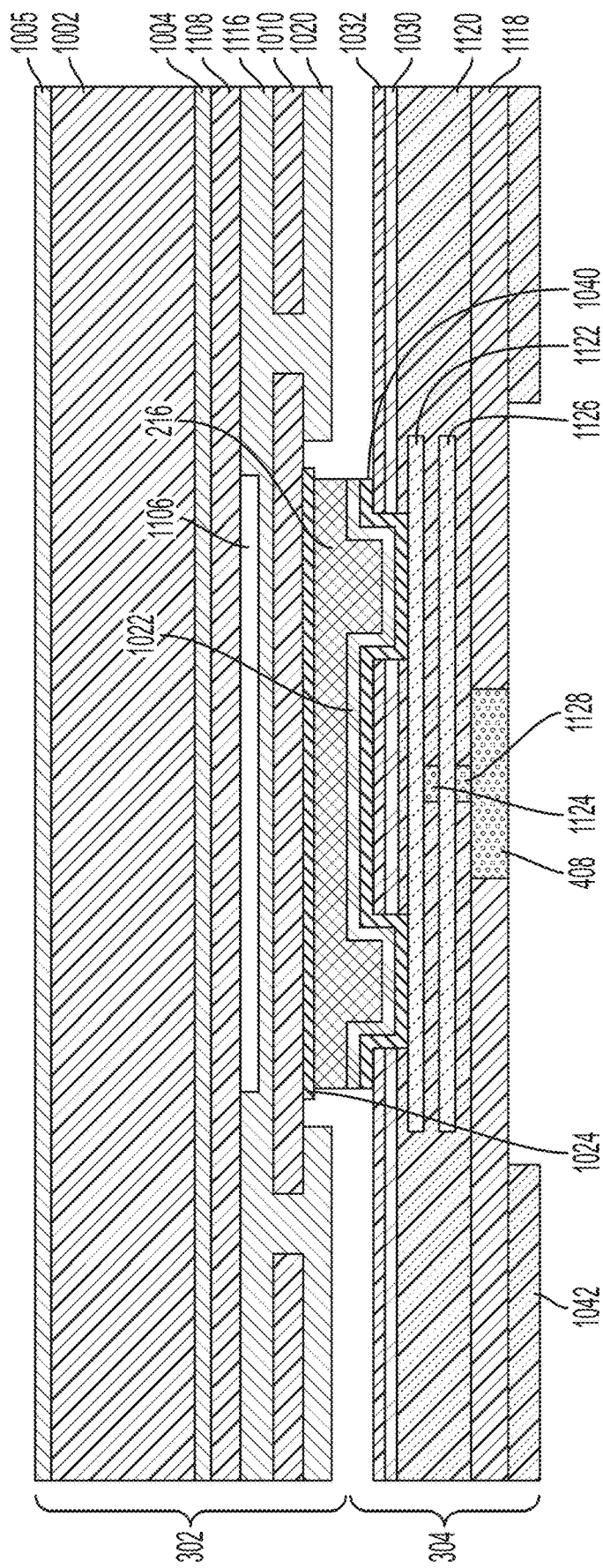

As shown in FIG. 27, the insulating material 1042 is patterned (using any suitable etch technique) in preparation for forming bonding locations for later bonding of the second device 304 with the third device 306, similar to as described in relation to FIG. 18.

Figure 28:
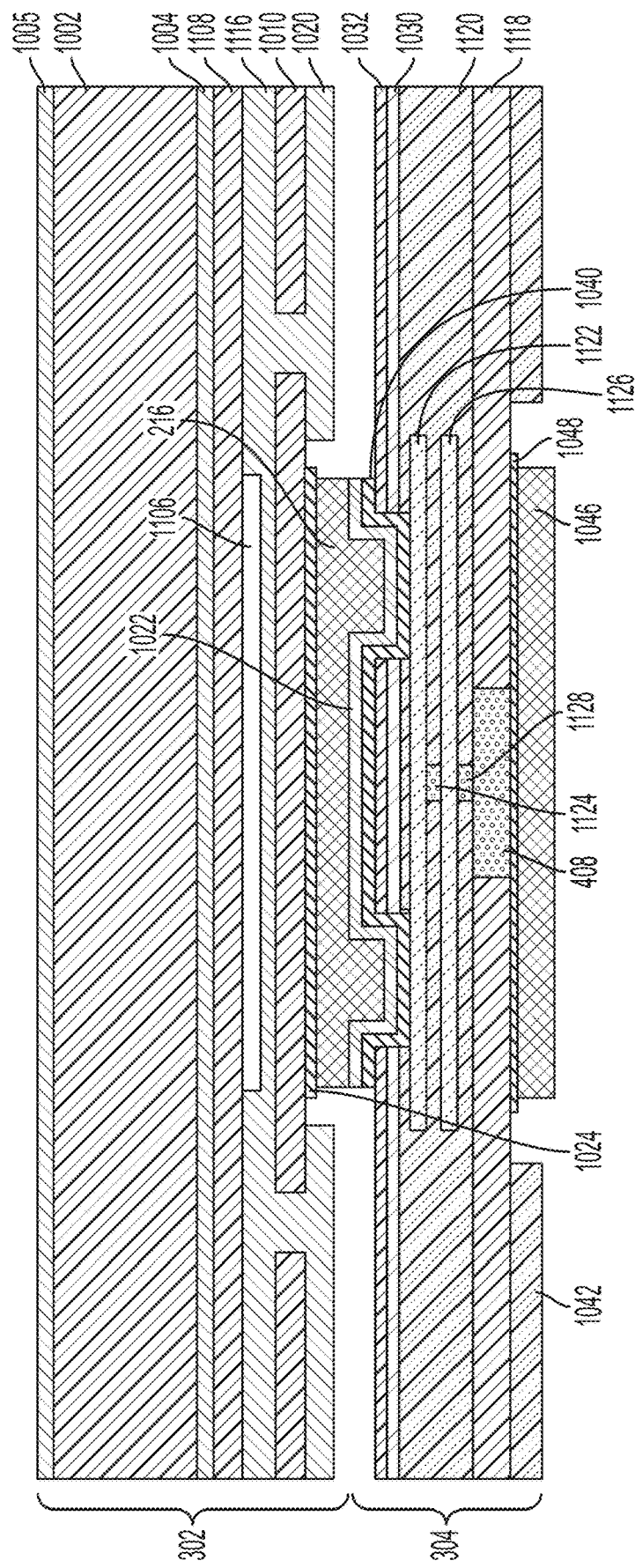

In FIG. 28, a bonding structure 1046 is formed on the second device 304 (by suitable deposition and patterning) at a location for bonding the first device 302 with the second device 304, similar to as described in relation to FIG. 19. The bonding structure 1046 is shown adhered to an adhesion structure 1048.

Figure 29:
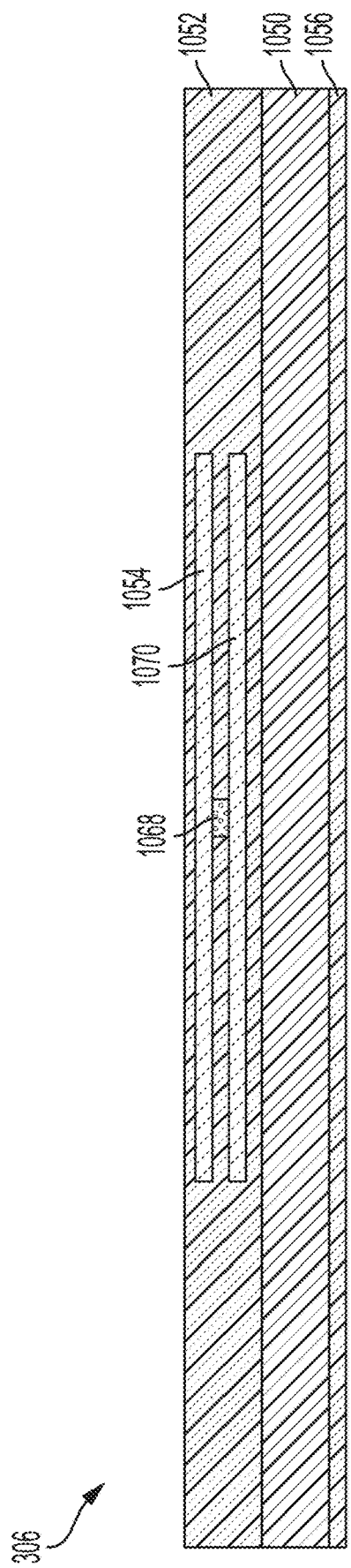

As shown in FIG. 29, the third device 306 includes a base layer (e.g., a bulk silicon wafer) 1050, an insulating layer 1052, metallization 1054, a via 1068, and metallization 1070. The via 1068 electrically connects the metallization 1054 and the metallization 1070. An insulating layer 1056 is formed on the backside of the base layer 1050. The metallization 1054 and the metallization 1070 may be formed of aluminum, copper, or any other suitable metallization material, and may represent at least part of an integrated circuit formed in the third device 306. For example, the metallization 1054 and the metallization 1070 may serve as routing layers, may be patterned to form one or more electrodes, or may be used for other functions. In practice, the third device 306 may include more than two metallization layers and/or post-processed redistribution layers, but for simplicity only two metallizations are illustrated. The third device 306 may be fabricated by a commercial foundry.

Figure 30:
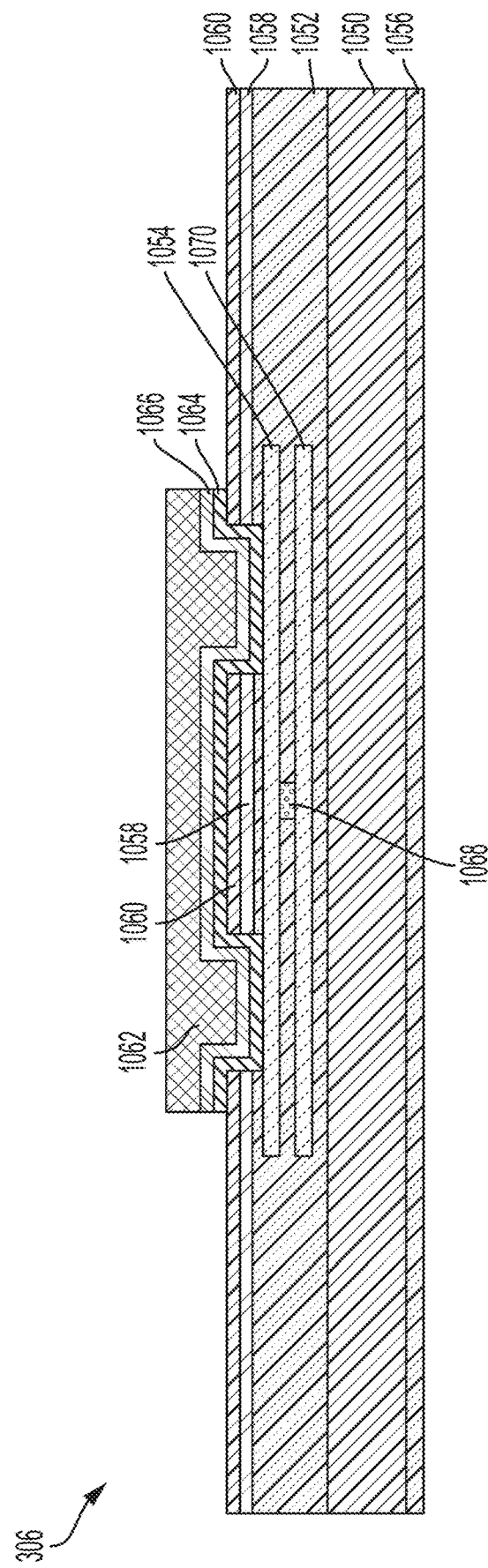

As shown in FIG. 30, layers 1058 and 1060, bonding structure 1062, and adhesion structures 1064 and 1066 are formed on the third device 306 in a similar way as described in relation to FIGS. 21-23.

Figure 31:
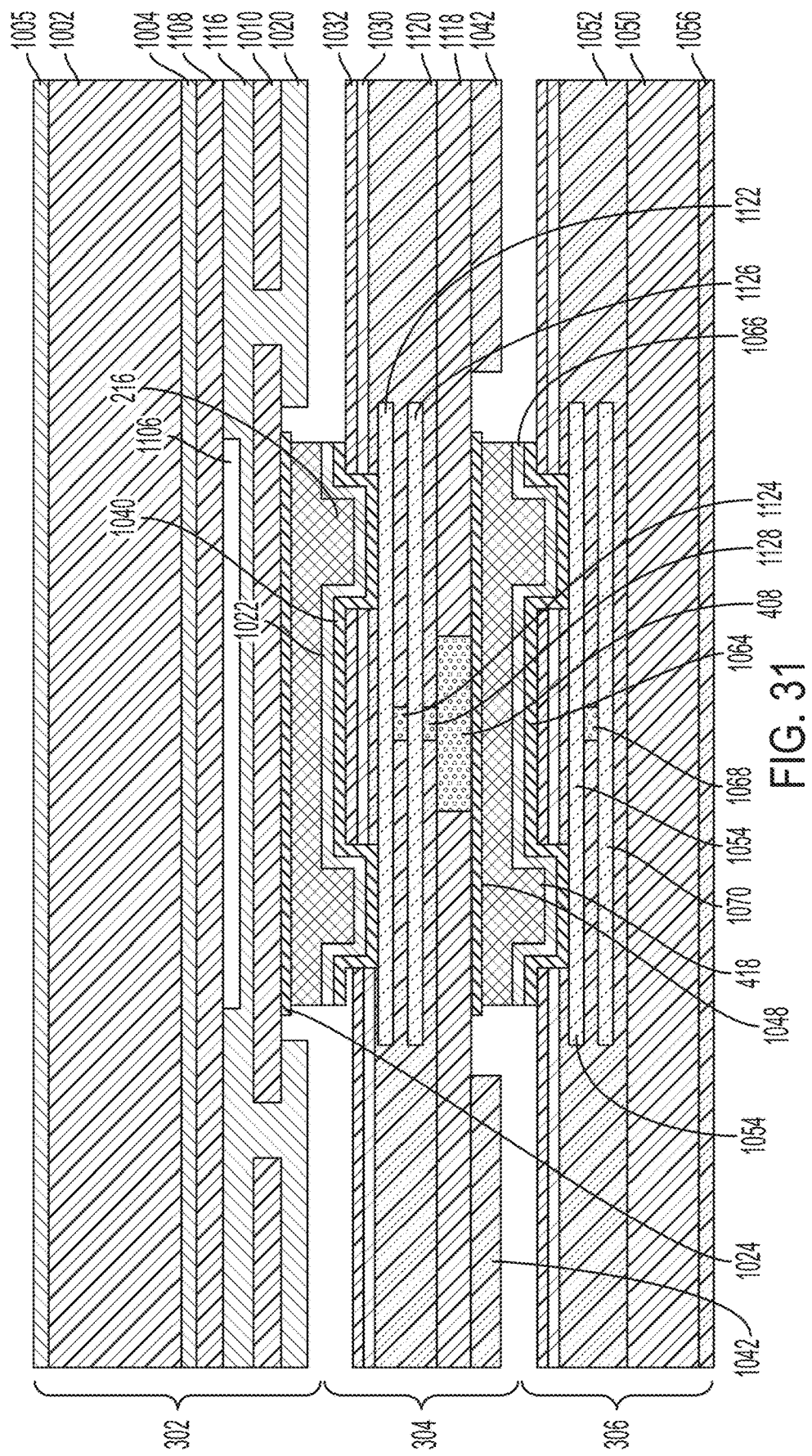

As shown in FIG. 31, the third device 306 and the second device 304 are then bonded together, similar to as described in relation to FIG. 24. In the non-limiting example illustrated, the bond is a eutectic bond, such that the bonding structure 1026 and the bonding structure 1036 in combination form the bonding point 418. As a further non-limiting example, a thermocompression bond may be formed.

Figure 32:
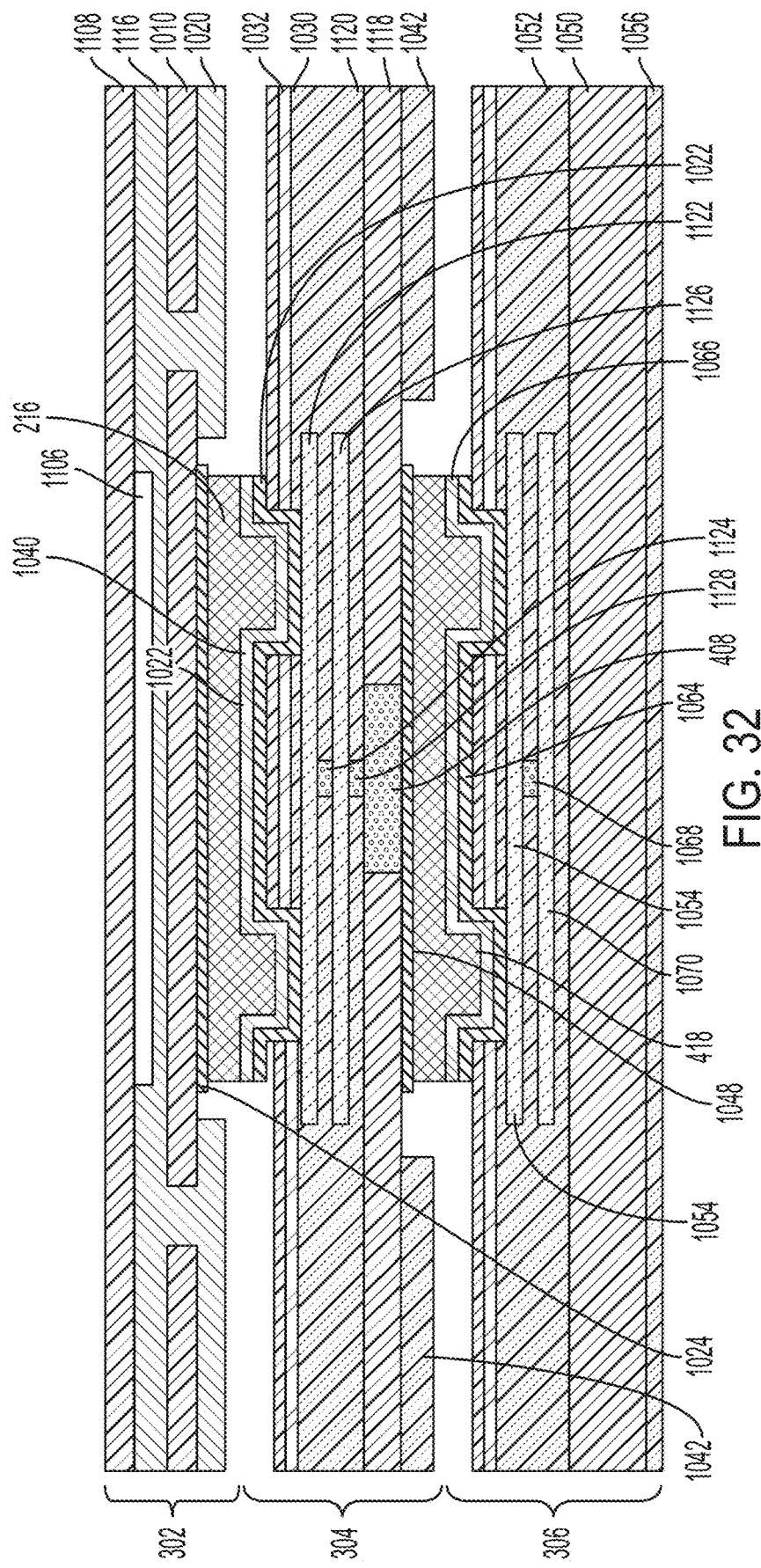

As shown in FIG. 32, the oxide layer 1005, the handle layer 1002, and the BOX layer 1004 are removed, in any suitable manner, similar to as described in relation to FIG. 15. For example, grinding, etching, or any other suitable technique or combination of techniques may be used. Sufficient structural integrity may be provided for this processing step by the base layer 1050.

Following removal of the oxide layer 1005, the handle layer 1002, and the BOX layer 1004, additional processing on top of silicon device layer 1108 may be performed. For example, electrical contacts (which may be formed of metal or any other suitable conductive contact material) may be formed on the silicon device layer 1108. In some embodiments, an electrical connection may be provided between the contacts on the silicon device layer 1108 and a bond pad on the second device 304 and/or the third device 306. For example, a wire bond may be provided or a conductive material (e.g., metal) may be deposited over the upper surface of the ultrasound device 300 and patterned to form a conductive path from the contact to the bond pad. However, alternative manners of connecting the contact to the second device 304 and/or the third device 306 may be used. In some embodiments, an embedded via may be provided from the silicon device layer 1108 to the second device 304 and/or the third device 306.

For further description of fabrication of ultrasound devices and additional processing steps that may be performed, see U.S. Pat. No. 9,067,779 titled "MICROFABRICATED ULTRASONIC TRANSDUCERS AND RELATED APPARATUS AND METHODS," granted on Jun. 30, 2015 (and assigned to the assignee of the instant application) which is incorporated by reference herein in its entirety.

It will be appreciated that alternative fabrication sequences to the sequence described in FIGS. 10-32 are possible. In some embodiments, the fabrication sequence may proceed in a different order than illustrated in FIGS. 10-32. In some embodiments, the second device 304 may not be thinned down. In some embodiments, the second device 304 may be bonded to the third device 306 before being bonded to the first device 302. In such embodiments, the second device 304 may not be thinned down, or if the second device 304 is thinned down, the second device 304 may first be bonded to a carrier wafer to provide structural integrity for the thinning process. The second device 304 may be thinned prior to bonding the second device 304 to the third device 306. The carrier wafer may be removed either before or after bonding the second device 304 to the third device 306.

Figure 33:
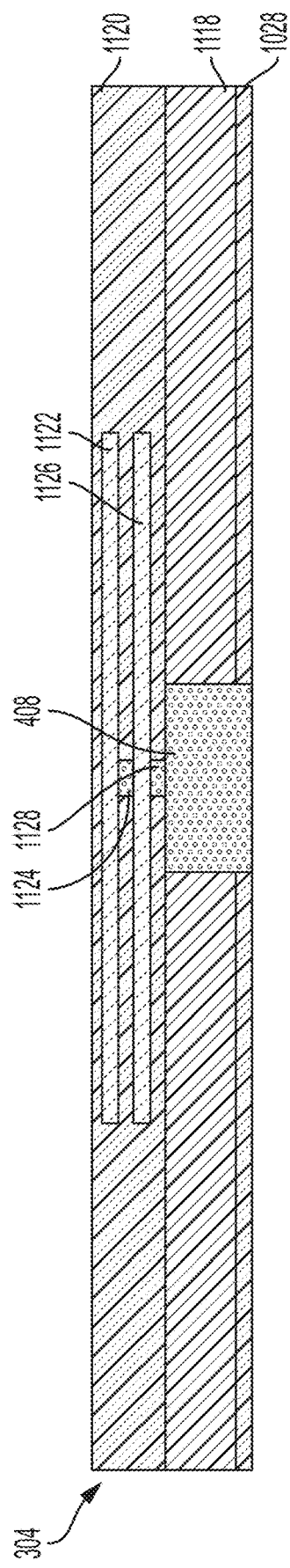
Figure 34:
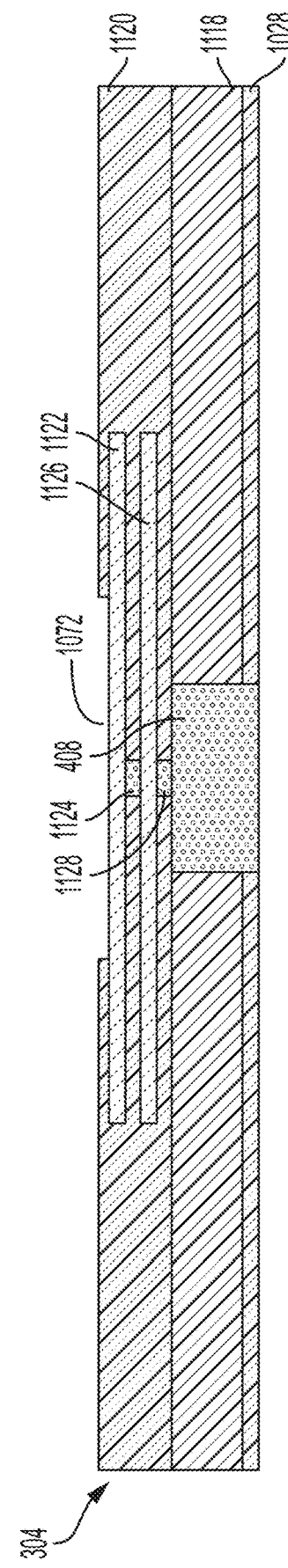
Figure 35:
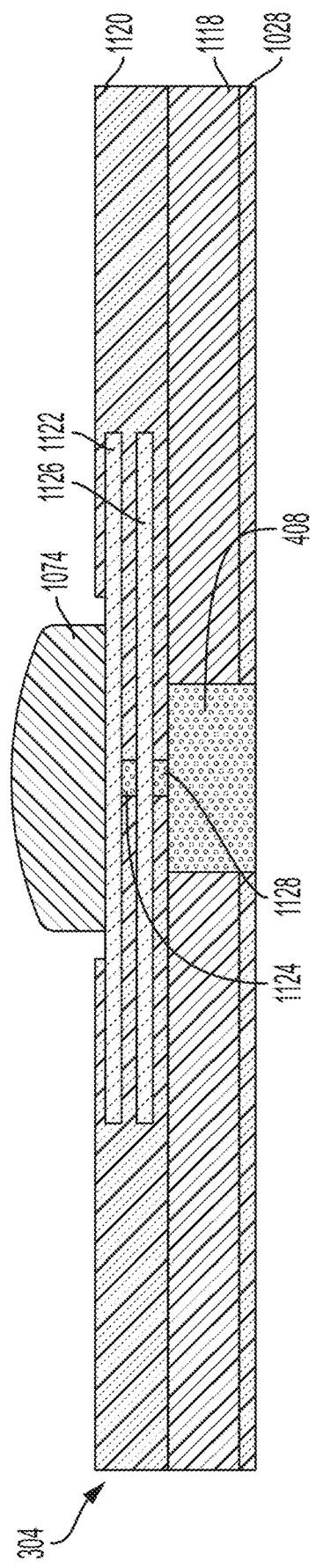

FIGS. 33-42 illustrate example cross-sections of the ultrasound device 300 during an alternative fabrication sequence to that of FIGS. 20-32. FIG. 33 illustrates the second device 304, which is the same as that of FIG. 20. As shown in FIG. 34, an opening 1072 is formed in the insulating layer 1120 (using any suitable etch technique) to expose a portion of the metallization 1122. In FIG. 35, a solder ball 1074 is deposited on the exposed portion of the metallization 1120. FIG. 36 illustrates the third device 306, which is the same as that of FIG. 29. As shown in FIG. 37, an opening 1076 is formed in the insulating layer 1052 (using any suitable etch technique) to expose a portion of the metallization 1054 that constitutes a bonding pad.

Figure 38:
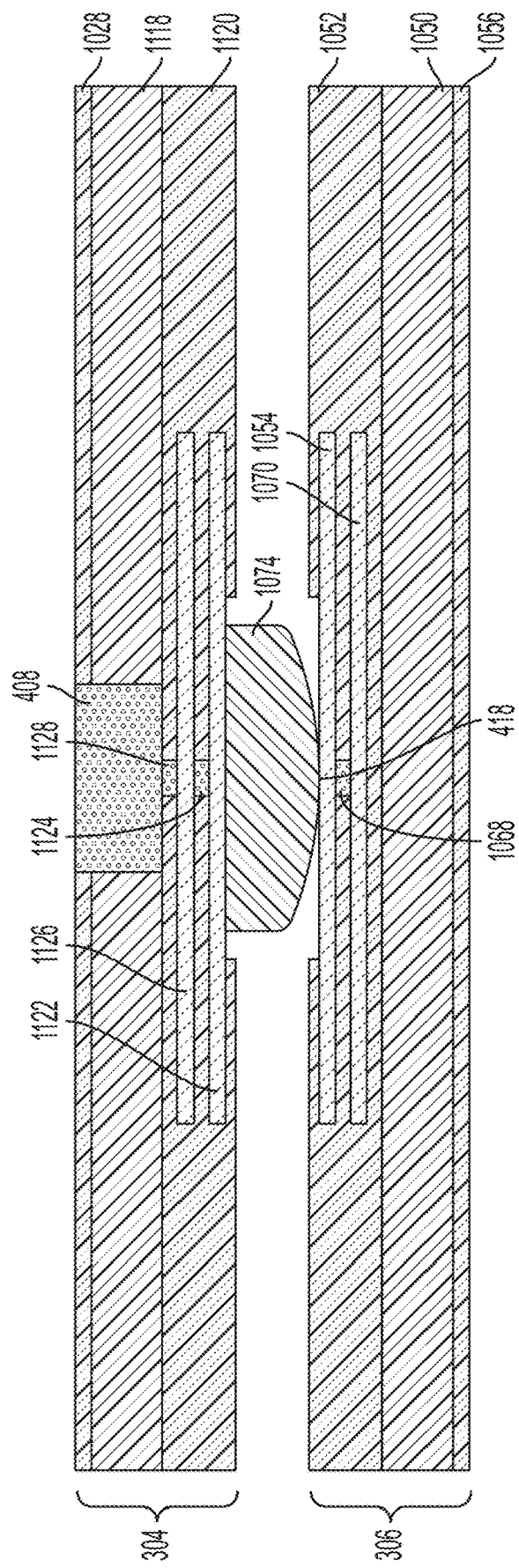
Figure 39:
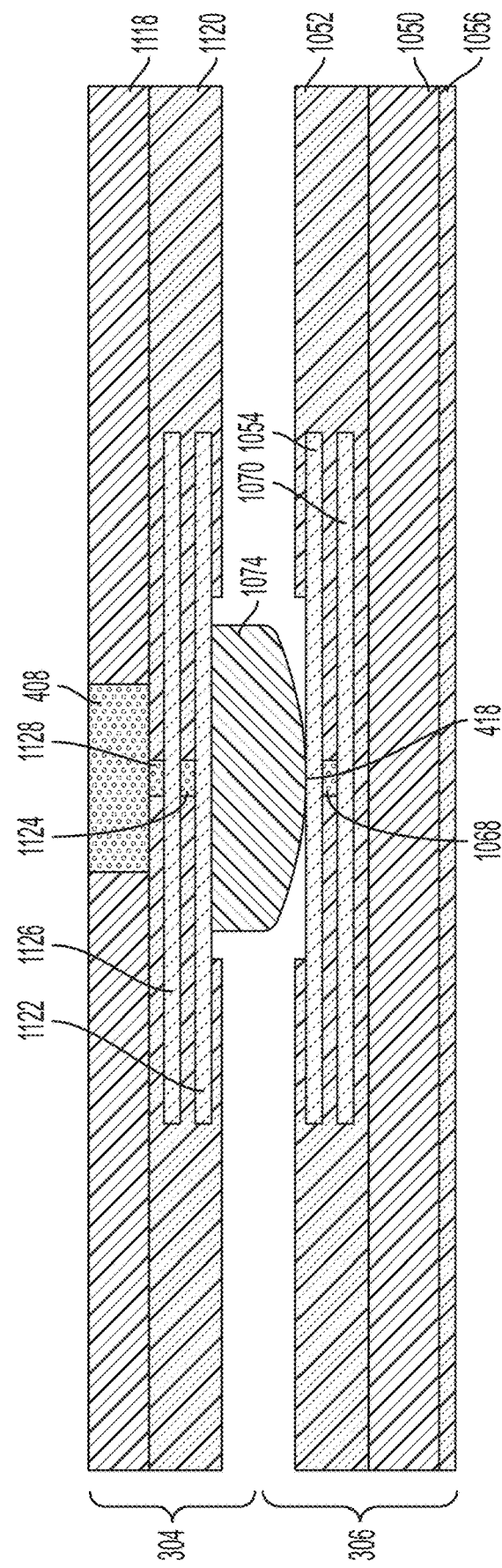
Figure 40:
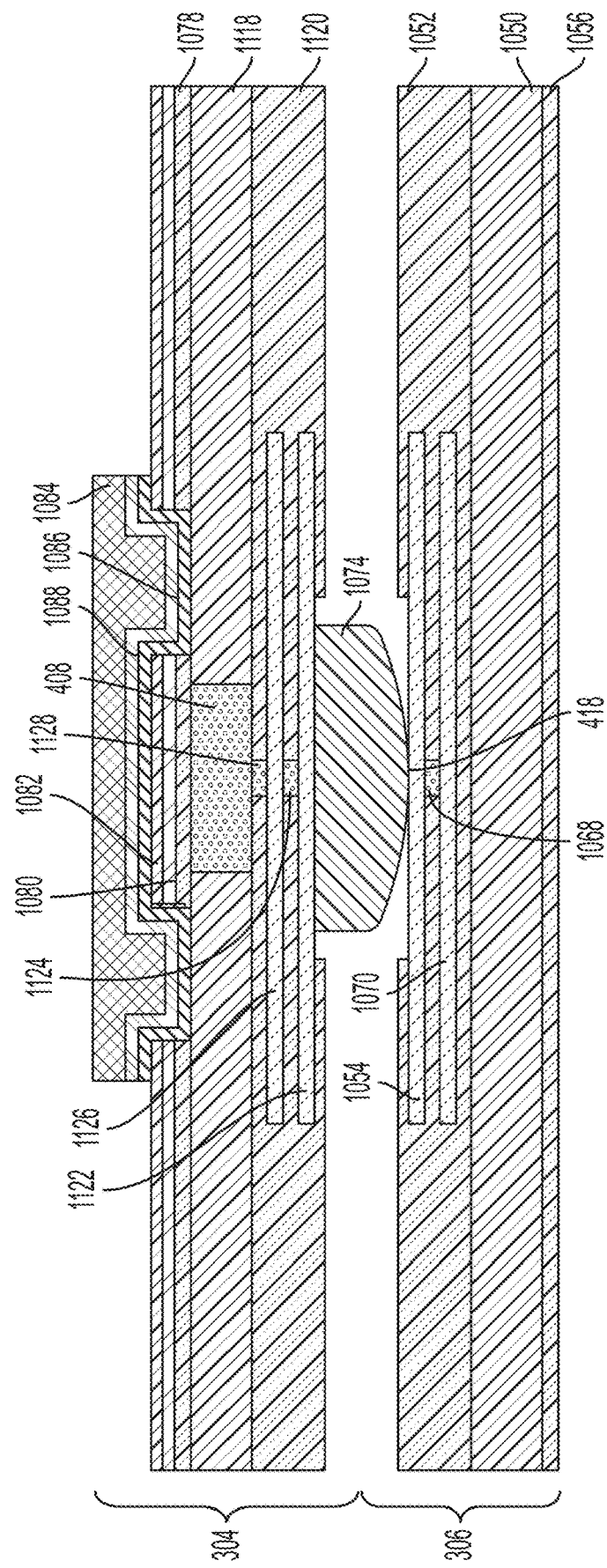

In FIG. 38, the second device 304 and the third device 306 are bonded by flipping the second device 304 from top to bottom from the orientation shown in FIGS. 33-35. The second device 304 and the third device 306 are brought together such that the solder ball 1074 in the second device 304 contacts the exposed portion of the metallization 1054 in the third device 306 and forms an electrical connection between the metallization 1122 and the metallization 1054, thus constituting the bonding point 418. The bonding point 418 forms an electrical contact between the second device 304 and the third device 306. The solder ball 1074 may be remelted after contacting the metallization 1054. In embodiments in which the second device 304 and the third device 306 are dies, this bonding process may constitute flip chip bonding. In embodiments in which the second device 304 and the third device 306 are wafers, this bonding process may constitute a wafer-level equivalent of flip chip bonding in which one or more solder balls on the second device 304 are bonded to one or more bonding pads on the third device 306. In FIG. 39, the insulating layer 1028 is removed, and the TSV 408 and base layer 1118 are reduced in height, similar to as described with reference to FIG. 25. In FIG. 40, an insulating material 1078 is deposited on the second device 304 and patterned, similar to as described with reference to FIGS. 26-27. Furthermore, layers 1086 and 1088, bonding structure 1084, and adhesion structures 1080 and 1082 are formed on the second device 304 in a similar way as described in relation to FIGS. 21-23.

Figure 41:
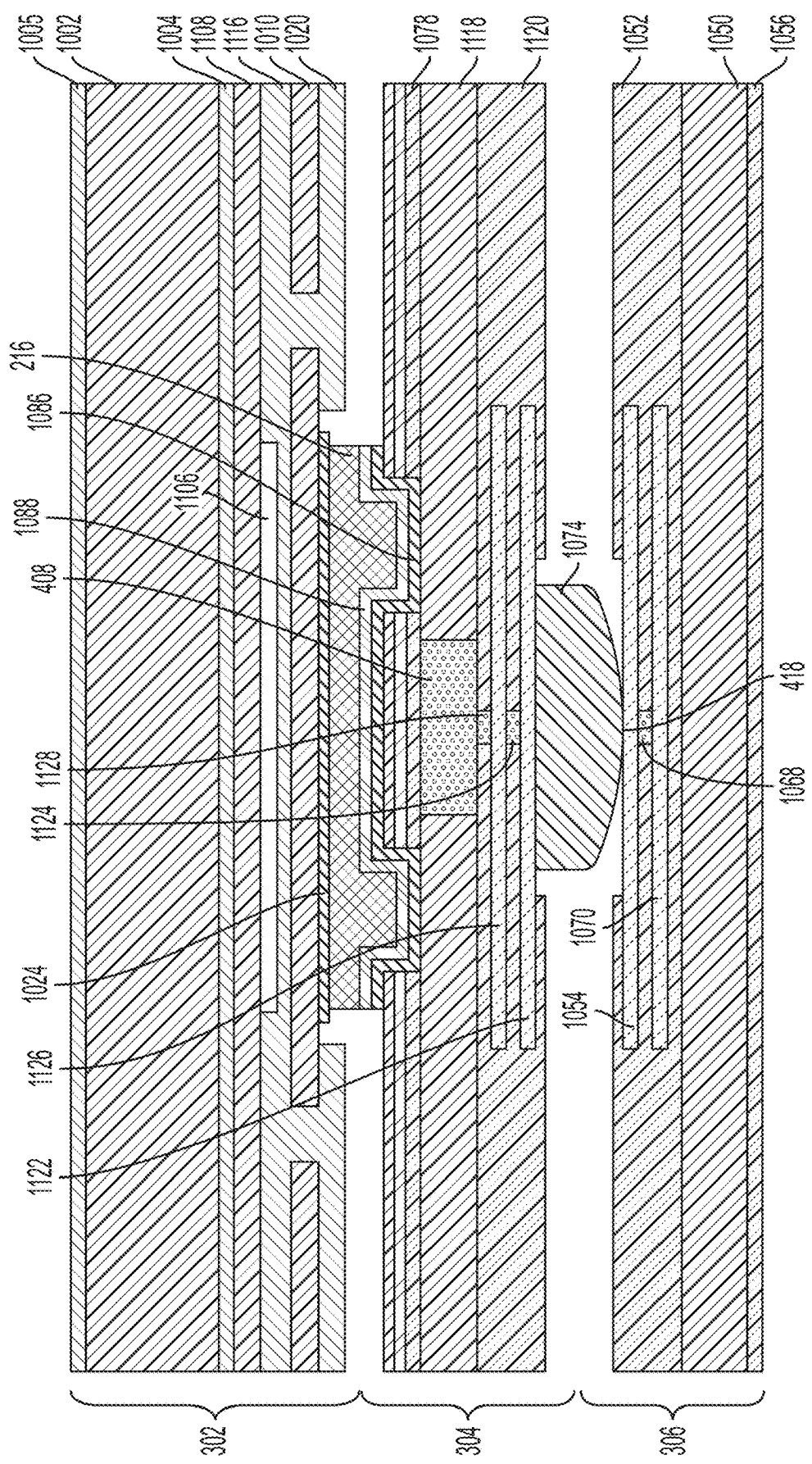
Figure 42:
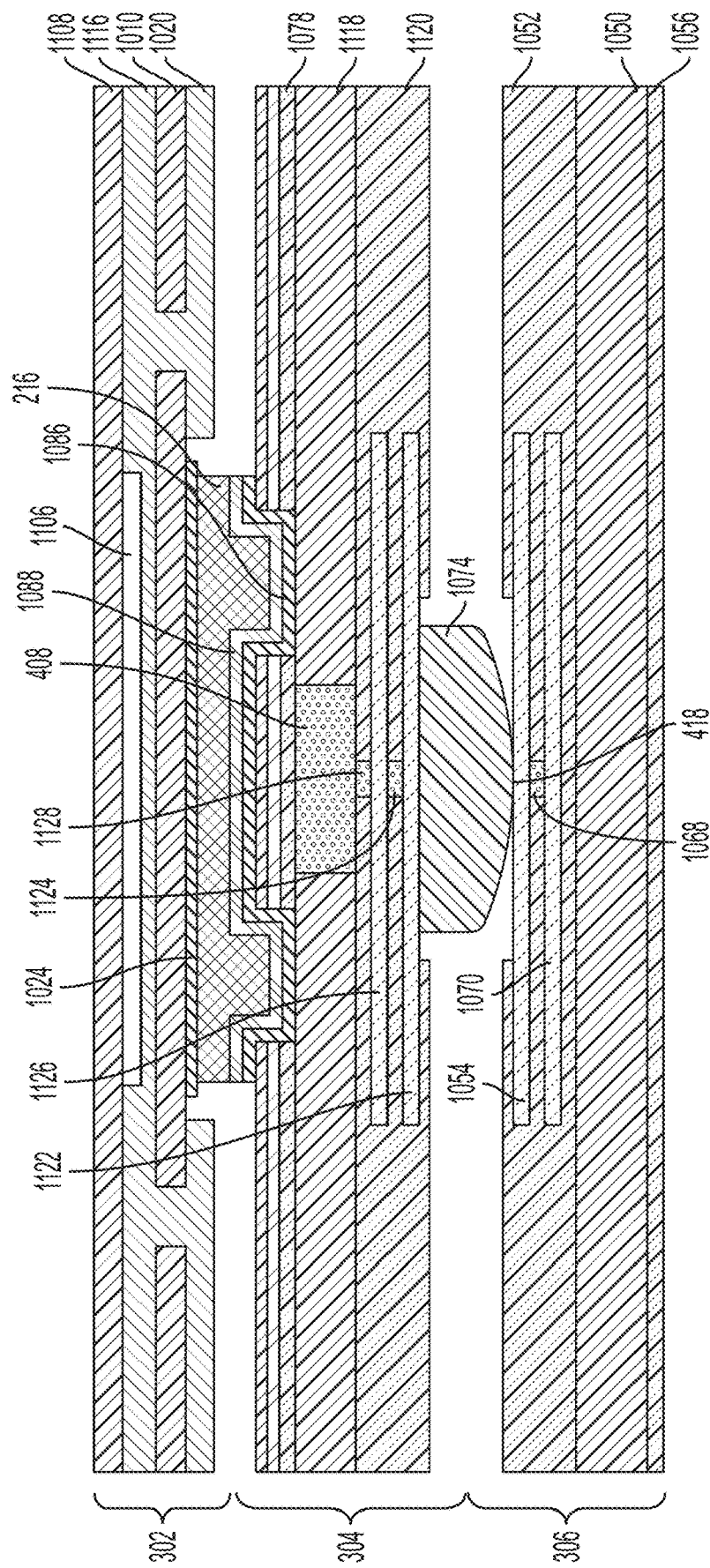

In FIG. 41, the first device 302 is bonded to the second device 304 to form the bonding point 216, in a similar way as described in relation to FIG. 24. As shown in FIG. 42, the oxide layer 1005, the handle layer 1002, and the BOX layer 1004 are removed, similar to as described in relation to FIG. 32.

It will be appreciated that alternative fabrication sequences to the sequence described in FIGS. 33-42 are possible. In some embodiments, the fabrication sequence may proceed in a different order than illustrated in FIGS. 10-32. In some embodiments, the second device 304 may not be thinned down. In some embodiments, the second device 304 may be bonded to the first device 302 before being bonded to the third device 306. In such embodiments, the second device 304 may not be thinned down, or if the second device 304 is thinned down, the second device 304 may first be bonded to a carrier wafer to provide structural integrity for the thinning process. The second device 304 may be thinned prior to bonding the second device 304 to the third device 306. The carrier wafer may be removed either before or after bonding the second device 304 to the third device 306.

It should also be noted that bonding between the first device 302 and the second device 304 and/or bonding between the second device 304 and the third device 306 may be accomplished using redistribution and solder bump technology. Further description of bonding using redistribution and solder bump technology can be found in U.S. patent application Ser. No. 14/799,484 titled "MICROFABRICATED ULTRASONIC TRANSDUCERS AND RELATED APPARATUS AND METHODS," filed on Jul. 14, 2015 and published as U.S. Patent Publication No. 2016/0009544 A1 (and assigned to the assignee of the instant application), which is incorporated by reference herein in its entirety.

Figure 43:
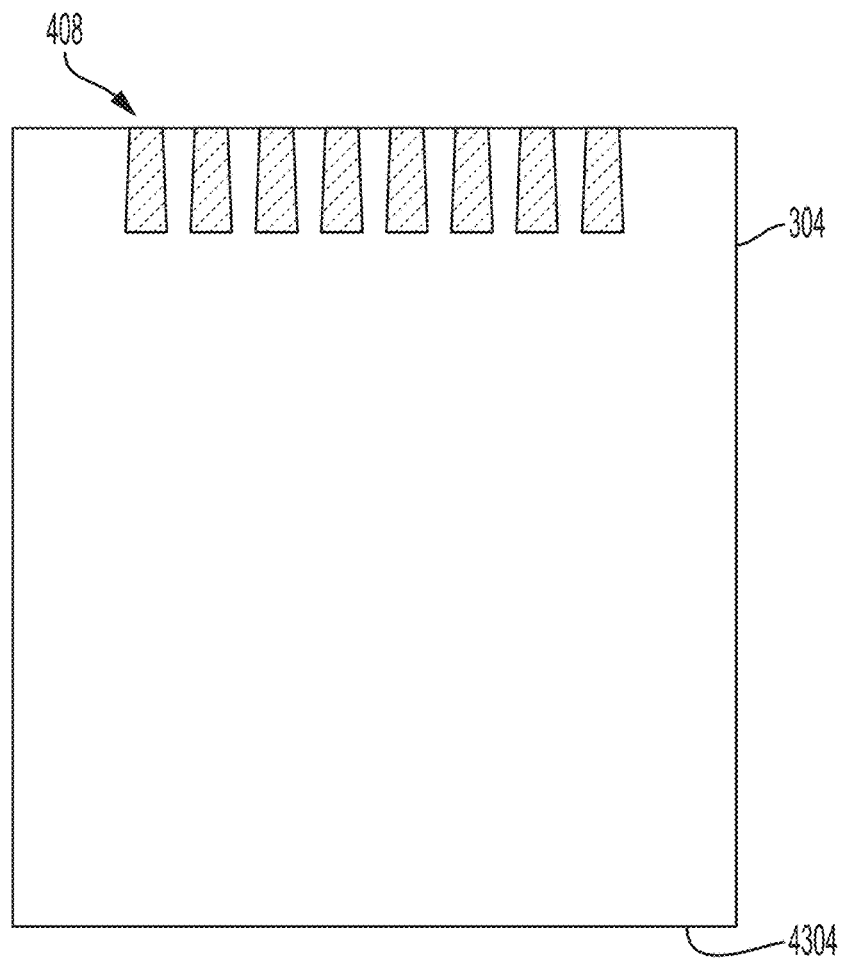
FIGS. 43-45 illustrate simplified cross-sections of an ultrasound device during an alternative fabrication sequence in accordance with certain embodiments described herein.
Figure 44:
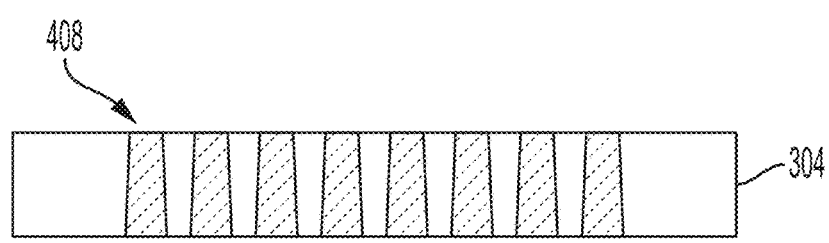
Figure 45:
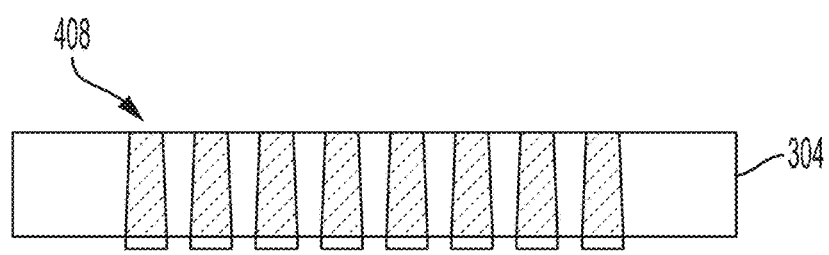

FIGS. 43-45 illustrate simplified cross-sections of the second device 304 during an alternative fabrication sequence for forming the ultrasound device 300 in accordance with certain embodiments described herein. In FIG. 43, a simplified version of the second device 304 includes a plurality of TSVs 408 which do not extend to the bottom surface 4304 of the second device 304. Other components of the second device 304, including those components previously described, are omitted from this figure for simplicity of illustration. In FIG. 43, the plurality of TSVs 408 are conical. Integrated circuit foundries typically impose design rules on the integrated circuits they fabricate. For example, design rules for TSVs may limit how closely TSVs can be spaced together. In FIG. 43, the wide ends of the plurality of TSVs 408 have smaller diameters than would the wide ends of TSVs that extend to the bottom surface 4304 of the second device 304. The design rules governing spacing of TSVs may therefore allow the plurality of TSVs 408 in FIG. 43 to have a smaller pitch than if the plurality of TSVs 408 extended to the bottom surface 4304 of the second device 304. Because, as described above, each of the plurality of TSVs 408 in the second device 304 may correspond to a single ultrasonic transducer 260 in the first device 302, reducing the pitch of the plurality of TSVs 408 may enable reducing the pitch of the ultrasonic transducers 260 and increasing how many ultrasonic transducers 260 can be implemented in the first device 302. In FIG. 44, the second device 304 is thinned to expose the plurality of TSVs 408, using a similar process as described in relation to FIGS. 25 and 39. In FIG. 45, bonding structures 4306 are implemented at the exposed surfaces of the plurality of TSVs 408, using the same or a substantially similar process as described in relation to FIGS. 26-28 and 40, to facilitate electrical connection of the TSVs to the third device 306 when the third device 306 is bonded to the second device 304. In some embodiments, the plurality of TSVs 408 may be conical with their narrow ends proximal to the bottom surface 4304 of the second device 304, as opposed to the wider ends being proximal to the bottom surface 4304 of the second device 304 as shown in FIG. 43. In such embodiments, the above advantages may still be realized in a similar manner as described above by limiting the distance that the plurality of TSVs 408 extend from their narrow ends to their wide ends. In some embodiments, the plurality of TSVs 408 may not be conical.

It should be appreciated that any of the fabrication sequences described herein may be used to fabricate the ultrasound devices 300, 400, 500, 600, 700, or 800. Additionally, the fabrication sequence illustrated in FIGS. 10-25 may be used for bonding a first device to a second device in the ultrasound devices 100 and 200, although the second device may lack a TSV 408.

Figure 46:
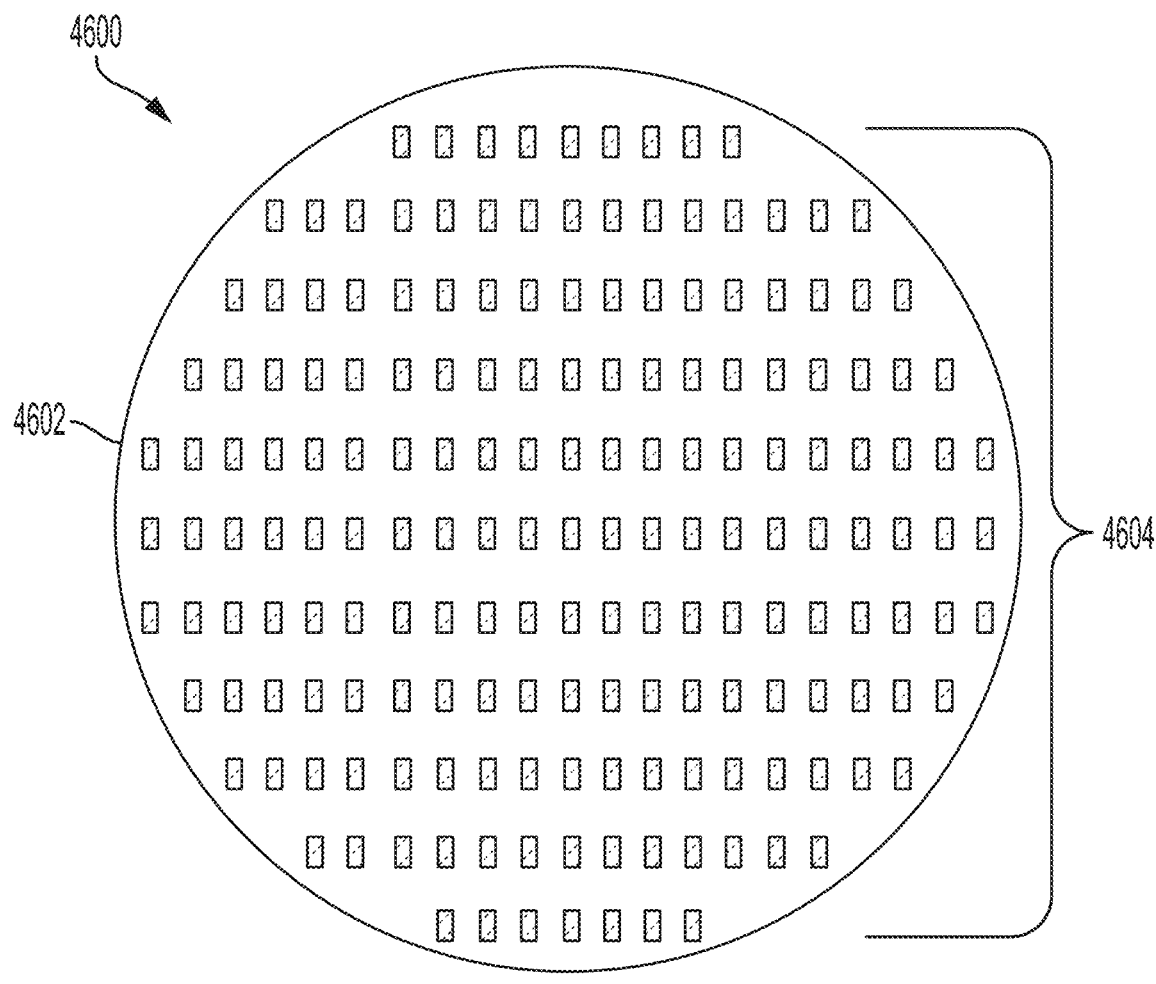
FIG. 46 illustrates an example of a device implemented as a reconstituted wafer, in accordance with certain embodiments described herein.

FIG. 46 illustrates an example of a device implemented as a reconstituted wafer, in accordance with certain embodiments described herein. As referred to herein, a "reconstituted wafer" is a wafer on which multiple dies are mounted. The reconstituted wafer 4600 includes a wafer 4602 and a plurality of dies 4604. The plurality of dies 4604 are coupled to the wafer 4602, for example by a mold compound. Implementing the second device 304 and/or the third device 306 as a reconstituted wafer 4600 may be beneficial because it may be possible to test dies for functionality/performance prior to forming the reconstituted wafer 4600 and choose which dies to include in the reconstituted wafer 4600 based on the testing. Additionally, as described above, the third device 306 and the second device 304 may be dies. As further described above, the third device 306 may be implemented in a more advanced technology node than the second device 304. Due to cost and yield considerations, it may not be desirable to fabricate dies in a more advanced (smaller) technology node that are the same size as dies fabricated in a less advanced (larger) technology node. If the third device 306 as a die is not the same size as the second device 304 as a die, the third device 306 may not be able to bond to each bond point on the second device 304. If the second device 304 is implemented as a reconstituted wafer 4600, and the plurality of dies 4604 include integrated receive circuitry, groups of two or more of the plurality of dies 4604 may then align with and bond to one die including integrated transmit circuitry in the second device 304 when the second device 304 is a wafer including multiple dies. This may be beneficial when, for example, the plurality of dies 4604 in the third device 306 are smaller in size than the dies in the second device 304.

Figure 47:
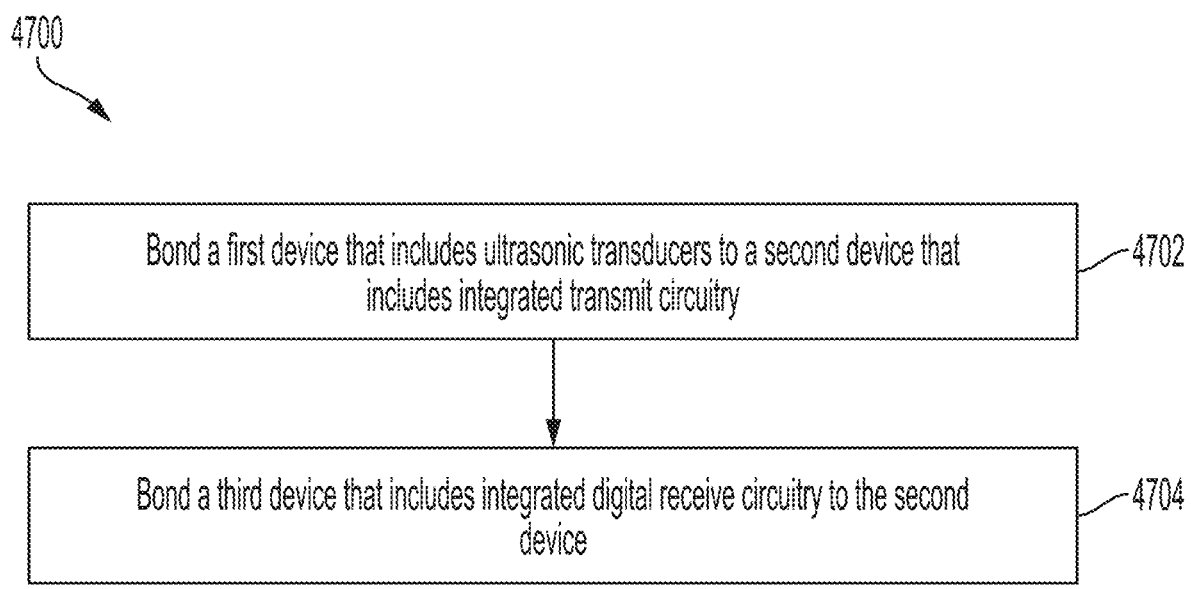
FIG. 47 illustrates an example process for forming an ultrasound device in accordance with certain embodiments described herein.

FIG. 47 illustrates an example process 4700 for forming an ultrasound device in accordance with certain embodiments described herein. In act 4702, a first device that includes ultrasonic transducers is bonded to a second device that includes integrated transmit circuitry (e.g., pulsers), for example as described above in reference to FIGS. 10-24. In some embodiments, the second device may also include integrated analog receive circuitry (e.g., amplifiers and ADCs). The process 4700 then proceeds to act 4704. In act 4704, a third device that includes integrated digital receive circuitry is bonded to the second device, for example as described above in reference to FIGS. 25-32. In some embodiments, the third device may also include integrated analog receive circuitry (e.g., amplifiers and ADCs). In some embodiments, act 4704 may be absent, and the third device may not be bonded to the second device. Instead, the third device may be coupled to the same PCB as the stack of the first device and the second device, and the third device may be in communication with the second device (e.g., through a trace on the PCB).

Figure 48:
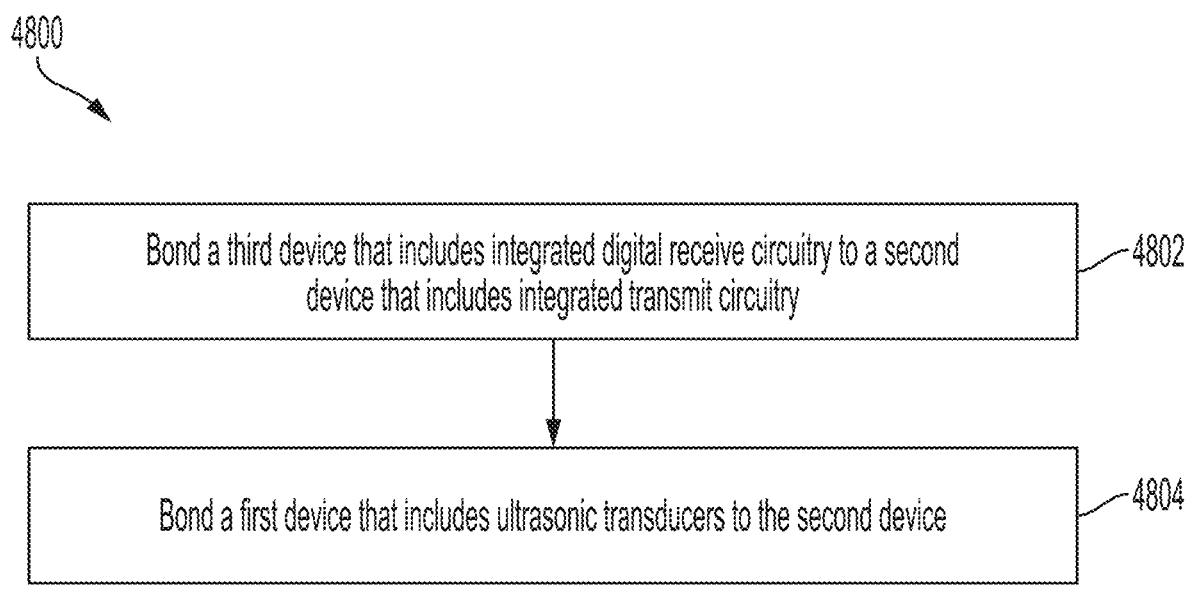
FIG. 48 illustrates an example process for forming an ultrasound device in accordance with certain embodiments described herein.

FIG. 48 illustrates an example process 4800 for forming an ultrasound device in accordance with certain embodiments described herein. In act 4802, a third device that includes integrated digital receive circuitry is bonded to a second device that includes integrated transmit circuitry (e.g., pulsers), for example as described above in reference to FIGS. 33-38. In some embodiments, the second device may also include integrated analog receive circuitry (e.g., amplifiers and ADCs). In some embodiments, the third device may also include integrated analog receive circuitry (e.g., amplifiers and ADCs). The process 4800 then proceeds to act 4804. In act 4804, a first device that includes ultrasonic transducers is bonded to the second device, for example as described above in reference to FIGS. 39-42. In some embodiments, act 4802 may be absent, and the third device may not be bonded to the second device. Instead, the third device may be coupled to the same PCB as the stack of the first device and the second device, and the third device may be in communication with the second device (e.g., through a trace on the PCB).

Figure 49:
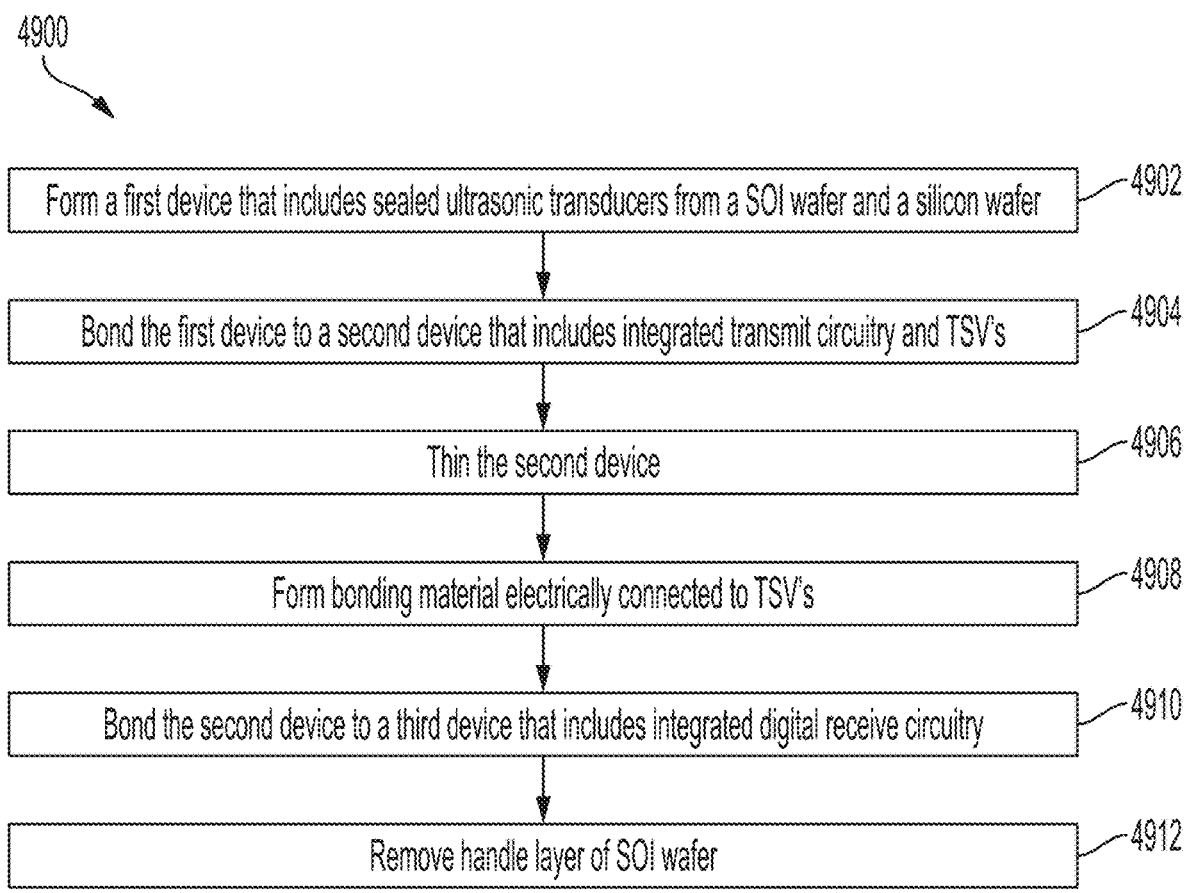
FIG. 49 illustrates an example process for forming an ultrasound device in accordance with certain embodiments described herein.

FIG. 49 illustrates an example process for 4900 for forming an ultrasound device in accordance with certain embodiments described herein. In act 4902, a first device that includes ultrasonic transducers is formed from an SOI wafer and a silicon wafer, for example as described above in relation to FIGS. 10-15. The process 4900 then proceeds to act 4904. In act 4904, the first device is bonded to a second device that includes integrated transmit circuitry (e.g., pulsers) and TSVs, for example as described above in relation to FIGS. 16-24. The process 4900 then proceeds to act 4906. In act 4906, the second device is thinned, for example as described above in relation to FIG. 25. The process 4900 then proceeds to act 4908. In act 4908, bonding structures that are electrically connected to the TSVs are formed, for example as described above in relation to FIGS. 26-28. The process 4900 then proceeds to act 4910. In act 4910, the second device is bonded to a third device that includes integrated digital receive circuitry, for example as described above in relation to FIGS. 29-31. The process 4900 then proceeds to act 4912. In act 4912, the handle layer of the SOI wafer is removed, for example as described above in relation to FIG. 32. In some embodiments, the second device may also include integrated analog receive circuitry (e.g., amplifiers and ADCs). In some embodiments, the third device may also include integrated analog receive circuitry (e.g., amplifiers and ADCs). In some embodiments, act 4910 may be absent, and the third device may not be bonded to the second device. Instead, the third device may be coupled to the same PCB as the stack of the first device and the second device, and the third device may be in communication with the second device (e.g., through a trace on the PCB).

Figure 50:
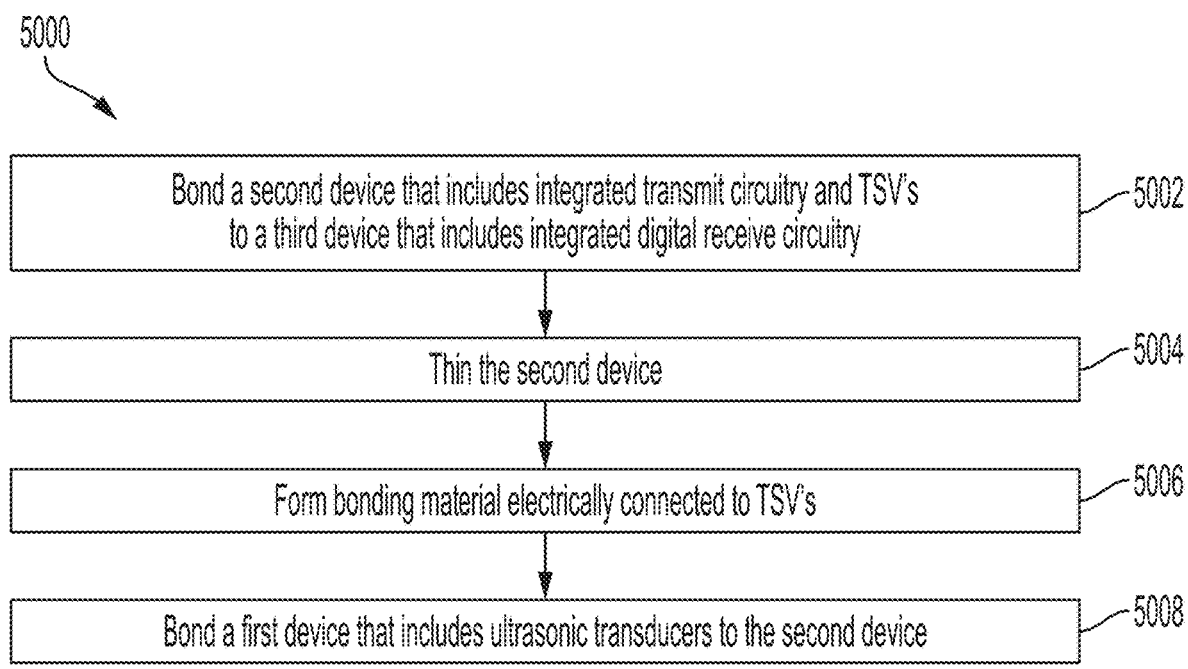
FIG. 50 illustrates an example process for forming an ultrasound device in accordance with certain embodiments described herein.

FIG. 50 illustrates an example process 5000 for forming an ultrasound device in accordance with certain embodiments described herein. In act 5002, a second device that includes integrated transmit circuitry (e.g., pulsers) is bonded to a third device that includes integrated digital receive circuitry, for example as described above in relation to FIGS. 33-38. The process 5000 then proceeds to act 5004. In act 5004, the second device is thinned, for example as described above in relation to FIG. 39. The process 5000 then proceeds to act 5006. In act 5006, bonding structures that are electrically connected to the TSVs are formed, for example as described above in relation to FIG. 40. The process 5000 then proceeds to act 5008. In act 5008, the first device 302 that includes ultrasonic transducers is bonded to the second device 304, for example as described above in relation to FIGS. 41-42. In some embodiments, the second device may also include integrated analog receive circuitry (e.g., amplifiers and ADCs). In some embodiments, the third device may also include integrated analog receive circuitry (e.g., amplifiers and ADCs). In some embodiments, act 5002 may be absent, and the third device may not be bonded to the second device. Instead, the third device may be coupled to the same PCB as the stack of the first device and the second device, and the third device may be in communication with the second device (e.g., through a trace on the PCB).

As described above, it will be appreciated that alternative processes are possible. In some embodiments, the second device may not be thinned down. In some embodiments, the second device may be bonded to the third device before being bonded to the first device. In such embodiments, the second device may not be thinned down, or if the second device is thinned down, the second device may first be bonded to a carrier wafer to provide structural integrity for the thinning process. The second device may be thinned prior to bonding the second device to the third device. The carrier wafer may be removed either before or after bonding the second device to the third device.

Various inventive concepts may be embodied as one or more processes, of which examples have been provided. The acts performed as part of each process may be ordered in any suitable way. Thus, embodiments may be constructed in which acts are performed in an order different than illustrated, which may include performing some acts simultaneously, even though shown as sequential acts in illustrative embodiments. Further, one or more of the processes may be combined and/or omitted, and one or more of the processes may include additional steps.

Figure 51:
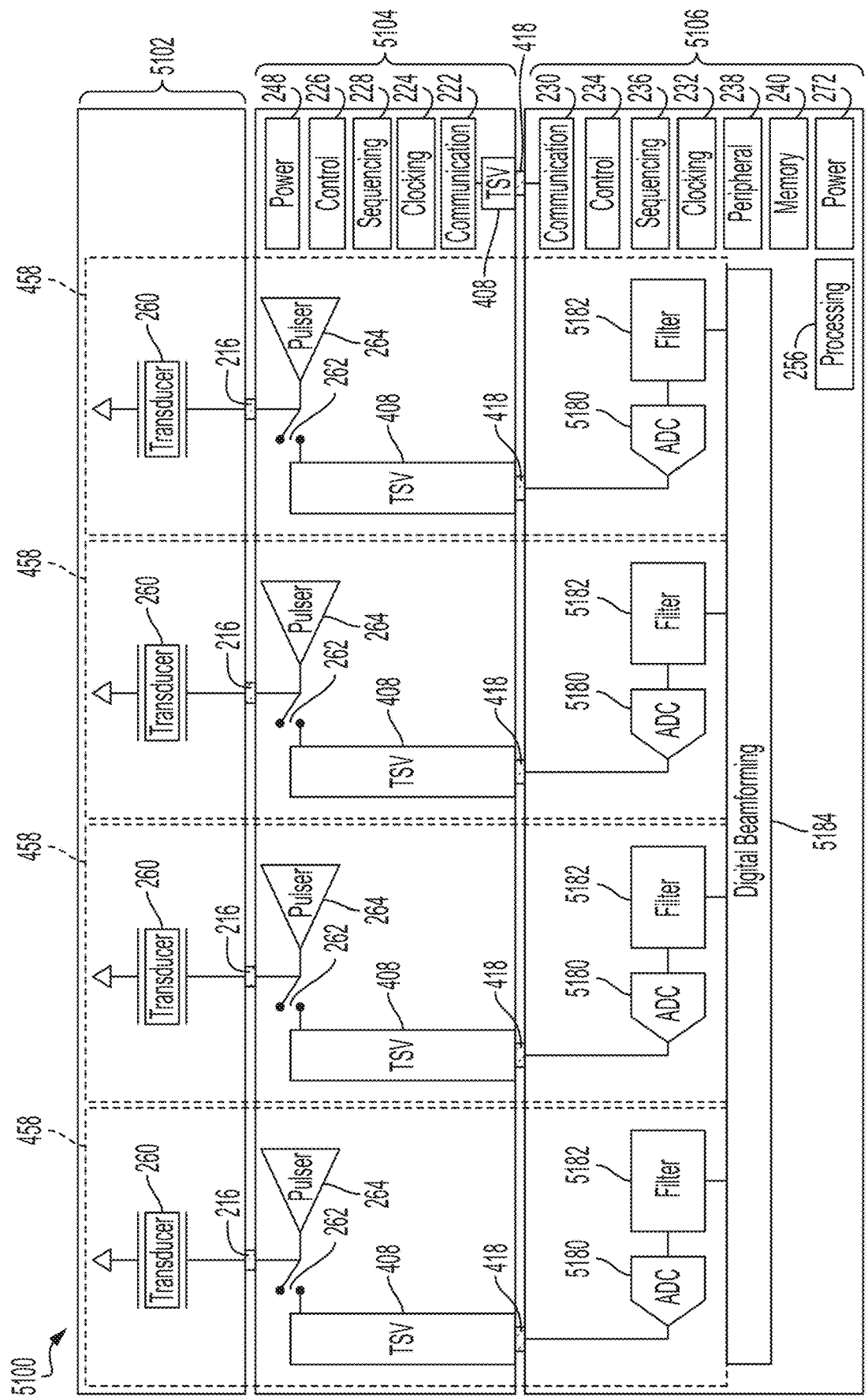
FIG. 51 illustrates an example block diagram of an ultrasound device in accordance with certain embodiments described herein.

FIG. 51 illustrates an example block diagram of an ultrasound device 5100 in accordance with certain embodiments described herein. The ultrasound device 5100 includes a first device 5102, a second device 5104, and a third device 5106. The ultrasound device 5100, the first device 5102, the second device 5104, and the third device 5106 may be examples of the ultrasound device 300, the first device 302, the second device 304, and the third device 306, respectively, illustrated in more detail. The ultrasound device 5100 differs from the ultrasound device 400 in that each ultrasonic transducer 260 is connected, through a receive switch 262, a TSV 208, and a bonding point 418, to an ADC 5180, followed by a filter 5182, followed by digital beamforming circuitry 5184.

The digital beamforming circuitry 5184 may be configured to perform digital beamforming. Digital beamforming may provide higher signal-to-noise ratio (SNR), higher sampling resolution, more flexibility in delay patterns implemented by the digital beamforming circuitry 5184, and more flexibility in grouping of ultrasonic transducers 260 for beamforming, as compared to analog beamforming. However, digital beamforming requires that the analog ultrasonic signal received from each ultrasonic transducer 260 be individually digitized. Certain ultrasound devices described above may include one ADC per element; here, the ultrasound device 5100 illustrates a specific example of implementing per-element digitization. (In FIG. 5100, an element is one ultrasonic transducer 260, but in some embodiments, one element may be a group of ultrasonic transducers 260). In FIG. 51, the ADC 5180 is a delta-sigma ADC (also sometimes referred to as a sigma-delta ADC). The relatively small consumption of power and area by a delta-sigma ADC 5180 as compared with other types of ADCs may make delta-sigma ADCs 5180 practical for an ultrasound device 5100 implementing per-element digitization and digital beamforming. The implementation of one delta-sigma ADC 5180 per ultrasonic transducer 260 (or, in some embodiments, per element) may be feasible when implementing the third device 5106 in a sufficiently small technology node (e.g., 90 nm, 80 nm, 65 nm, 55 nm, 45 nm, 40 nm, 32 nm, 28 nm, 22 nm, 20 nm, 16 nm, 14 nm, 10 nm, 7 nm, 5 nm, or 3 nm) as described above. Each delta-sigma ADC 5180 is directly electrically coupled to an ultrasonic transducer 260. Directly electrically coupling an ultrasonic transducer 260 to an ADC 5180 may mean that there are no amplifiers or multiplexers between the ultrasonic transducer 260 and the ADC 5180, but does not exclude the possibility that the ultrasonic transducer 260 is electrically coupled to the ADC 5180 through the switch 262, the TSV 408, and the bonding point 418. When the ultrasonic transducer 260 is a CMUT, as will be described below, parasitic capacitance inherent to the CMUT may provide integration capability for the delta-sigma ADC 5180 that is typically provided by a separate integrator component. Obviating the need for a separate integrator component may further reduce power consumption and area. The filters 5182 may decimate the oversampled output signal from the delta-sigma ADC 5180 in order to improve the signal-to-quantization-noise ratio (SQNR) of the delta-sigma ADC 5180. The filters 5182 may be cascaded integral-comb (CIC) filters.

Figure 52:
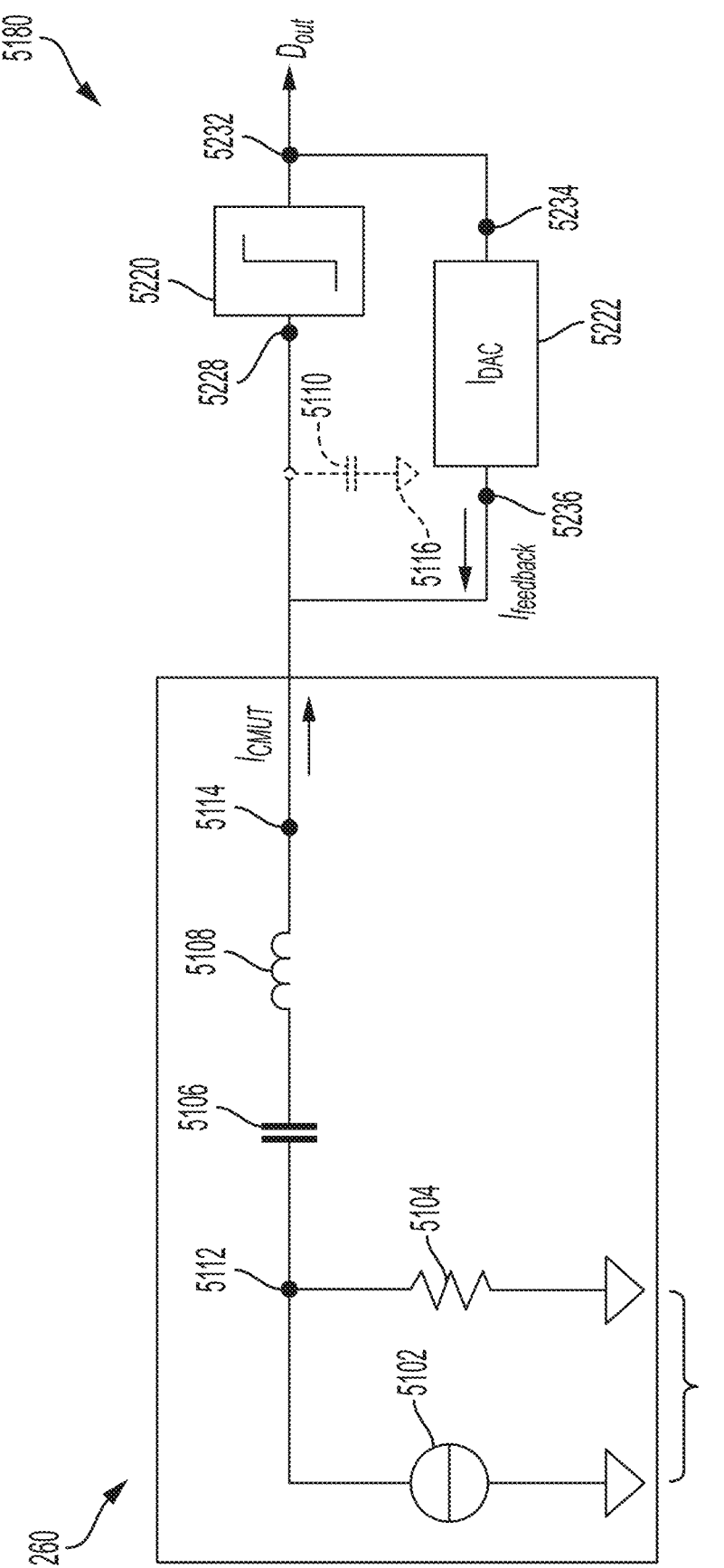
FIG. 52 illustrates a diagram of an ultrasonic transducer electrically coupled to a delta-sigma analog-to-digital converter.

FIG. 52 illustrates a diagram of an ultrasonic transducer 260 electrically coupled to a delta-sigma ADC 5180, in accordance with certain embodiments. For simplicity, in FIG. 52, the pulser 264, the switch 262, the TSV 408, and the bonding point 418 are omitted. In FIG. 52, the ultrasonic transducer is a CMUT and is represented by a circuit model of a CMUT. The circuit model of the ultrasonic transducer 260 includes a current source 5102, a resistor 5104, a capacitor 5106, an inductor 5108, a capacitor 5110, a node 5112, an output terminal 5114, and ground 5116. The current source 5102 is electrically coupled between the node 5112 and ground 5116. The resistor 5104 is electrically coupled between the node 5112 and ground 5116. The capacitor 5106 and the inductor 5108 are electrically coupled in series and are electrically coupled between the node 5112 and the output terminal 5114. The capacitor 5110 is electrically coupled between the output terminal 5114 and ground 5116. The current source 5102 may model the current signal generated by the ultrasonic transducer 260 in response to ultrasonic waves. The resistor 5104, the capacitor 5106, and the inductor 5108 may model the resonant property of the ultrasonic transducer 260. The capacitor 5110 may model parasitic capacitance of the ultrasonic transducer 260. The current difference, $I_{CMUT}$, between the current entering the output terminal 5114 and exiting the output terminal 5114 through the capacitor 5110 may be considered the output current of the ultrasonic transducer 260.

The resonator formed by the resistor 5104, the capacitor 5106, and the inductor 5108 may be considered a low-Q resonator in that the Q of the resonator may be less than 0.5. The resistance of the resistor 5104 may be significantly greater than $1/(\omega * C_p)$, where $\omega$ is the frequency of the current signal $I_{CMUT}$ and $C_p$ is the capacitance of the capacitor 5110. In some embodiments, $C_p$ may be on the order of tenths of femtofarads to tens of millifarads. In some embodiments, $I_{CMUT}$ may be on the order of tens of picoamps to hundreds of microamps, including any value in those ranges.

While typical delta-sigma ADCs include a current integrator, directly electrically coupling the output terminal 5114 of the ultrasonic transducer 260 to the delta-sigma ADC 5180 may obviate the need for a distinct current integrator, as the capacitor 5110 may serve as the current integrator. It should be noted that the capacitor 5110 of the ultrasonic transducer 260 may be considered to be within the feedback loop of the delta-sigma ADC 5180. Thus, in addition to using the capacitor 5110 of the ultrasonic transducer 260 as a current integrator, the delta-sigma ADC 5180 includes a voltage quantizer 5220 and a current digital-to-analog converter (current DAC or $I_{DAC}$) 5222. The voltage quantizer 5220 includes an input terminal 5228 and an output terminal 5232. The current DAC 5222 includes an input terminal 5234 and an output terminal 5236. The output terminal 5236 of the current DAC 5222 is electrically coupled to the output terminal 5114 of the ultrasonic transducer 260. The output terminal 5114 of the ultrasonic transducer 260 is also electrically coupled to the input terminal 5228 of the quantizer 5220. The output terminal 5232 of the voltage quantizer 5220 is electrically coupled to the input terminal 5234 of the current DAC 5222.

In operation, the current $I_{CMUT}$ may be the signal that the delta-sigma ADC 5180 converts from analog to digital. The voltage $D_{OUT}$ at the output terminal 5232 of the voltage quantizer 5220 may be considered the output of the delta-sigma ADC 5180 and may be a digital representation of the analog signal $I_{CMUT}$. The delta-sigma ADC 5180 includes a feedback loop where the capacitor 5110 (serving as a current integrator) and the voltage quantizer 5220 are in the forward path of the feedback loop and the current DAC 5222 is in the feedback path of the feedback loop. The capacitor 5110 may be configured to integrate $I_{CMUT}$ to produce an output voltage. The quantizer 5220 may be configured to accept this output voltage as an input and outputs a digital logic level depending on whether the voltage is less than or greater than a threshold voltage. This digital logic level, over time, may be the output $D_{OUT}$ of the delta-sigma ADC. The current DAC 5222 may be configured to accept the digital logic level as an input and output a corresponding analog current $I_{feedback}$. Through the feedback loop, $I_{feedback}$ may be added to $I_{CMUT}$ at the output terminal 5114 of the ultrasonic transducer 260. This feedback loop may provide negative feedback, as in response to a positive input signal to the quantizer 5220, the quantizer 5220 may output a digital logic level that is converted by the current DAC 5222 to a negative $I_{feedback}$, and vice versa. $D_{OUT}$ may be a pulse stream in which the frequency of pulses may be proportional to the input to the delta-sigma ADC 5180, namely the analog current signal $I_{CMUT}$. This frequency may be enforced by the feedback loop of the delta-sigma ADC 5180. The delta-sigma ADC 5180 may oversample (e.g., at the quantizer 5220) the processed input current signal $I_{CMUT}$, and a filter may decimate the oversampled signal, in order to improve the signal-to-quantization-noise ratio (SQNR) of the delta-sigma ADC 5180.

It should be appreciated that in some embodiments, different architectures for the delta-sigma ADC 5180 may be used. In some embodiments, the delta-sigma ADC 5180 may be a second or third order delta-sigma ADC. In some embodiments, the delta-sigma ADC 5180 may include a second-order loop-filter. In some embodiments, the delta-sigma ADC 5180 may include a third-order loop-filter. In some embodiments, the delta-sigma ADC 5180 may include two feedback paths. In some embodiments, the delta-sigma ADC 5180 may include three feedback paths. In some embodiments, the delta-sigma ADC 5180 may include one feedback path and one feedforward path. In some embodiments, the delta-sigma ADC 5180 may include two feedback paths and one feedforward path.

Various aspects of the present disclosure may be used alone, in combination, or in a variety of arrangements not specifically described in the embodiments described in the foregoing and is therefore not limited in its application to the details and arrangement of components set forth in the foregoing description or illustrated in the drawings. For example, aspects described in one embodiment may be combined in any manner with aspects described in other embodiments.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

The terms "approximately" and "about" may be used to mean within ±20% of a target value in some embodiments, within ±10% of a target value in some embodiments, within ±5% of a target value in some embodiments, and yet within ±2% of a target value in some embodiments. The terms "approximately" and "about" may include the target value.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Having described above several aspects of at least one embodiment, it is to be appreciated various alterations, modifications, and improvements will readily occur to those skilled in the art. Such alterations, modifications, and improvements are intended to be object of this disclosure. Accordingly, the foregoing description and drawings are by way of example only.

What is claimed is:

1. An ultrasound device, comprising:
   a plurality of capacitive micromachined ultrasonic transducers (CMUT);
   a first application-specific integrated circuit (ASIC) comprising a pulser configured to provide a signal to a CMUT of the plurality of CMUTs, integrated analog processing receive circuitry configured to process a signal produced by the CMUT in response to receiving an acoustic signal, an analog-to-digital converter (ADC) configured to digitize a signal provided by the analog processing receive circuitry, and serial-deserialized (SERDES) transmit circuitry, wherein the first ASIC is configured to operate at a first operating voltage in a range of approximately 30-80 Volts;
   a second ASIC comprising SERDES receive circuitry and integrated digital processing circuitry configured to digitally process a signal provided by the SERDES receive circuitry, wherein the integrated digital processing circuitry is configured to operate at a second operating voltage in a range of approximately 0.45-0.9 Volts; and
   a SERDES communication link coupling the SERDES transmit circuitry of the first ASIC and the SERDES receive circuitry of the second ASIC.

2. The ultrasound device of claim 1, wherein the SERDES communication link comprises a through-silicon via (TSV).

3. The ultrasound device of claim 1, wherein the first ASIC is implemented in a first technology node, the second ASIC is implemented in a second technology node, and the first technology node is different than the second technology node.

4. The ultrasound device of claim 3, wherein the second technology node is a smaller technology node than the first technology node.

5. The ultrasound device of claim 3, wherein the first technology node is 65 nm, 80 nm, 90 nm, 110 nm, 130 nm, 150 nm, 180 nm, 220 nm, 240 nm, 250 nm, 280 nm, 350 nm, or 500 nm.

6. The ultrasound device of claim 3, wherein the second technology node is 90 nm, 80 nm, 65 nm, 55 nm, 45 nm, 40 nm, 32 nm, 28 nm, 22 nm, 20 nm, 16 nm, 14 nm, 10 nm, 7 nm, 5 nm, or 3 nm.

7. The ultrasound device of claim 1, wherein:
   the SERDES communication link has a data rate of approximately 2-5 gigabits/second.

8. The ultrasound device of claim 1, wherein the SERDES communication link is a first SERDES communication link, and wherein the ultrasound device comprises multiple SERDES communication links operating in parallel and coupling the SERDES transmit circuitry of the first ASIC and the SERDES receive circuitry of the second ASIC.

9. The ultrasound device of claim 1, wherein:
the analog-to-digital converter (ADC) is one of multiple ADCs; and
the SERDES transmit circuitry is configured to receive data from the multiple ADCs in a multiplexed fashion.

10. The ultrasound device of claim 1, wherein the ADC of the first ASIC is disposed electrically between the integrated analog processing receive circuitry and the SERDES transmit circuitry of the first ASIC.

11. The ultrasound device of claim 10, further comprising a printed circuit board (PCB), wherein:
the SERDES communication link comprises a trace of the PCB, and the SERDES receive circuitry of the second ASIC is disposed between the trace of the PCB and the integrated digital processing circuitry of the second ASIC.

12. The ultrasound device of claim 1, further comprising a printed circuit board (PCB), wherein:
the SERDES communication link comprises a trace of the PCB, and
the SERDES receive circuitry of the second ASIC is disposed between the trace of the PCB and the integrated digital processing circuitry of the second ASIC.

13. The ultrasound device of claim 1, further comprising a printed circuit board (PCB), wherein the first and second ASICs are both coupled to the PCB.

14. The ultrasound device of claim 1, wherein the first ASIC is disposed electrically between the plurality of CMUTs and the second ASIC.

* * * * *